United States Patent [19]
Smith et al.

[11] Patent Number: 6,027,914
[45] Date of Patent: Feb. 22, 2000

[54] NUCLEIC ACIDS ENCODING CR6 POLYPEPTIDE VECTOR AND TRANSFORMED CELL THEREOF, AND EXPRESSION THEREOF

[75] Inventors: Kendall A. Smith, New York, N.Y.; Carol Beadling, London, United Kingdom

[73] Assignee: Trustees of Dartmouth College, Hanover, N.H.

[21] Appl. No.: 08/465,585

[22] Filed: Jun. 5, 1995

Related U.S. Application Data

[63] Continuation-in-part of application No. 08/330,108, Oct. 27, 1994, abandoned, which is a continuation of application No. 08/104,736, Aug. 10, 1993, abandoned, which is a continuation of application No. 07/796,066, Nov. 20, 1991, abandoned.

[51] Int. Cl.$^7$ ............................ C12N 15/13; C12N 15/63; C07K 14/435; C07K 15/42
[52] U.S. Cl. .................. 435/69.1; 435/172.3; 435/320.1; 536/23.5; 536/24.33
[58] Field of Search ................................. 536/23.5, 24.5, 536/24.32, 23.1, 24.33; 435/65.1, 69.1, 320.1, 72.3, 69.7

[56] References Cited

PUBLICATIONS

Greenberg, et al. J. Biol. Chem. Vol. 260(26): pp 14101–14110, 1985.
PCT International Search Report (PCT/US96/09194).
Cochran, B.H., et al., "Molecular cloning of gene sequences regulated by platelet–derived growth factor", Cell, 33: 939–947, (July 1983).
Abdollahi, A. et al. (1991) "Sequence and expression of a cDNA encoding MyD118: a novel myeloid differentiation primary response gene induced by multiple cytokines" Oncogene 6:165–167.
Akazawa, C. et al. (1992) "Molecular Characterization of a Rat Negative Regulator with a Basic Helix–Loop–Helix Structure Predominantly Expressed in the Developing Nervous System" J. Biol. Chem. 267:21879–21855.
Almendral, J.M. et al. (1988) "Complexity of the Early Genetic Response to Growth Factors in Mouse Fibroblasts" Mol. Cell. Biol. 8:2140–2148.
Augustine, J.A. et al. (1991) "Interleukin 2–and polyomavirus middle T antigen–induced modification of phosphatidylinositol 3–kinase activity in activated T lymphocytes" Mol. Cell. Biol.1:4431–4440.
Bain, G. et al. (1994) "E2A Proteins are Required for Proper B Cell Development and Initiation of Immunoglobulin Gene Arrangements" Cell 79:885–892.
Barone, M.V. et al. (1994) "Id Proteins Control Growth Induction in Mammalian Cells" PNAS USA 91:4985–4988.
Beadling, C. et al. (1994) "Activation of JAK kinases and STAT proteins by interleukin–2 and interferon alpha, but not the T cell antigen receptor in human T Lymphocytes" EMBO J. 13:5605–5615.
Beading, C. et al. (1993) "Isolation of Interleukin–2–induced Immediate–early Genes" PNAS USA 90:2719–2723.
Begley, C.G. et al. (1989) "The Gene SCL is Expressed During Early Hematopoiesis and Encodes a Differentiation–related DNA–binding Motif" PNAS USA 86:10128–10132.
Benezra, R. et al. (1990) "The protein Id: a negative regulator of helix–loop–helix DNA binding proteins" Cell 61:49–59.
Bier, E. et al. (1992) "Deadpan, an Essential Pan–neural Gene in Drosophila, Encodes a Helix–Loop–Helix Protein Similar to the Hairy Gene Product" Genes and Dev. 6:2137–2151.
Blackwood, E.M. and R.N. Eisenman (1991) "Max: a helix–loop–helix zipper protein that forms a sequence–specific DNA–binding complex with Myc." Science 251:1211–1217.
Boie, Y. et al. (1994) "Cloning and Expression of a cDNA for the Human Prostanoid IP Receptor" J. Biol. Chem. 269(16):12173–12178.
Caudy, M. et al. (1988) "Daughterless, a Drosophila Gene Essential for Both Neurogenesis and Sex Determination, Has Sequence Similarities to Myc and the Achaete–Acute Complex" Cell 55:1061–1067.
Chen, Q. et al. (1990) "The Tal Gene Undergoes Chromosome Translocation in T Cell Leukemia and Potentially Encodes a Helix–Loop–Helix Protein" EMBO J. 9:415–424.
Cochran, B.H. et al. (1984) "Molecular Cloning of Gene Sequences Regulated by Platelet–derived Growth Factor" Cell 33:939–947.
Cramer, C.L. et al. (1985) "Rapid switching of plant gene expression induced by fungal elicitor" Science 227:1240–1243.
Dang, C.V. et al. (1992) "Discrimination Between Related DNA Sites by a Single Amino Acid Residue of Myc–related Basic–helix–loop–helix Proteins" PNAS USA 89:599–602.
Dautry, F. et al. (1988) "Regulation of Pim and Myb mRNA Accumulation by Interleukin 2 and Interleukin 3 in Murine Hematopoietic Cell Lines" J. Biol. Chem. 263:17615–17620.
Davis, R.L. et al. (1990) "The MyoD DNA Binding Domain Contains a Recognition Code for Muscle–specific Gene Activation" Cell 60:733–746.

(List continued on next page.)

Primary Examiner—Stephen Walsh
Assistant Examiner—Daryl A. Basham
Attorney, Agent, or Firm—Viviana Amzel; Pretty, Schroeder & Poplawski

[57] ABSTRACT

Early-induced genes by interleukin-2 (IL-2) have various DNA sequences. This patent describes a nucleotide segment, such as SEQ. ID No: 11, SEQ. ID No. 31, or encoding a polypeptide of amino acids 1–159 of SEQ. ID No: 12, antibody binding homologues thereof, antibody binding fragments, and fusion proteins thereof, alleles or naturally occurring mutants of the polyribonucleotides, and anti-sense polyribonucleotides thereof. Also provided are proteins, homologues, fragments, fusion proteins, vectors, transfected hosts, animal models, probes, and other related technology.

42 Claims, 2 Drawing Sheets

OTHER PUBLICATIONS

Delidakis, C. and S. Artavanis–Tsakonas (1992) "The Enhancer of Split [E(spl)] Locus Drosophila Encodes Seven Independent Helix–Loop–Helix Proteins" *PNAS USA* 89:8731–8735.

Dickinson, L.A. et al. (1992) "A Tissue–Specific MAR/SAR DNA–Binding Protein with Unusual Binding Site Recognition" *Cell* 70:631–645.

Edmondson, D.G. and E.N. Olson (1993) "Helix–loop–helix Proteins as Regulators of Muscle–specific Transcription" *J. Biol. Chem.* 268:755–758.

Einat, M. et al. (1985) "Close link between reduction of c–myc expression by interferon and G0/G1 arrest" *Nature* 313:597–600.

Ellis, H.M. et al. (1990) "Extramacrochaetae, a Negative Regulator of Sensory Organ Development in *Drosophila*, Defines a New Class of Helix–Loop–Helix Proteins" *Cell* 61:27–38.

Feder, J.N. et al. (1994) "Genomic Cloning and Chromosomal Localization of HRY, the Human Homolog to the Drosophila Segmentation Gene, Hairy" *Genomics* 20:56–61.

Feder, J.N. et al. (1993) "A Rat Gene with Sequence Homology to the Drosophila Gene hairy Is Rapidly Induced by Growth Factors Known To Influence Neuronal Differentiation" *Mol. Cell Biol.* 13(1):105–113.

Ferré–D'Amaré, A.R. et al. (1993) "Recognition by Max of its Cognate DNA Through a Dimeric b/HLH/Z Domain" *Nature* 363:38–45.

Ferré–D'Amaré, A.R. et al. (1994) "Structure and Function of the b/HLH/Z Domain of USF" *EMBO J.* 13:180–189.

Finger, L.R. et al. (1989) "Involvement of the TCL5 Gene on Human Chromosome 1 in T–cell Leukemia and Melanoma" *PNAS USA* 86:5039–5043.

Forsdyke, D.R. (1985) "cDNA Cloning of mRNAs Which Increase Rapidly in Human Lymphocytes Cultured with Concanavalin–A and Cycloheximide" *Biochem. & Biophys. Res. Comm.* 129(3):619–625.

Garrell, J. and J. Modolell (1990) "The Drosophila Extramacrochaetae Locus, an Antagonist of Proneural Genes That, Like These Genes, Encodes a Helix–Loop–Helix Protein" *Cell* 61:39–48.

Graves, J.D. et al. (1992) "The Growth Factor IL–2 Activates p21ras Proteins in Normal Human T Lymphocytes" *J. Immunol.* 148:2417–2422.

Gregor, P.D. et al. (1990) "The Adenovirus Major Late Transcription Factor USF is a Member of the Helix–Loop–Helix Group of Regulatory Proteins and Binds to DNA as a Dimer" *Genes & Dev.* 4:1730–1740.

Hara, E. et al. (1994) "Id–related Genes Encoding Helix–Loop–Helix Proteins are Required for G1 Progression and are Repressed in Senescent Human Fibroblasts" *J. Biol. Chem.* 269:2139–2145.

Hatakeyama, M. et al. (1985) "Reconstitution of functional receptor for human interleukin–2 in mouse cells" *Nature* 318:467–470.

Hong, J.X. et al. (1993) "Isolation and Characterization of a Novel B Cell Activation Gene" *J. Immunol.* 150(9):3895–3904.

Horak, I.D. et al. (1991) "T–lymphocyte Interleukin–2–dependent tyrosine protein kinase signal transduction involves the activation of p56lck" *PNAS USA* 88:1996–2000.

Iavarone, A. et al. (1994) "The helix–loop–helix protein Id–2 enhances cell proliferation and binds to the retinoblastoma protein" *Genes & Dev.* 8:1270–1284.

International Search Report for PCT/US92/10087, issued Mar. 1, 1993.

Ishibashi, M. et al. (1993) "Molecular Characterization of HES–2, a Mammalian Helix–Loop–Helix Factor Structurally Related to Drosophila Hairy and Enhancer of Split" *Eur. J. Biochem.* 215:645–652.

Jan, Y.N. and L.Y. Jan (1993) "HLH Proteins, Fly Neurogenesis, and Vertebrate Myogenesis" *Cell* 75:827–830.

Johnson, K.W. and K.A. Smith (1990) "cAMP Regulation of IL–2 Receptor Expression" *J. Immunol.* 145:1144–1151.

Johnson, K.W. et al. (1988) "cAMP Antagonizes Interleukin 2–promoted T–cell Cycle Progression at a Discretepoint in Early G1" *PNAS USA* 85:6072–6076.

Kadesch, T. (1992) "Helix–Loop–Helix Proteins in the Regulation of Immunoglobulin Gene Transcription" *Immunol. Today* 13:31–36.

Klämbt, C. et al. (1989) "Closely Related Transcripts Encoded by the Neurogenic Gene Complex Enhancer of Split of Drosophila Melanogaster" *EMBO J.* 8:203–210.

Knust, E. et al. (1992) "Seven Genes of the Enhancer of Split Complex of Drosophila Melanogaster Encode Helix–Loop–Helix Proteins" *Genetics* 132:505–518.

Kondo, S. et al. (1986) "Expression of functional human interleukin–2 receptor in mouse T cells by cDNA transfection" *Nature* 320:75–77.

Kuo, L.–M. and R.J. Robb (1986) "Structure–Function Relationships for the IL 2–Receptor System I. Localization of a Receptor Binding Site on IL–2" *J. Immunol.* 137:1538–1543.

Marcu, K.B. et al. (1992) "Myc Function and Regulation" *Annu. Rev. Biochem.* 61:809–860.

Melvin, W.T. and H.M. Keir (1977) "Affinity Chromatography of Thiol–Containing Purines and Ribonucleic Acid" *Biochem. J.* 168:595–597.

Merida, I. et al. (1991) "IL–2 binding activates a tyrosine–phosphorylated phosphatidylinositol–3–kinase" *J. Immunol.* 147:2202–2207.

Minami, Y. et al. (1995) "Protein tyrosine kinase Syk is associated with and activated by the IL–2 receptor: possible link with the c–myc induction pathway" *Immunity* 2(1):89–100.

Miyazaki, T. et al. (1994) "Functional activation of Jak1 and Jak3 by selective association with IL–2 receptor subunits" *Science* 266:1045–1047.

Murre, C. et al. (1989) "Interactions between heterologous helix–loop–helix proteins generate complexes that bind specifically to a common DNA sequence" *Cell* 58:537–544.

Murre, C. et al. (1989) "A new DNA binding and dimerization motif in immunoglobulin enhancer binding, daughterless, MyoD, and myc proteins" *Cell* 56:777–783.

Ohsako, S. et al. (1994) "Hairy Function as a DNA–binding helix–loop–helix repressor of Drosophila sensory organ formation" *Genes & Dev.* 8:2743–2755.

Papathanasiou, M.A. et al. (1991) "Induction by Ionizing Radiation of the gadd45 Gene in Cultured Human Cells: Lack of Mediation by Protein Kinase C" *Mol. Cell Biol.* 11(2):1009–1016.

Paroush, Z. et al. (1994) "Groucho is Required for Drosophila Neurogenesis, Segmentation and Sex Determination and Interacts Directly with Hairy–related bHLH Proteins" *Cell* 79;805–815.

Pognonec, P. and R.G. Roeder (1994) "Recombinant 43–kDa USF binds to DNA and activates transcription in a manner in a manner indistinguishable from that of natural 43/44–kDa USF" *Mol. Cell. Biol.* 11:5125–5136.

Prendergast, G.C. et al. (1991) "Association of Myn, the murine homolog of Max, with c–Myc stimulates methylation–sensitive DNA binding and ras cotransformation" *Cell* 65:395–407.

Reed, J.C. et al. (1986) "Sequential expression of protooncogenes during lectin–stimulated mitogenesis of normal human lymphocytes" *PNAS USA* 83:3982–3986.

Remillard, B. et al. (1991) "Interleukin–2 receptor regulates activation of phosphatidylinositol 3–kinase" *J. Biol. Chem.* 266:14167–14170.

Rushlow, C.A. et al. (1989) "The Drosophila hairy protein acts in both segmentation and bristle patterning and shows homology to N–myc" *EMBO J.* 8:3095–3103.

Russell, S.M. et al. (1994) "Interaction of IL–2Rbeta and gamma chains with Jak1 and Jak3: implications for XSCID and XCID" *Science* 266:1042–1045.

Sabath, D.E. et al. (1990) "cDNA Cloning and Characterization of Interleukin 2–induced Genes in a Cloned T Helper Lymphocyte" *J. Biol. Chem.* 265(21):12671–12678.

Sabath, D.E et al. (1986) "Cloned T–cell proliferation and synthesis of specific proteins are inhibited by quinine" *PNAS USA* 83:4739–4743.

Sasai, Y. et al. (1992) "Two mammalian helix–loop–helix factors structurally related to Drosophila hairy and Enhancer of split" *Genes & Dev.* 6:2620–2634.

Satoh, T. et al. (1991) "Involvement of ras p21 protein in signal–transduction pathways form interleukin 2, interleukin 3, and granulocyte–macrophage colony–stimulating factor, but not from interleukin–4" *PNAS USA* 88:3314–3318.

Sawami, H. et al. (1992) "Signal transduction by interleukin 2 in human T cells: activation of tyrosine and ribosomal S6 kinase and cell–cycle regulatory genes" *J. Cell. Physiol.* 151:367–377.

Selten, G. et al. (1986) "The Primary Structure of the Putative Oncogene pim–1 Shows Extensive Homology with Protein Kinases" *Cell* 46:603–611.

Sharon, M. et al. (1986) "Novel Interleukin–2 Receptor Subunit Detected by Cross–Linking Under High–Affinity Conditions" *Science* 234:859–863.

Shivdasani, R.A. et al. (1995) "Absence of blood formation in mice lacking the T–cell leukaemia oncoprotein tal–1/SCL" *Nature* 373:432–434.

Siderovski, D.P. et al. (1994) "A Human Gene Encoding a Putative Basic Helix–Loop–Helix Phosphoprotein Whose mRNA Increases Rapidly in Cycloheximide–Treated Blood Mononuclear Cells" *DNA and Cell Biology* 13(2):125–147.

Slamon, D.J. et al. (1986) "Identification and characterization of the protein encoded by the human N–myc oncogene" *Science* 232:768–772.

Smith, K.A. (1988) "Interleukin–2: inception, impact, and implications" *Science* 240:1169–1176.

Smith, M.L. et al. (1994) "Interaction of the p53–Regulated Protein Gadd45 with Proliferating Cell Nuclear Antigen" *Science* 266:1376–1380.

Stern, J.B. and K.A. Smith (1986) "Interleukin–2 induction of T–cell G1 progression and c–myb expression" *Science* 233:203–206.

Stetler, G.L. and J. Thorner (1984) "Molecular cloning of hormone–responsive genes from the yeast *Saccharomyces cerevisiae*" *PNAS USA* 81:1144–1148.

Stifani, S. et al. (1992) "Human Homologs of a Drosophila Enhancer of Split Gene Product Define a Novel Family of Nuclear Proteins" *Nat. Genet.* 2:119–127.

Telerman et al. (1988) "Indentification of the Human pim–1 Gene Product as a 33–Kilodalton Cytoplasmic Protein with Tyrosine Kinase Activity" *Mol. Cell. Biol.* 8:1498–1503.

Tietze, K. et al. (1992) "Enhancer of splitD, a dominant mutation of Drosophila, and its use in the study of functional domains of a helix–loop–helix protein" *PNAS USA* 89:6152–6156.

Turner, B. et al. (1991) "Interleukin 2 induces tyrosine phosphorylation and activation of p72–74 Raf–1 kinase in a T–cell line" *PNAS USA* 88:1227–1231.

Van Doren, M. et al. (1994) "Negative Regulation of Proneural Gene Activity: Hairy is a Direct Transcriptional Repressor of Achaete" *Genes & Dev.* 8:2729–2742.

Van Obberghen–Schilling, E. et al. (1982) "Hirudin, A Probe to Analyze the Growth–Promoting Activity of Thrombin in Fibroblasts; Reevaluation of the Temporal Action of Competence Factors" *Biochem. & Biophys. Res. Comm.* 106:79–86.

Villares, R. and C.V. Cabrera (1987) "The achaete–acute gene complex of D. melanogaster: conserved domains in a subset of genes required for neurogenesis and their homology to myc" *Cell* 50:415–424.

Wainwright, S.M. and D. Ish–Horowicz (1992) "Point Mutation in the Drosophila hairy gene demonstrate in vivo requirement for basic, helix–loop–helix, and WRPW domains" *Mol. Cell. Biol.* 12:2475–2483.

Waksman, G. et al. (1993) "Binding of a High Affinity Phosphotyrosyl Peptide to the Src SH2 Domain: Crystal Structures of the Complexed and Peptide–free Forms" *Cell* 72:779–790.

Weintraub, H. (1993) "The MyoD family and myogenesis: redundancy, networks, and thresholds" *Cell* 75(7):1241–1244.

Weiss, A. and D.R. Littman (1994) "Signal transduction by lymphocyte antigen receptors" *Cell* 76:263–274.

Woodford, T.A. et al. (1988) "Selective Isolation of Newly Synthesized Mammalian mRNA After in Vivo Labeling with 4–thiouridine or 6–thioguanosine" *Anal. Biochem.* 171:166–172.

Zakut–Houri, R. et al. (1987) "The cDNA sequence and gene analysis of the human pim oncogene" *Gene* 54:105–111.

Zhuang, Y. et al. (1994) "The helix–loop–helix gene E2A is required for B cell formation" *Cell* 79:875–884.

Zmuidzinas, A. et al. (1991) "Interleukin–2–triggered Raf–1 expression, phosphorylation, and associated kinase activity increase through G1 and S in CD3–stimulated primary human T cells" *Mol. Cell. Biol.* 11:2794–2803.

NUCLEIC ACIDS ENCODING CR6 POLYPEPTIDE VECTOR AND TRANSFORMED CELL THEREOF, AND EXPRESSION THEREOF

RELATED APPLICATIONS

This application is a continuation-in-part application of U.S. patent application Ser. No. 08/330,108, filed Oct. 27, 1994 (now abandoned), which is a continuation application of U.S. patent application Ser. No. 08/104,736, filed Aug. 10, 1993 (now abandoned), which is in turn a continuation application of U.S. patent application Ser. No. 07/796,066, filed Nov. 20, 1991 (now abandoned). The contents of these prior applications are hereby incorporated by reference.

GOVERNMENT SUPPORT

Work described herein was supported in part by funding from the National Institute of Health, Grant number 5 RO1 -AI-32031-20. The United States Government has certain rights in the invention.

BACKGROUND OF THE INVENTION

Mammalian cell growth, differentiation, and migration are directed by hormones and specific protein ligands, often termed cytokines. In particular, cells comprising the neuro-endocrine, hematopoietic and the immune/inflammatory systems are known to be governed by cytokines. Cytokines, like other ligands, interact with cells by means of specific receptors, usually expressed on the cell surface.

A fundamental problem confronting biomedical scientists is to discern how signals are transduced through ligand receptors and how these signals determine the response of the cell. Many ligands influence their target cells by stimulating the expression of specific genes. However, the genes signaled by most cytokines remain largely unknown owing to the complexity of cellular biochemistry. Moreover, the gene products that are vital for performing different cellular processes are often only expressed transiently, and/or in very low concentrations so that they are difficult to detect, isolate and characterize Interleukin-2 (IL-2) is a cytokine that is critical for the immune system: it directs the proliferation and differentiation of T lymphocytes (T-cells), B lymphocytes (B-cells), and natural killer (NK) cells. Just how IL-2 signals these cellular events in the various types of target cells remains unknown. A few genes have been identified that are expressed as a result of IL-2 stimulation of T cells. These include the cellular proto-oncogenes c-fos, c-myb, c-myc, pim-1 , and c-raf-1. However, exactly how many and what other genes are expressed as a result of IL-2/IL-2 receptor interaction remains unknown.

Since the discovery of DNA cloning, methods have become available to isolate specific genes expressed by cells. However, it has been difficult to devise new methods to isolate and clone all or most of the genes expressed by a cell activated by a given ligand, a task that must be done before one can understand how the ligand directs the cell to perform specific functions. In addition, methods of identifying a particular gene or genes stimulated early on after ligand receptor activation have not been easily forthcoming as the number of genes stimulated by receptor activation from which a particular gene must be selected is usually quite large.

Therefore, what is needed are methods to select and enrich only for those genes stimulated by a given ligand. Ideally, these methods should detect those genes expressed in low concentrations, as well as those expressed at high concentrations.

SUMMARY OF THE INVENTION

This invention pertains to complementary deoxyribonucleic acid (cDNA) libraries enriched in clones containing genes induced by ligand stimulation of a cell having a corresponding receptor for the ligand, and to methods of producing the same. This invention also relates to the genes which are expressed immediately or early on as a consequence of such a ligand-receptor interaction, and to methods of identifying these genes.

In the method of producing a cDNA library enriched in ligand-inducible genes, a cellular ligand receptor on a cell is activated with a ligand, for a predetermined period of time, to induce expression of those genes expressed as a result of ligand-receptor binding. Useful ligands include any of those which can activate a specific cellular receptor. These include natural or synthetic ligands for the receptor. Ligands include cytokines such as the interleukins, cellular growth factors, colony stimulating factors, hormones, peptides, antibodies, and receptor-binding fragments thereof.

The cells are activated with the ligand in the presence of labelled RNA precursors. These precursors are incorporated into RNA synthesized by the cell in response to receptor activation. Labelled precursors are used in order to distinguish newly transcribed RNA from unlabelled, preexisting RNA. Preferred labelled RNA precursors include 6-thioguanine, 4-thiouridine, and tritiated uridine.

Activation is also carried out in the presence of a substance which enhances the level of RNA in a cell. Preferred substances include the protein synthesis inhibitors, cycloheximide and puromycin. Other useful substances include cyclic 3',5'-adenosine monophosphate (cAMP), analogs of cAMP such as dibutyryl cAMP, and other molecules which increase the intracellular level of cAMP. The labelled RNA is then separated from the unlabelled RNA and used to prepare cDNA. The cDNA is cloned into host cells to provide a cDNA library of cDNA-containing clones. This library is then screened for clones containing ligand-inducible genes.

In one embodiment of the invention, the screening step includes probing the cDNA library with a DNA probe constructed from total cellular RNA or mRNA derived from (1) a ligand-induced cell and from (2) an uninduced cell. The library is probed under conditions such that the probe hybridizes specifically with a complementary cDNA sequence in the library. The selecting step includes selecting those clones containing sequences that hybridize only with probes constructed from ligand-induced mRNA or total RNA.

By following the method of the invention, eight clones containing ligand-induced genes have been identified. These genes have been named Cytokine Response (CR) genes 1-8. CR genes 1–3, 5, 6, and 8 are novel. CR4 is identical to a gene reported as SATB-1 (Dickinson, L. A. et al. (1992) Cell 70:631–645), for Special AT-rich Binding protein 1, which binds selectively to the nuclear matrix/scaffold-associating region of DNA. CR7, also identified using the method of the invention, is identical to the putative proto-oncogene, pim 1, a known IL-2-induced gene. The nucleic acid sequences of these CR genes, i.e., CR genes 1–6 and 8 are set forth in SEQ ID NOs:1, 3, 5, 7, 9, 11, and 13 and FIGS. 1–7. The amino acid sequences encoded by these CR genes are set forth in SEQ ID NOs.: 2, 4, 6, 8, 10, 12, and 14 as well as in SEQ ID NOs: 1, 3, 5, 7, 9, 11, and 13 and FIGS. 1–7.

The present invention, therefore, also pertains to a CR1 polypeptide, preferably a substantially pure preparation of a CRI polypeptide, or a recombinant CR1 polypeptide. In preferred embodiments, the CR1 polypeptide has an amino acid sequence at least 60%, 80%, 90% or 95% homologous to the amino acid sequence in SEQ ID NO:2; the polypeptide has an amino acid sequence essentially the same as the amino acid sequence in SEQ ID NO:2; the polypeptide is at least 5, 10, 20, 50, 100, or 150 amino acids in length; the polypeptide comprises at least 5, preferably at least 10, more preferably at least 20, more preferably at least 50, 100, or 150 contiguous amino acids from SEQ ID NO:2. In further preferred embodiments, a protein homologous to SEQ ID NO: 2 has a molecular weight of about 22 kilodaltons (kD), e.g. in the range of 15–30 kD.

In a preferred embodiment, a polypeptide having at least one biological activity of the CR1 polypeptide may differ in amino acid sequence from the sequence in SEQ ID NO:2, but such differences result in a modified polypeptide which functions in the same or similar manner as native CR1 protein or which has the same or similar characteristics of the native CR1 protein. Such a peptide can include at least 1, 2, 3, or 5, and preferably 10, 20, and 30, amino acid residues from residues 1–202 of SEQ ID NO:2.

In yet other preferred embodiments, the CR1 polypeptide is a recombinant fusion protein which includes a second polypeptide portion, e.g., a second polypeptide having an amino acid sequence unrelated to a protein represented by SEQ ID NO:2, e.g., the second polypeptide portion is glutathione-S-transferase, e.g., the second polypeptide portion is a DNA binding domain, e.g., the second polypeptide portion is a polymerase activating domain, e.g. the fusion protein is functional in a two-hybrid assay.

Yet another aspect of the present invention concerns an immunogen comprising a CR1 polypeptide in an immunogenic preparation, the immunogen being capable of eliciting an immune response specific for the CR1 polypeptide; e.g., a humoral response, e.g. an antibody response; e.g. a cellular response. In preferred embodiments, the immunogen comprises an antigenic determinant, e.g., a unique determinant, from a protein represented by SEQ ID NO:2. A further aspect of the present invention features an antibody preparation specifically reactive with an epitope of the CR1 immunogen.

Another aspect of the present invention provides a substantially pure nucleic acid having a nucleotide sequence which encodes a CR1 polypeptide. In preferred embodiments: the encoded polypeptide has at least one biological activity; the encoded polypeptide has an amino acid sequence at least 60%, 80%, 90% or 95% homologous to the amino acid sequence in SEQ ID NO:2; the encoded polypeptide has an amino acid sequence essentially the same as the amino acid sequence in SEQ ID NO:2; the encoded polypeptide is at least 5, 10, 20, 50, 100, or 150 amino acids in length; the encoded polypeptide comprises at least 5, preferably at least 10, more preferably at least 20, more preferably at least 50, 100, or 150 contiguous amino acids from SEQ ID NO:2.

In a preferred embodiment, the encoded polypeptide having at least one biological activity of the CR1 polypeptide may differ in amino acid sequence from the sequence in SEQ ID NO:2, but such differences result in a modified polypeptide which functions in the same or similar manner as the native CR1 or which has the same or similar characteristics of the native CR1.

In yet other preferred embodiments, the encoded CR1 polypeptide is a recombinant fusion protein which includes a second polypeptide portion, e.g., a second polypeptide having an amino acid sequence unrelated to a protein represented by SEQ ID NO:2, e.g., the second polypeptide portion is glutathione-S-transferase, e.g. the second polypeptide portion is a DNA binding domain, e.g., the second polypeptide portion is a polymerase activating domain, e.g., the fusion protein is functional in a two-hybrid assay.

Furthermore, in certain preferred embodiments, the subject CR1 nucleic acid includes a transcriptional regulatory sequence, e.g. at least one of a transcriptional promoter or transcriptional enhancer sequence, operably linked to the CR1 gene sequence, e.g., to render the CR1 gene sequence suitable for use as an expression vector.

In yet a further preferred embodiment, the nucleic acid which encodes a CR1 polypeptide of the invention hybridizes under stringent conditions to a nucleic acid probe corresponding to at least 12 consecutive nucleotides of SEQ ID NO:1; more preferably to at least 20 consecutive nucleotides of SEQ ID NO:1; more preferably to at least 40 consecutive nucleotides of SEQ ID NO:1. In yet a further preferred embodiment, the CR1 encoding nucleic acid hybridizes to a nucleic acid probe corresponding to a subsequence encoding at least 4 consecutive amino acids, more preferably at least 10 consecutive amino acid residues, and even more preferably at least 20 amino acid residues between residues 1–202 of SEQ ID NO:2.

In preferred embodiments: the nucleic acid sequence includes at least 1, 2, 3 or 5, and preferably at least 10, 20, 50, or 100 nucleotides from the region of SEQ ID NO:1 which encodes amino acid residues 1–202 of SEQ ID NO:2; the encoded peptide includes at least 1, 2, 3, 5, 10, 20, or 30 amino acid residues from amino acid residues 1–202 of SEQ ID NO:2.

The present invention also pertains to a CR2 polypeptide, preferably a substantially pure preparation of a CR2 polypeptide, or a recombinant CR2 polypeptide. In preferred embodiments, the CR2 polypeptide has an amino acid sequence at least 60%, 80%, 90% or 95% homologous to the amino acid sequence in SEQ ID NO:4; the polypeptide has an amino acid sequence essentially the same as the amino acid sequence in SEQ ID NO:4; the polypeptide is at least 5, 10, 20, 50, 100, or 150 amino acids in length; the polypeptide comprises at least 5, preferably at least 10, more preferably at least 20, more preferably at least 50, 100, or 150 contiguous amino acids from SEQ ID NO:4. In further preferred embodiments, a protein homologous to SEQ ID NO:4 has a molecular weight of about 6 kilodaltons (kD), e.g. in the range of 5–15 kD.

In a preferred embodiment, a polypeptide having at least one biological activity of the CR2 polypeptide may differ in amino acid sequence from the sequence in SEQ ID NO:4, but such differences result in a modified polypeptide which functions in the same or similar manner as native CR2 protein or which has the same or similar characteristics of the native CR2 protein. Such a peptide can include at least 1, 2, 3, or 5, and preferably 10, 20, and 30, amino acid residues from residues 1–60 of SEQ ID NO:4.

In yet other preferred embodiments, the CR2 polypeptide is a recombinant fusion protein which includes a second polypeptide portion, e.g., a second polypeptide having an amino acid sequence unrelated to a protein represented by SEQ ID NO:4, e.g., the second polypeptide portion is glutathione-S-transferase, e.g., the second polypeptide portion is a DNA binding domain, e.g., the second polypeptide portion is a polymerase activating domain, e.g., the fusion protein is functional in a two-hybrid assay.

Yet another aspect of the present invention concerns an immunogen comprising a CR2 polypeptide in an immunogenic preparation, the immunogen being capable of eliciting an immune response specific for the CR2 polypeptide; e.g. a humoral response, e.g. an antibody response; e.g. a cellular response. In preferred embodiments, the immunogen comprises an antigenic determinant, e.g. a unique determinant, from a protein represented by SEQ ID NO:4. A further aspect of the present invention features an antibody preparation specifically reactive with an epitope of the CR2 immunogen.

Another aspect of the present invention provides a substantially pure nucleic acid having a nucleotide sequence which encodes a CR2 polypeptide. In preferred embodiments: the encoded polypeptide has at least one biological activity; the encoded polypeptide has an amino acid sequence at least 60%, 80%, 90% or 95% homologous to the amino acid sequence in SEQ ID NO:4; the encoded polypeptide has an amino acid sequence essentially the same as the amino acid sequence in SEQ ID NO:4; the encoded polypeptide is at least 5, 10, 20, 50, 100, or 150 amino acids in length; the encoded polypeptide comprises at least 5, preferably at least 10, more preferably at least 20, more preferably at least 50, 100, or 150 contiguous amino acids from SEQ ID NO:4.

In a preferred embodiment, the encoded polypeptide having at least one biological activity of the CR2 polypeptide may differ in amino acid sequence from the sequence in SEQ ID NO:4, but such differences result in a modified polypeptide which functions in the same or similar manner as the native CR2 protein or which has the same or similar characteristics of the native CR2 protein.

In yet other preferred embodiments, the encoded CR2 polypeptide is a recombinant fusion protein which includes a second polypeptide portion, e.g., a second polypeptide having an amino acid sequence unrelated to a protein represented by SEQ ID NO:4, e.g. the second polypeptide portion is glutathione-S-transferase, e.g., the second polypeptide portion is a DNA binding domain, e.g., the second polypeptide portion is a polymerase activating domain, e.g., the fusion protein is functional in a two-hybrid assay.

Furthermore, in certain preferred embodiments, the subject CR2 nucleic acid includes a transcriptional regulatory sequence, e.g. at least one of a transcriptional promoter or transcriptional enhancer sequence, operably linked to the CR2 gene sequence, e.g., to render the CR2 gene sequence suitable for use as an expression vector.

In yet a further preferred embodiment, the nucleic acid which encodes a CR2 polypeptide of the invention hybridizes under stringent conditions to a nucleic acid probe corresponding to at least 12 consecutive nucleotides of SEQ ID NO:3; more preferably to at least 20 consecutive nucleotides of SEQ ID NO:3; more preferably to at least 40 consecutive nucleotides of SEQ ID NO:3. In yet a further preferred embodiment, the CR2 encoding nucleic acid hybridizes to a nucleic acid probe corresponding to a subsequence encoding at least 4 consecutive amino acids, more preferably at least 10 consecutive amino acid residues, and even more preferably at least 20 amino acid residues between residues 1–60 of SEQ ID NO:4.

In preferred embodiments: the nucleic acid sequence includes at least 1, 2, 3 or 5, and preferably at least 10, 20, 50, or 100 nucleotides from the region of SEQ ID NO:3 which encodes amino acid residues 1–60 of SEQ ID NO:4; the encoded peptide includes at least 1, 2, 3, 5, 10, 20, or 30 amino acid residues from amino acid residues 1–60 of SEQ ID NO:4.

The present invention further pertains to a CR3 polypeptide, preferably a substantially pure preparation of a CR3 polypeptide, or a recombinant CR3 polypeptide. In preferred embodiments, the CR3 polypeptide has an amino acid sequence at least 60%, 80%, 90% or 95% homologous to the amino acid sequence in SEQ ID NO:6; the polypeptide has an amino acid sequence essentially the same as the amino acid sequence in SEQ ID NO:6; the polypeptide is at least 5, 10, 20, 50, 100, or 150 amino acids in length; the polypeptide comprises at least 5, preferably at least 10, more preferably at least 20, more preferably at least 50, 100, or 150 contiguous amino acids from SEQ ID NO:6. In further preferred embodiments, a protein homologous to SEQ ID NO:6 has a molecular weight of about 88 kilodaltons (kD), e.g. in the range of 80–95 kD.

In a preferred embodiment, a peptide having at least one biological activity of the CR3 polypeptide may differ in amino acid sequence from the sequence in SEQ ID NO:6, but such differences result in a modified protein which functions in the same or similar manner as native CR3 protein or which has the same or similar characteristics of the native CR3 protein. Such a peptide can include at least 1, 2, 3, or 5, and preferably 10, 20, and 30, amino acid residues from residues 1–358 of SEQ ID NO:6.

In yet other preferred embodiments, the CR3 polypeptide is a recombinant fusion protein which includes a second polypeptide portion, e.g., a second polypeptide having an amino acid sequence unrelated to a protein represented by SEQ ID NO:6, e.g., the second polypeptide portion is glutathione-S-transferase, e.g., the second polypeptide portion is a DNA binding domain, e.g., the second polypeptide portion is a polymerase activating domain, e.g., the fusion protein is functional in a two-hybrid assay.

Yet another aspect of the present invention concerns an immunogen comprising a CR3 polypeptide in an immunogenic preparation, the immunogen being capable of eliciting an immune response specific for said CR3 polypeptide; e.g. a humoral response, e.g. an antibody response; e.g. a cellular response. In preferred embodiments, the immunogen comprises an antigenic determinant, e.g. a unique determinant, from a protein represented by SEQ ID NO:6. A further aspect of the present invention features an antibody preparation specifically reactive with an epitope of the CR3 immunogen.

Another aspect of the present invention provides a substantially pure nucleic acid having a nucleotide sequence which encodes a CR3 polypeptide. In preferred embodiments: the encoded polypeptide has at least one biological activity; the encoded polypeptide has an amino acid sequence at least 60%, 80%, 90% or 95% homologous to the amino acid sequence in SEQ ID NO:6; the encoded polypeptide has an amino acid sequence essentially the same as the amino acid sequence in SEQ ID NO:6; the encoded polypeptide is at least 5, 10, 20, 50, 100, or 150 amino acids in length; the encoded polypeptide comprises at least 5, preferably at least 10, more preferably at least 20, more preferably at least 50, 100, or 150 contiguous amino acids from SEQ ID NO:6.

In a preferred embodiment, the encoded polypeptide having at least one biological activity of the CR3 polypeptide may differ in amino acid sequence from the sequence in SEQ ID NO:6, but such differences result in a modified polypeptide which functions in the same or similar manner as the native CR3 protein or which has the same or similar characteristics of the native CR3 protein.

In yet other preferred embodiments, the encoded CR3 polypeptide is a recombinant fusion protein which includes a second polypeptide portion, e.g., a second polypeptide having an amino acid sequence unrelated to a protein represented by SEQ ID NO:6, e.g., the second polypeptide portion is glutathione-S-transferase, e.g., the second polypeptide portion is a DNA binding domain, e.g., the second polypeptide portion is a polymerase activating domain, e.g., the fusion protein is functional in a two-hybrid assay.

Furthermore, in certain preferred embodiments, the subject CR3 nucleic acid includes a transcriptional regulatory sequence, e.g. at least one of a transcriptional promoter or transcriptional enhancer sequence, operably linked to the CR3 gene sequence, e.g., to render the CR3 gene sequence suitable for use as an expression vector.

In yet a further preferred embodiment, the nucleic acid which encodes a CR3 polypeptide of the invention hybridizes under stringent conditions to a nucleic acid probe corresponding to at least 12 consecutive nucleotides of SEQ ID NO:5; more preferably to at least 20 consecutive nucleotides of SEQ ID NO:5; more preferably to at least 40 consecutive nucleotides of SEQ ID NO:5. In yet a further preferred embodiment, the CR3 encoding nucleic acid hybridizes to a nucleic acid probe corresponding to a subsequence encoding at least 4 consecutive amino acids, more preferably at least 10 consecutive amino acid residues, and even more preferably at least 20 amino acid residues between residues 1–358 of SEQ ID NO:6.

In preferred embodiments: the nucleic acid sequence includes at least 1, 2, 3 or 5, and preferably at least 10, 20, 50, or 100 nucleotides from the region of SEQ ID NO:5 which encodes amino acid residues 1–358 of SEQ ID NO:6; the encoded peptide includes at least 1, 2, 3, 5, 10, 20, or 30 amino acid residues from amino acid residues 1–358 of SEQ ID NO:6.

The present invention still further pertains to a CR4 polypeptide, preferably a substantially pure preparation of a CR4 polypeptide, or a recombinant CR4 polypeptide. In preferred embodiments, the CR4 polypeptide has an amino acid sequence at least 60%, 80%, 90% or 95% homologous to the amino acid sequence in SEQ ID NO:8; the polypeptide has an amino acid sequence essentially the same as the amino acid sequence in SEQ ID NO:8; the polypeptide is at least 5, 10, 20, 50, 100, or 150 amino acids in length; the polypeptide comprises at least 5, preferably at least 10, more preferably at least 20, more preferably at least 50, 100, or 150 contiguous amino acids from SEQ ID NO:8. In further preferred embodiments, a protein homologous to SEQ ID NO:8 has a molecular weight of about 83 kilodaltons (kD), e.g. in the range of 75–90 kD.

In a preferred embodiment, a polypeptide having at least one biological activity of the CR4 polypeptide may differ in amino acid sequence from the sequence in SEQ ID NO:8, but such differences result in a modified polypeptide which functions in the same or similar manner as native CR4 protein or which has the same or similar characteristics of the native CR4 protein. Such a peptide can include at least 1, 2, 3, or 5, and preferably 10, 20, and 30, amino acid residues from residues 1–763 of SEQ ID NO:8.

In yet other preferred embodiments, the CR4 polypeptide is a recombinant fusion protein which includes a second polypeptide portion, e.g., a second polypeptide having an amino acid sequence unrelated to a protein represented by SEQ ID NO:8, e.g., the second polypeptide portion is glutathione-S-transferase, e.g., the second polypeptide portion is a DNA binding domain, e.g., the second polypeptide portion is a polymerase activating domain, e.g., the fusion protein is functional in a two-hybrid assay.

Yet another aspect of the present invention pertains to an immunogen comprising a CR4 polypeptide in an immunogenic preparation, the immunogen being capable of eliciting an immune response specific for the CR4 polypeptide; e.g. a humoral response, e.g. an antibody response; e.g. a cellular response. In preferred embodiments, the immunogen comprises an antigenic determinant, e.g. a unique determinant, from a protein represented by SEQ ID NO:8. A further aspect of the present invention features an antibody preparation specifically reactive with an epitope of the CR4 immunogen.

Another aspect of the present invention provides a substantially pure nucleic acid having a nucleotide sequence which encodes a CR4 polypeptide. In preferred embodiments: the encoded polypeptide has at least one biological activity; the encoded polypeptide has an amino acid sequence at least 60%, 80%, 90% or 95% homologous to the amino acid sequence in SEQ ID NO:8; the encoded polypeptide has an amino acid sequence essentially the same as the amino acid sequence in SEQ ID NO:8; the encoded polypeptide is at least 5, 10, 20, 50, 100, or 150 amino acids in length; the encoded polypeptide comprises at least 5, preferably at least 10, more preferably at least 20, more preferably at least 50, 100, or 150 contiguous amino acids from SEQ ID NO:8.

In a preferred embodiment, the encoded polypeptide having at least one biological activity of the CR4 polypeptide may differ in amino acid sequence from the sequence in SEQ ID NO:8, but such differences result in a modified polypeptide which functions in the same or similar manner as the native CR4 protein or which has the same or similar characteristics of the native CR4 protein.

In yet other preferred embodiments, the encoded CR4 polypeptide is a recombinant fusion protein which includes a second polypeptide portion, e.g., a second polypeptide having an amino acid sequence unrelated to a protein represented by SEQ ID NO:8, e.g., the second polypeptide portion is glutathione-S-transferase, e.g. the second polypeptide portion is a DNA binding domain, e.g., the second polypeptide portion is a polymerase activating domain, e.g., the fusion protein is functional in a two-hybrid assay.

Furthermore, in certain preferred embodiments, the subject CR4 nucleic acid includes a transcriptional regulatory sequence, e.g., at least one of a transcriptional promoter or transcriptional enhancer sequence, operably linked to the CR4 gene sequence, e.g., to render the CR4 gene sequence suitable for use as an expression vector.

In yet a further preferred embodiment, the nucleic acid which encodes a CR4 polypeptide of the invention hybridizes under stringent conditions to a nucleic acid probe corresponding to at least 12 consecutive nucleotides of SEQ ID NO:7; more preferably to at least 20 consecutive nucleotides of SEQ ID NO:7; more preferably to at least 40 consecutive nucleotides of SEQ ID NO:7. In yet a further preferred embodiment, the CR4 encoding nucleic acid hybridizes to a nucleic acid probe corresponding to a subsequence encoding at least 4 consecutive amino acids, more preferably at least 10 consecutive amino acid residues, and even more preferably at least 20 amino acid residues between residues 1–763 of SEQ ID NO:8.

In preferred embodiments: the nucleic acid sequence includes at least 1, 2, 3 or 5, and preferably at least 10, 20, 50, or 100 nucleotides from the region of SEQ ID NO:7 which encodes amino acid residues 1–763 of SEQ ID NO:8; the encoded peptide includes at least 1, 2, 3, 5, 10, 20, or 30 amino acid residues from amino acid residues 1–763 of SEQ ID NO:8.

Another aspect of the present invention pertains to a CR5 polypeptide, preferably a substantially pure preparation of a CR5 polypeptide, or a recombinant CR5 polypeptide. In preferred embodiments, the CR5 polypeptide has an amino acid sequence at least 60%, 80%, 90% or 95% homologous to the amino acid sequence in SEQ ID NO:10; the polypeptide has an amino acid sequence essentially the same as the amino acid sequence in SEQ ID NO:10; the polypeptide is at least 5, 10, 20, 50, 100, or 150 amino acids in length; the polypeptide comprises at least 5, preferably at least 10, more preferably at least 20, more preferably at least 50, 100, or 150 contiguous amino acids from SEQ ID NO:10. In further preferred embodiments, a protein homologous to SEQ ID NO:10 has a molecular weight of about 28 kilodaltons (kD), e.g. in the range of 20–35 kD.

In a preferred embodiment, a polypeptide having at least one biological activity of the CR5 polypeptide may differ in amino acid sequence from the sequence in SEQ ID NO:10, but such differences result in a modified polypeptide which functions in the same or similar manner as native CR5 protein or which has the same or similar characteristics of the native CR5 protein. Such a peptide can include at least 1, 2, 3, or 5, and preferably 10, 20, and 30, amino acid residues from residues 1–258 of SEQ ID NO:10.

In yet other preferred embodiments, the CR5 polypeptide is a recombinant fusion protein which includes a second polypeptide portion, e.g., a second polypeptide having an amino acid sequence unrelated to a protein represented by SEQ ID NO:10, e.g., the second polypeptide portion is glutathione-S-transferase, e.g. the second polypeptide portion is a DNA binding domain, e.g., the second polypeptide portion is a polymerase activating domain, e.g., the fusion protein is functional in a two-hybrid assay.

Yet another aspect of the present invention concerns an immunogen comprising a CR5 polypeptide in an immunogenic preparation, the immunogen being capable of eliciting an immune response specific for the CR5 polypeptide; e.g. a humoral response, e.g. an antibody response; e.g. a cellular response. In preferred embodiments, the immunogen comprises an antigenic determinant, e.g. a unique determinant, from a protein represented by SEQ ID NO:10. A further aspect of the present invention features an antibody preparation specifically reactive with an epitope of the CR5 immunogen.

Another aspect of the present invention provides a substantially pure nucleic acid having a nucleotide sequence which encodes a CR5 polypeptide. In preferred embodiments: the encoded polypeptide has at least one biological activity; the encoded polypeptide has an amino acid sequence at least 60%, 80%, 90% or 95% homologous to the amino acid sequence in SEQ ID NO:10; the encoded polypeptide has an amino acid sequence essentially the same as the amino acid sequence in SEQ ID NO:10; the encoded polypeptide is at least 5, 10, 20, 50, 100, or 150 amino acids in length; the encoded polypeptide comprises at least 5, preferably at least 10, more preferably at least 20, more preferably at least 50, 100, or 150 contiguous amino acids from SEQ ID NO:10.

In a preferred embodiment, the encoded polypeptide having at least one biological activity of the CR5 polypeptide may differ in amino acid sequence from the sequence in SEQ ID NO:10, but such differences result in a modified polypeptide which functions in the same or similar manner as the native CR5 protein or which has the same or similar characteristics of the native CR5 protein.

In yet other preferred embodiments, the encoded CR5 polypeptide is a recombinant fusion protein which includes a second polypeptide portion, e.g., a second polypeptide having an amino acid sequence unrelated to a protein represented by SEQ ID NO:10, e.g., the second polypeptide portion is glutathione-S-transferase, e.g., the second polypeptide portion is a DNA binding domain, e.g., the second polypeptide portion is a polymerase activating domain, e.g. the fusion protein is functional in a two-hybrid assay.

Furthermore, in certain preferred embodiments, the subject CR5 nucleic acid includes a transcriptional regulatory sequence, e.g., at least one of a transcriptional promoter or transcriptional enhancer sequence, operably linked to the CR5 gene sequence, e.g., to render the CR5 gene sequence suitable for use as an expression vector.

In yet a further preferred embodiment, the nucleic acid which encodes an CR5 polypeptide of the invention hybridizes under stringent conditions to a nucleic acid probe corresponding to at least 12 consecutive nucleotides of SEQ ID NO:9; more preferably to at least 20 consecutive nucleotides of SEQ ID NO:9; more preferably to at least 40 consecutive nucleotides of SEQ ID NO:9. In yet a further preferred embodiment, the CR5 encoding nucleic acid hybridizes to a nucleic acid probe corresponding to a subsequence encoding at least 4 consecutive amino acids, more preferably at least 10 consecutive amino acid residues, and even more preferably at least 20 amino acid residues between residues 1–258 of SEQ ID NO:10.

In preferred embodiments: the nucleic acid sequence includes at least 1, 2, 3 or 5, and preferably at least 10, 20, 50, or 100 nucleotides from the region of SEQ ID NO:9 which encodes amino acid residues 1–258 of SEQ ID NO:10; the encoded peptide includes at least 1, 2, 3, 5, 10, 20, or 30 amino acid residues from amino acid residues 1–258 of SEQ ID NO:10.

The present invention further pertains to a CR6 polypeptide, preferably a substantially pure preparation of a CR6 polypeptide, or a recombinant CR6 polypeptide. In preferred embodiments, the CR6 polypeptide has an amino acid sequence at least 60%, 80%, 90% or 95% homologous to the amino acid sequence in SEQ ID NO:12; the polypeptide has an amino acid sequence essentially the same as the amino acid sequence in SEQ ID NO:12; the polypeptide is at least 5, 10, 20, 50, 100, or 150 amino acids in length; the polypeptide comprises at least 5, preferably at least 10, more preferably at least 20, more preferably at least 50, 100, or 150 contiguous amino acids from SEQ ID NO:12. In further preferred embodiments, a protein homologous to SEQ ID NO:12 has a molecular weight of about 17 kilodaltons (kD), e.g. in the range of 15–25 kD.

In a preferred embodiment, a polypeptide having at least one biological activity of the CR6 polypeptide may differ in amino acid sequence from the sequence in SEQ ID NO:12, but such differences result in a modified polypeptide which functions in the same or similar manner as native CR6 protein or which has the same or similar characteristics of the native CR6 protein. Such a peptide can include at least 1, 2, 3, or 5, and preferably 10, 20, and 30, amino acid residues from residues 1–159 of SEQ ID NO:12.

In yet other preferred embodiments, the CR6 polypeptide is a recombinant fusion protein which includes a second polypeptide portion, e.g., a second polypeptide having an amino acid sequence unrelated to a protein represented by SEQ ID NO:12, e.g., the second polypeptide portion is glutathione-S-transferase, e.g., the second polypeptide portion is a DNA binding domain, e.g., the second polypeptide portion is a polymerase activating domain, e.g. the fusion protein is functional in a two-hybrid assay.

Yet another aspect of the present invention concerns an immunogen comprising a CR6 polypeptide in an immunogenic preparation, the immunogen being capable of eliciting an immune response specific for the CR6 polypeptide; e.g. a humoral response, e.g. an antibody response; e.g. a cellular response. In preferred embodiments, the immunogen comprises an antigenic determinant, e.g. a unique determinant, from a protein represented by SEQ ID NO:12. A further aspect of the present invention features an antibody preparation specifically reactive with an epitope of the CR6 immunogen.

Another aspect of the present invention provides a substantially pure nucleic acid having a nucleotide sequence which encodes a CR6 polypeptide. In preferred embodiments: the encoded polypeptide has at least one biological activity; the encoded polypeptide has an amino acid sequence at least 60%, 80%, 90% or 95% homologous to the amino acid sequence in SEQ ID NO:12; the encoded polypeptide has an amino acid sequence essentially the same as the amino acid sequence in SEQ ID NO:12; the encoded polypeptide is at least 5, 10, 20, 50, 100, or 150 amino acids in length; the encoded polypeptide comprises at least 5, preferably at least 10, more preferably at least 20, more preferably at least 50, 100, or 150 contiguous amino acids from SEQ ID NO:12.

In a preferred embodiment, the encoded polypeptide having at least one biological activity of the CR6 polypeptide may differ in amino acid sequence from the sequence in SEQ ID NO:12, but such differences result in a modified polypeptide which functions in the same or similar manner as the native CR6 protein or which has the same or similar characteristics of the native CR6 protein.

In yet other preferred embodiments, the encoded CR6 polypeptide is a recombinant fusion protein which includes a second polypeptide portion, e.g., a second polypeptide having an amino acid sequence unrelated to a protein represented by SEQ ID NO:12, e.g., the second polypeptide portion is glutathione-S-transferase, e.g., the second polypeptide portion is a DNA binding domain, e.g., the second polypeptide portion is a polymerase activating domain, e.g., the fusion protein is functional in a two-hybrid assay.

Furthermore, in certain preferred embodiments, the subject CR6 nucleic acid includes a transcriptional regulatory sequence, e.g. at least one of a transcriptional promoter or transcriptional enhancer sequence, operably linked to the CR6 gene sequence, e.g., to render the CR6 gene sequence suitable for use as an expression vector.

In yet a further preferred embodiment, the nucleic acid which encodes an CR6 polypeptide of the invention hybridizes under stringent conditions to a nucleic acid probe corresponding to at least 12 consecutive nucleotides of SEQ ID NO:11; more preferably to at least 20 consecutive nucleotides of SEQ ID NO:11; more preferably to at least 40 consecutive nucleotides of SEQ ID NO:11. In yet a further preferred embodiment, the CR6 encoding nucleic acid hybridizes to a nucleic acid probe corresponding to a subsequence encoding at least 4 consecutive amino acids, more preferably at least 10 consecutive amino acid residues, and even more preferably at least 20 amino acid residues between residues 1–159 of SEQ ID NO:12.

In preferred embodiments: the nucleic acid sequence includes at least 1, 2, 3 or 5, and preferably at least 10, 20, 50, or 100 nucleotides from the region of SEQ ID NO:11 which encodes amino acid residues 1–159 of SEQ ID NO:12; the encoded peptide includes at least 1, 2, 3, 5, 10, 20, or 30 amino acid residues from amino acid residues 1–159 of SEQ ID NO:12.

The present invention still further pertains to a CR8 polypeptide, preferably a substantially pure preparation of a CR8 polypeptide, or a recombinant CR8 polypeptide. In preferred embodiments, the CR8 polypeptide has an amino acid sequence at least 60%, 80%, 90% or 95% homologous to the amino acid sequence in SEQ ID NO:14; the polypeptide has an amino acid sequence essentially the same as the amino acid sequence in SEQ ID NO:14; the polypeptide is at least 5, 10, 20, 50, 100, or 150 amino acids in length; the polypeptide comprises at least 5, preferably at least 10, more preferably at least 20, more preferably at least 50, 100, or 150 contiguous amino acids from SEQ ID NO:14. In further preferred embodiments, a protein homologous to SEQ ID NO:14 has a molecular weight of about 45 kilodaltons (kD), e.g. in the range of 35–50 kD.

In a preferred embodiment, a polypeptide having at least one biological activity of the CR8 polypeptide may differ in amino acid sequence from the sequence in SEQ ID NO:14, but such differences result in a modified polypeptide which functions in the same or similar manner as native CR8 protein or which has the same or similar characteristics of the native CR8 protein. Such a peptide can include at least 1, 2, 3, or 5, and preferably 10, 20, and 30, amino acid residues from residues 1–412 of SEQ ID NO:14.

In yet other preferred embodiments, the CR8 polypeptide is a recombinant fusion protein which includes a second polypeptide portion, e.g., a second polypeptide having an amino acid sequence unrelated to a protein represented by SEQ ID NO:14, e.g., the second polypeptide portion is glutathione-S-transferase, e.g., the second polypeptide portion is a DNA binding domain, e.g., the second polypeptide portion is a polymerase activating domain, e.g., the fusion protein is functional in a two-hybrid assay.

Yet another aspect of the present invention pertains to an immunogen comprising a CR8 polypeptide in an immunogenic preparation, the immunogen being capable of eliciting an immune response specific for said CR8 polypeptide; e.g. a humoral response, e.g. an antibody response; e.g. a cellular response. In preferred embodiments, the immunogen comprises an antigenic determinant, e.g. a unique determinant, from a protein represented by SEQ ID NO:14. A further aspect of the present invention features an antibody preparation specifically reactive with an epitope of the CR8 immunogen.

Another aspect of the present invention provides a substantially pure nucleic acid having a nucleotide sequence which encodes a CR8 polypeptide. In preferred embodiments: the encoded polypeptide has at least one biological activity; the encoded polypeptide has an amino acid sequence at least 60%, 80%, 90% or 95% homologous to the amino acid sequence in SEQ ID NO:14; the encoded polypeptide has an amino acid sequence essentially the same as the amino acid sequence in SEQ ID NO:14; the encoded polypeptide is at least 5, 10, 20, 50, 100, or 150 amino acids in length; the encoded polypeptide comprises at least 5, preferably at least 10, more preferably at least 20, more preferably at least 50, 100, or 150 contiguous amino acids from SEQ ID NO:14.

In a preferred embodiment, the encoded polypeptide having at least one biological activity of the CR8 polypeptide may differ in amino acid sequence from the sequence in SEQ ID NO:14, but such differences result in a modified polypeptide which functions in the same or similar manner as the native CR8 protein or which has the same or similar characteristics of the native CR8 protein.

In yet other preferred embodiments, the encoded CR8 polypeptide is a recombinant fusion protein which includes a second polypeptide portion, e.g., a second polypeptide having an amino acid sequence unrelated to a protein represented by SEQ ID NO:14, e.g., the second polypeptide portion is glutathione-S-transferase, e.g., the second polypeptide portion is a DNA binding domain, e.g., the second polypeptide portion is a polymerase activating domain, e.g. the fusion protein is functional in a two-hybrid assay.

Furthermore, in certain preferred embodiments, the subject CR8 nucleic acid includes a transcriptional regulatory sequence, e.g., at least one of a transcriptional promoter or transcriptional enhancer sequence, operably linked to the CR8 gene sequence, e.g., to render the CR8 gene sequence suitable for use as an expression vector.

In yet a further preferred embodiment, the nucleic acid which encodes a CR8 polypeptide of the invention hybridizes under stringent conditions to a nucleic acid probe corresponding to at least 12 consecutive nucleotides of SEQ ID NO:13; more preferably to at least 20 consecutive nucleotides of SEQ ID NO:13; more preferably to at least 40 consecutive nucleotides of SEQ ID NO:13. In yet a further preferred embodiment, the CR8 encoding nucleic acid hybridizes to a nucleic acid probe corresponding to a subsequence encoding at least 4 consecutive amino acids, more preferably at least 10 consecutive amino acid residues, and even more preferably at least 20 amino acid residues between residues 1–412 of SEQ ID NO:14.

In preferred embodiments: the nucleic acid sequence includes at least 1, 2, 3 or 5, and preferably at least 10, 20, 50, or 100 nucleotides from the region of SEQ ID NO:13 which encodes amino acid residues 1–412 of SEQ ID NO:14; the encoded peptide includes at least 1, 2, 3, 5, 10, 20, or 30 amino acid residues from amino acid residues 1–412 of SEQ ID NO:14.

DETAILED DESCRIPTION OF THE INVENTION

Figure 1:
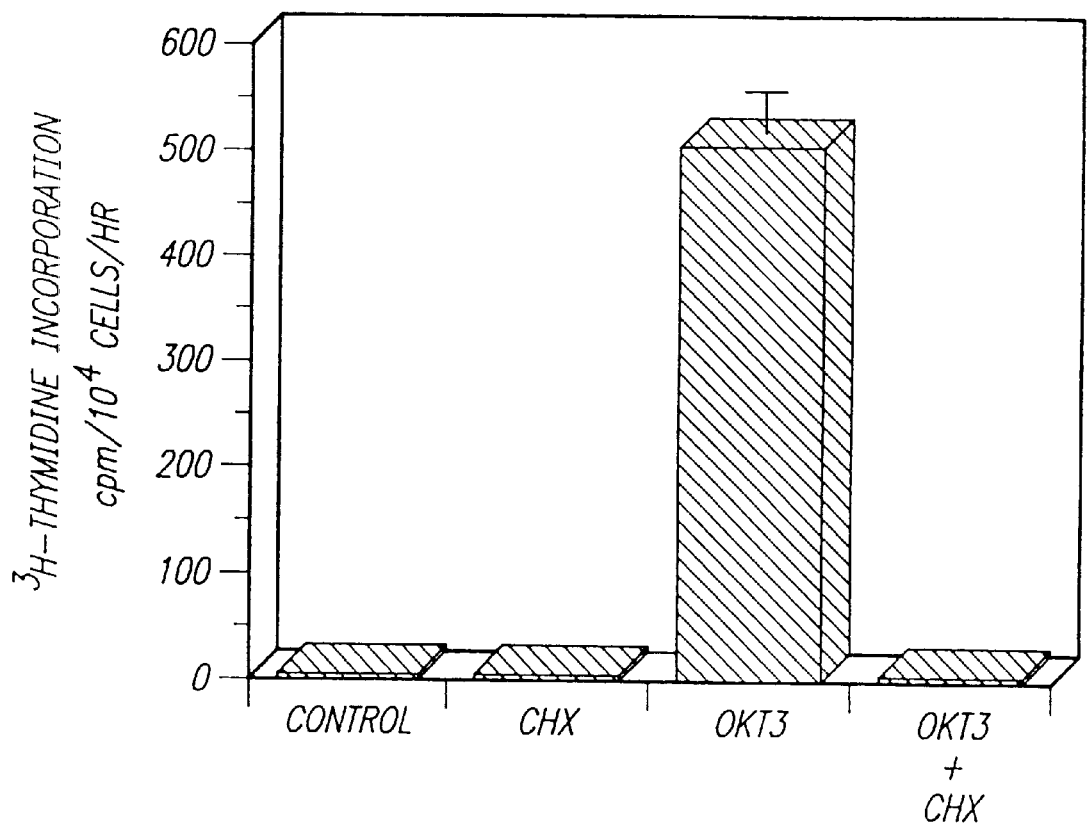
FIG. 1 a histogram showing the level of DNA synthesis (as the incorporation of [$^3$H]-thymidine in PBMN cells treated with CHX, OKT3 or OKT3 and CHX.

By combining several different procedures, a cDNA library can be constructed which is enriched in clones containing genes whose expression is induced by activation of a cellular ligand-specific receptor. This enriched library can facilitate identification and characterization of ligand-activated genes that are triggered immediately and/or early on after receptor activation (e.g., 2 to 4 hours after the ligand binds to its receptor). Such genes may play a role in stimulating growth phase transitions and subsequent clonal expansion of a particular cell type.

The method of the invention can be used to create cDNA libraries of the genes induced by activation of a variety of different cellular receptors. The receptors can be cytoplasmic, nuclear, or cell-surface receptors, and include receptors for cytokines, hormones, factors, and peptides. For example, cytokines such as the interleukins (e.g., IL-1 and IL-2), cellular growth factors (e.g., platelet-derived growth factor (PDGF), epidermal growth factor (EGF), fibroblast growth factor (FGF), insulin-like growth factor (IGF)), colony stimulating factors (e.g., multiplication stimulating activity), and hormones (e.g., insulin, somatomedin C, and steroid hormones are useful as activators of certain cellular receptors.

The ligand used to activate the receptor can be the natural ligand recognized by the receptor or a synthetic analog. Alternatively, an antibody specific for the receptor and capable of activating the receptor can be used.

The receptor is activated by a ligand or other activation for a predetermined length of time and at a concentration necessary to activate the receptor. This activation is carried out in the presence of labelled RNA precursors which are incorporated into the RNA synthesized by the cell in response to receptor activation. Thus, the RNA transcribed is labelled so as to be distinguished from preexisting RNA which is not labelled.

Some labels (such as radiolabels) can be employed to monitor the newly synthesized RNA. Useful radiolabelled RNA precursors for such purposes include [$^3$H]-uridine. Other labels may be used to separate newly transcribed RNA from unlabelled RNA. For example, RNA synthesized from thiol-labelled RNA precursors specifically adheres to phenylmercury agarose (Woodford et al. (1988) *Anal. Biochem.* 1781:166–172). RNA newly synthesized in response to receptor activation can be separated from preexisting RNA in the cell; all RNA molecules expressed prior to ligand-activation pass through the phenylmethyl mercury column, leaving only the newly synthesized, thiol-(SH-) labelled RNA attached to the agarose via a covalent bond between the mercury and sulfur. The thiol-labelled RNA molecules are then eluted from the column by reducing the Hg-S bond with an excess of 2-mercaptoethanol.

To augment the expression of immediate/early ligand-activated genes which may be difficult to identify because of the large number of downstream genes turned on at a later time, a substance that enhances the level of RNA is added to the culture medium during the ligand stimulation (see, e.g., Cochran et al. (1983) *Cell* 33:939–947). Useful substances include those compounds that stabilize RNA and/or that block translation, thereby blocking feedback inhibition of these genes by a later gene product. Such activity may potentiate the magnitude of the RNA expressed as well as the duration of the life of the RNA. Examples of such useful substances include cyclohexamide (CHX), which inhibits protein synthesis at the level of RNA-ribosome complexing and may stabilize polysomal RNA, and puromycin, which inhibits translation by causing premature dissociation of the peptide-mRNA-ribosome complex.

cAMP is another useful substance which enhances the level of RNA. Increased levels of cAMP, or analogs or agents that elevate cAMP levels, such as forskolin, dibutyryl AMP, and isobutylmethyl xanthene, are known to inhibit cell growth, proliferation, and inositol phospholipid turnover. In addition, elevated levels of cAMP completely inhibit IL-2-stimulated T-cell proliferation (Johnson et al. (1988) *Proc. Natl. Acad. Sci.* (USA) 85:6072–6076).

The labelled RNA transcribed consequent to receptor activation in the presence of the substance which enhances RNA levels is then purified from the cytoplasm of the cells. Purification can be accomplished by extracting total cellular RNA from a cell homogenate or fraction thereof, isolating mRNA therefrom, for example, using a poly U or poly[dT] column, and then separating the labelled RNA from the unlabelled RNA. Separation can be accomplished, for example, using the phenylmethyl mercury agarose protocol described above. Of course, other known methods of separating the newly synthesized RNA from the preexisting can also be used.

The cDNA libraries can be prepared from the separated labelled RNA by standard techniques. For example, the labelled RNA may be reversed transcribed into cDNA, using oligo[dT] primers. The cDNA is then ligated into appropriate vectors using established recombinant DNA techniques. A cDNA library is then constructed by methods well known in the art in prokaryotic or eukaryotic host cells that are capable of being transfected by the vectors.

Prokaryotic systems most commonly utilize *E. coli* as host, although other bacterial strains such as Bacillus, Pseudomonas, or other Gram-positive or Gram-negative prokaryotes can also be used. When such prokaryotic hosts are employed, operable control systems compatible with these hosts are ligated to the cDNA fragments and disposed on a suitable transfer vector which is capable of replication in the bacterial host cell. Backbone vectors capable of replication include phage vectors and plasmid vectors, as is known in the art. Common plasmid vectors include those derived from pBR322 and the pUC series. One such useful vector which is commercially available is the plasmid pBluescriptTIISK+(Stratagene, La Jolla, Calif.). Charon lambda phage is a frequently employed phage vector. Control sequences obligatorily include promoter and ribosome binding site encoding sequences, and a variety of such controls are available in the art, such as the beta-lactamase (pencillinase) and lactose (lac) promoter systems (see, e.g., Chang et al. (1977) *Nature* 198:106), and the tryptophan (trp) promoter systems (Goeddel et al. (1980) *Nucleic Acids Res.* 8:4057). Composite promoters containing elements of both the trp and lac promoter systems are also available in the art.

Eukaryotic microbes, such as laboratory strains of *Saccharomyces cerevisiae*, or Baker's yeast, can also be used for expression. A number of yeast control systems and vectors are available, including those which are promoters for the synthesis of glycolytic enzymes (see, e.g., Hess et al. (1968) *Biochem.* 17:4900). Yeast vectors employing the 2 micron origin of replication are suitable as transfer vectors (see, e.g., Broach (1982) *Meth. Enzym.* 101:307).

Tissue cultures of insect cell lines, or cell lines immortalized from mammalian or other higher organisms have also been used as recombinant hosts. Such cell lines include chinese hamster ovary (CHO), Vero, HeLa, and COS cells. In general, the COS cell system is used for transient expression, while CHO cells typically integrate transformed DNA into the chromosome. Suitable mammalian vectors are generally based on viral origins of replication and control sequences. Most commonly used are the simian virus 40 (SV40) promoters and replicons (see Fiers et al. (1978) *Nature* 273:113) and similar systems derived from Adenovirus 2, bovine papilloma virus, and avian sarcoma virus.

The ligand-activated genes are then screened in the library using any one of several different methods. One method involves differential hybridization with cDNA probes constructed from mRNA derived from ligand-activated cells and unactivated cells. Another method includes hybridization subtraction, whereby cDNA from ligand-activated cells is hybridized with an excess of mRNA from unactivated cells to remove RNA molecules common to both. Alternatively, cDNA probes can be made from the same pool of thiol-selected mRNA used to make the cDNA library, as these sequences are highly enriched for ligand-induced molecules.

One can prepare cDNA probes from mRNA extracted from cells treated with drugs that block the biologic response to the particular cytokine (e.g., rapamycin blocks the proliferative response of T cells to IL-2, and cyclosporin A and FK506 block the T-cell response to activation via the T-cell antigen receptor). Results from probing with the cDNA made from drug-inhibited cells can then be compared to results from probes made from cells not inhibited by these drugs.

The marked superinduction observed for a number of the genes using a substance, such as CHX, which enhances RNA levels is crucial in enabling their detection by differential hybridization, as it has been estimated that differential hybridization is only effective in the detection of relatively high-abundance RNAs expressed at a level of greater than 500 copies per cell. Therefore, the superinduction increases that level of expression of low-abundance RNAs above the threshold of detection by differential screening. In addition, the approximately 10-fold enrichment for newly synthesized RNA afforded by the thiol-labelling procedure further heightens the efficacy of the cloning procedure. Thus, the combination of superinduction and thiol-labelling of RNA significantly enhances the sensitivity of differential screening, and provides a cloning strategy which has the capacity to detect messages normally present in relatively low abundance (i.e., less than 100 copies/cell).

After the initial screening of the cDNA library, all clones isolated as tentatively positive must be corroborated as truly ligand-activated. This can be accomplished by isolating the cDNA insert from each cloned plasmid, and then employing this cDNA to probe RNA from ligand-activated cells by Northern blot analysis.

Then, to identify each gene, the cDNA can be subjected to sequence analysis. Searches of the GenBank (Los Alamos, N. Mex.) and EMBL (Heidleberg, Germany) data bases can be made of even partial sequences to identify known sequences such as pim-1, a previously characterized, IL-2 induced gene.

A number of methods can be used to characterize the novel ligand-enhanced genes and begin to determine their functional roles in, for example, signal transduction. DNA sequence analysis of the cDNA of the mRNA transcript can predict the coding region for the gene product and the amino acid sequence. From the amino acid sequence, the gene product can be placed into one of several categories of proteins, such as DNA-binding proteins, kinases, phosphatases, transmembrane proteins, or secreted products. These categories then will predict certain obvious functions and characteristics to be examined.

For example, the mechanism whereby IL-2 binding to its heterodimeric p55/p75 receptor on the cell surface activates specific gene expression is not well understood. The 75 kD component of the IL-2 receptor, which is responsible for signal transduction, does not exhibit sequence homologies indicative of previously characterized functional domains. However, the involvement of protein phosphorylation in the IL-2 response has been indicated by the activation of IL-2R-associated kinases, including the tyrosine kinase p56$^{lck}$, as well as the cytoplasmic serine/threonine kinase c-raf-1 in early IL-2-mediated transmembrane signalling. In addition, a number of proteins, including the IL-2R p75, are rapidly phosphorylated in response to IL-2. The hydrolysis of phosphatidylinositol glycan is also stimulated by IL-2, resulting in the formation of the putative second messengers myristylated diacylglycerol and inositol phosphate-glycan. Analysis of the regulatory elements governing expression of the immediate-early genes described in the present study will be useful in the further characterization of the secondary biochemical messengers activated by the IL-2-receptor.

Other methods helpful in determining the functional relevance of the IL-2induced genes include examining T-cells for their expression in response to triggering of other receptors.

One such receptor is the T-cell antigen receptor. Seminal studies of the T-cell system have demonstrated that T-cell activation occurs as a two-step process. Quiescent cells are initially stimulated through engagement of the antigen receptor, which provides the cells with the capacity to produce and respond to IL-2. Subsequently, the interaction of IL-2 with its cell-surface receptor drives progression through the $G_1$ to the S phase of the cell cycle. Transmembrane signalling through both the T-cell antigen receptor has been shown to trigger the heightened expression of a number of genes, including c-fos, c-myc and c-raf-1 (Reed et al. (1986) *Proc. Nat. Acad. Sci. USA* 83:3982–3986; Dautry et al. (1988) *J. Biol Chem.* 263:17615–17620; and Zmuidzinas et al. (1991) *Mol. Cell. Biol.* 11 :2794–2803). By comparison, in the case of the c-myb gene, the induction is unique to the IL-2 signalling pathway (Stern et al. (1986) *Science* 233:203–206). Therefore, to categorize the novel IL-2-induced genes with regard to their patterns of induction by these two receptor pathways, the sensitivity of the genes to T-cell receptor stimulation can be determined.

Additional methods that can be used to categorize the genes isolated include screening for expression by proliferating versus non-proliferating cells, for tissue-specific expression, and for expression in response to different cytokines and hormones. Genes that are expressed exclusively by proliferating cells are obvious candidates for functioning to promote cell growth. Other genes may be important for signaling differentiation and would be expected to be tissue-specific or activated only by a restricted family of similar ligands.

An additional means of elucidating the mechanisms of IL-2-mediated transmembrane signalling is provided by the varied effects of elevated cAMP on IL-2-induced gene expression. The diverse responses of the genes to cAMP suggest that the IL-2 signalling pathways responsible for their induction must bifurcate at a point prior to intersection with the cAMP regulated pathways. One potential mechanism of cAMP action may involve regulation of protein phosphorylation, as cAMP is an activator of protein kinase A, and elevations of intracellular cAMP inhibit IL-2-inducted phosphorylation events. In addition, as cAMP blocks IL-2-stimulated cell cycle progression at a point in early $G_1$, cAMP sensitivity is a useful tool with which to dissect IL-2-mediated signal transduction pathways involved in cell cycle progression.

A likely function of the immediate/early gene products is the governing of subsequent DNA replication and cell division. Previously characterized IL-2 induced genes encode kinases (c-raf-1, pim-1) and DNA binding proteins (c-fos, c-myc, c-myb). Further sequence analysis of the novel genes will determine whether the proteins they encode contain conserved domains which would implicate similar functions. However, since IL-2 stimulates cellular differentiation as well as division, and has been shown to induce the expression of a number of genes which do not per se perform a direct role in cell cycle progression, a functional correlation between the expression of the novel genes and cell cycle transit should be demonstration.

Indirectly, cAMP sensitivity is suggestive of involvement in $G_1$ progression. The demonstration of induction of the genes by other growth factors, as well as heightened expression in transformed cell lines would further support this notion. A more direct approach, utilizing antisense oligonucleotides, will make it possible to determine whether specific blockage of expression of any of these genes is sufficient to prevent cell cycle progression. Similarly, it will be possible to determine whether the immediate early gene products exert cell cycle control through the induction of expression of late genes, as has been demonstrated for regulation of the PCNA/cyclin, DNA polymerase A and cdc2 genes by the c-myb and c-myc gene products. Interestingly, the IL-2-induced expression of the PCNA/cyclin and DNA topoisomerase II gene in late $G_1$ is specifically inhibited by cAMP, so that cAMP sensitivity of immediate early gene expression can provide a useful indicator of which genes play a role in regulating late gene expression. If, like the previously characterized cell cycle regulatory cdc2/CDC28 and cyclin genes, the novel IL-2 induced genes are highly conserved, then it may ultimately be possible to isolate yeast homologs of the clones and perform deletional analyses to further define the functions of the gene products.

Ultimately, the definitive assignment of a given gene product to a particular function within a cell depends upon a series of different approaches, including determining intracellular location, and determining the consequences of blocking the expression of the gene either by mRNA antisense methods or by homologous recombination methods. All of the methods necessary for these studies exist as prior art and therefore, given the identification of a given gene as activated by a ligand such as the cytokine IL-2 is possible to characterize each gene product.

By following the method of the invention, eight clones containing ligand-induced genes have been identified. At least six of these ligand-induced genes are novel and have been named Cytokine Response (CR) genes 1–3, 5, 6 and 8. CR4 is identical to a gene reported as SATB-1 (Dickinson, L. A. et al. (1992) *Cell* 70:631–645), for Special AT-rich Binding protein 1, which binds selectively to the nuclear matrix/scaffold-associating region of DNA. CR7 is identical to the putative proto-oncogene, pim 1, a known IL-2-induced gene. The nucleic acid sequences of these CR genes, i.e., CR genes 1–6 and 8, are set forth in SEQ ID NOs:1, 3, 5, 7, 9, 11, and 13 (these sequences are also shown in FIGS. 1–7). The amino acid sequences encoded by these CR genes are set forth in SEQ ID NOs.:2, 4, 6, 8, 10, 12, and 14 (these sequences are also shown in FIGS. 1–7) as well as in SEQ ID NOs:1, 3, 5, 7, 9, 11, and 13. Table I provides several characteristics of the CR genes.

TABLE I

CR GENE CHARACTERISTICS

| CR Gene | Protein Size (kDa) | Homology (Identity) | IL-2 Induction (x) | cAMP Effect (±) |
|---|---|---|---|---|
| 1 | 22.2 | $G_0S8$, B134 | 24 | − |
| 2 | 6.6 | — | 7 | − |
| 3 | 88.0 | Prostaglandin R | 22 | − |
| 4 | 83.9 | (SATB1) | 6 | + |
| 5 | 28.4 | SH2 | 50 | − |
| 6 | 17.5 | GADD45, MyD118 | 5 | − |
| 7 | 34.4 | (pim) | 17 | − |
| 8 | 45.3 | bHLH | 7 | + |

The regulatory region of all of the CR genes can be used to construct assays to identify the relevant cis-acting DNA response elements, the trans-acting factors responsible for transcriptional activation leading to CR gene expression, and the biochemical signalling for pathways triggered by IL-2 (the ligand) that activate the transcriptional activating factors. These assays can be used to identify novel agents or drugs that either suppress or activate CR gene expression. Such novel agents or drugs can be used immunosuppressives, immunostimulants, or anti-cancer agents.

The immediate-early CR genes and gene products can be used to construct assays to determine which biochemical and molecular events, initiated by the ligand-receptor stimulation, promote progression to the intermediate and late stages of cell cycle progression that are responsible for DNA synthesis and replication. These assays can be used to identify novel agents and drugs that either suppress or promote these processes. With the capacity to generate large quantities of the CR gene products, the three-dimensional structures of the products can be determined by conventional methods, such as x-ray crystallography and nuclear magnetic resonance. From this information, novel agents or drugs can be identified using computer analysis of the chemical structures, that interact with the CR gene product. These agents can then be developed as therapeutics.

The regulation of CR1 expression is notable in that it is rapidly and transiently induced by IL-2, and mRNA expression is suppressed by elevated intracellular cAMP, which also suppresses IL-2-promoted $G_1$ progression. There are already available pharmaceuticals that elevate intracellular cAMP, such as aminophylline and theophylline. Therefore, it is now possible to determine how these agents function to inhibit CR1 expression and to identify novel agents that act similarly, but may have particular pharmacologic advantages.

The CR1 gene includes 2406 nucleotides (shown in SEQ ID NO:1 and FIG. 1) and encodes a protein of 202 amino acids (about 22 kDa) (shown in SEQ ID NO:2 and FIG. 1) that shares sequence homology to two other recently reported genes, GOS8 and BL-34, both of which are induced to high levels of expression by mitogens. The nucleotide sequence of the CR1 gene is about 58% homologous to the nucleotide sequence of the GOS8 gene (Siderovski, D. P. et al. (1994) *DNA and Cell Biology* 13:125–147), which was isolated from a PHA-induced T cell library. At the protein level, CR1 is about 51.2% homologous to GOS8. In addition, the nucleotide sequence of the CR1 gene is about 58% homologous to the nucleotide sequence of the BL34 gene (Hong, J. X. et al. (1993) *J. Immunol.* 150:3895–3904), which was isolated from a Staph A-activated B cell cDNA library. At the protein level, CR1 is about 48.0% homologous to BL34. The homology of CR1 with BL-34 is of particular interest, in that BL-34 is expressed only by activated B cells, is preferentially expressed in vivo by B cells in lymph node germinal centers, and is overexpressed in B cell malignancies. As predicted from its amino acid sequence which contains neither a hydrophobic leader sequence nor a transmembrane region, CR1 is an intracellular protein. Also, the CR1 protein includes no sequences consistent with other known functional motifs or domains, such as found for DNA binding proteins, kinases, phosphatases, or linker molecules. The sequences for the gene (SEQ. ID No:1), protein (SEQ. ID No:2), and protein coding region of the gene (SEQ. ID No:27) for CR1, the underlined being the protein coding region of the gene, are provided below in Table II.

Figure 2:
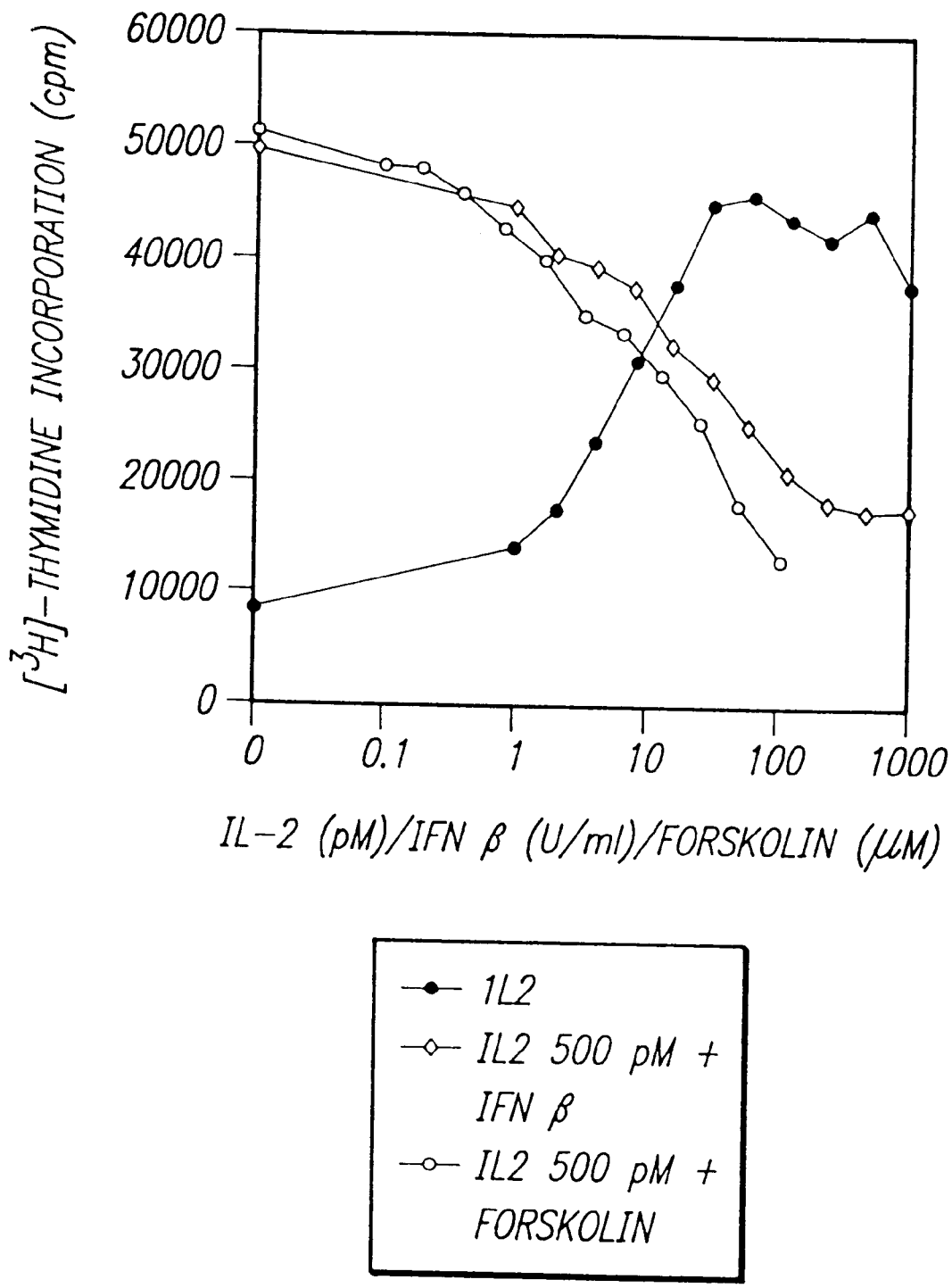
FIG. 2 shows CR8 expression in the following cytokine-dependent cell lines: the IL-2-dependent human T cell line Kit 225; the IL-3-dependent mouse pro-B cell line Ba/F3; and the IL-2-dependent mouse T cell line CTLL2.

The CR2 gene includes 1283 nucleotides (shown in SEQ ID NO:3 and FIG. 2) and encodes a small, intracellular protein of 60 amino acids (about 6.6 kDa)(shown in SEQ ID NO:4 and FIG. 2). The CR2 gene is the only CR gene for which there are no homologies to known gene products. Elevated cAMP suppresses, but does not abolish CR2 gene expression. The sequences for the gene (SEQ. ID No:3), protein (SEQ. ID No:4), and protein coding region of the gene (SEQ. ID No:28) for CR2, the underlined being the protein coding region of the gene (SEQ. ID No:28), are provided below in Table III.

The CR3 gene includes 2451 nucleotides (shown in SEQ ID NO:5 and FIG. 3) and encodes a protein of 378 amino acids (about 41.5 kDa) (shown in SEQ ID NO:6 and FIG. 3). This protein is homologous to G-coupled, 7 transmembrane-spanning receptors of the prostaglandin family. The receptor for prostacyclin ($PGI_2$) is most homologous (about 70%) (See Boie, Y. et al. (1994) *J. Biol. Chem.* 269:12173–12178) to the CR3 protein. $PGI_2$ is a labile metabolite of arachidonic acid produced via the cyclooxygenase pathway, and plays a major physiological role as a potent mediator of vasodilation and inhibitor of platelet activation. It is primarily expressed in the kidney with lower levels of mRNA also observed in the lung and the liver. In the kidney the $PGI_2$ receptor is thought to play an important role in renal blood flow, renin release, and glomerular filtration rate. By comparison, CR3 is maximally expressed by leukocytes, placenta, testes, ovary and small intestine, and at lower levels by spleen, thymus and prostate, but not by kidney or liver. Therefore, CR3 most likely plays a regulatory role in cellular proliferation and/or inflammation. Elevated cAMP suppresses CR3 expression early on after IL-2 stimulation, but not at later time intervals.

Because the CR3 encodes a protein that is a member of a family of 7 transmembrane spanning receptors, it is likely that this receptor is coupled to cytoplasmic GTP-binding proteins (G proteins) that are known to activate or suppress the generation of cAMP. Therefore, the CR3 gene product provides a new receptor that can allow the manipulation of cellular functions that are controlled by biochemical pathways signaled by the receptor. The CR3 gene and gene product can be used in assays for identifying ligands that trigger the receptor. These ligands can be used to modulate cellular proliferation and inflammation. The sequences for the gene (SEQ. ID No:5), protein (SEQ. ID No:6), and protein coding region of the gene (SEQ. ID No:29) corresponding to CR3, the underlined being the protein coding region of the gene (SEQ. ID No:29), are shown in Table IV below.

The CR4 gene includes 2946 nucleotides (shown in SEQ ID NO:7 and FIG. 4) and encodes a protein of 763 amino acids (about 85.9 kDa) (shown in SEQ ID NO:8 and FIG. 4). The sequence of this gene is identical to a gene reported as SATB-1 (Dickinson, L. A. et al. (1992) *Cell* 70:631–645), for Special AT-rich Binding protein 1, which binds selectively to the nuclear matrix/scaffold-associating region of DNA. It is expressed exclusively in the thymus and activated peripheral T cells. CR4 is the only CR gene also activated by the TCR. In addition, elevated cAMP actually stimulates CR4 gene expression.

Because the CR4 gene product binds to special AT-rich regions of DNA known to associate with proteins in the nuclear mating, CR4 is most likely a novel nuclear matrix protein. The nuclear matrix proteins are known to influence the structure of DNA, facilitating transcription of specific genes in particular differentiated tissues. Because the expression of CR4 is restricted to thymocytes and activated T cells, it is likely that CR4 plays an important role in T cell maturation, differentiation or proliferation. Therefore, novel agents that modify CR4 gene expression or CR4 function have the potential to be useful to manipulate the T cell immune response. Thus, CR4 can be used in an assay to identify such novel agents which can be used, for example, to treat transplant recipients by, for example, inhibiting the recipient's T cell immune response. These agents can also be used to stimulate the T cell immune response in immuno-suppressed subjects, e.g., AIDS patients. The sequences for the gene (SEQ. ID No:7), protein (SEQ. ID No:8), and protein coding region of the gene (SEQ. ID No:30) for CR4, the underlined being the protein coding region of the gene, are shown in Table V below.

The CR5 gene includes 2020 nucleotides (shown in SEQ ID NO:9 and FIG. 5) and encodes a protein of 258 amino acids (about 28kDa) (shown in SEQ ID NO:10 and FIG. 5). In the middle of the open reading frame of the CR5 protein is about a 100 amino acid region that has sequence homology (about 25–35%) to src homology 2 (SH2) domains (Waksman, G. et al. (1993) *Cell* 72:779–790), found in many proteins that bind to phosphotyrosine residues, e.g., kinases, substrates, linking molecules, and transcription factors. On either side of this SH2 domain the amino acid sequence is very rich in proline residues. Analysis of CR5 protein expression by different tissues reveals a high level of expression in heart, placenta, lung, liver skeletal muscle and kidney. CR5 protein expression is induced by the proliferation-promoting cytokines IL-2, IL-3, IL-4, IL-5, but not by IL-6. Also, CR5 protein expression is induced by IFN-β and elevated intracellular cAMP, both of which antagonize IL-2 promoted proliferation. CR5 protein has been found to interact with a subunit of the RNA polymerase II preinitiation complex, termed RNA polymerase II elongation factor SIII, p15 subunit. Garret, K. P. et al. (1994) *Proc. Natl. Acad. Sci. USA* 91:5237–5241. The p15 subunit of this RNA polymerase II elongation factor is known to be responsible for promoting the elongation of transcripted mRNA molecules. Therefore, CR5 appears to function as a ligand-stimulated factor that facilitates mRNA expression by promoting the full elongation of mRNA transcripts. This phenomenon promises to be a novel way in which ligand-receptor systems can regularly promote gene expression. Previously, attention has focused almost entirely on this initiation of transcription, not the elongation of transcripts that were prematurely truncated. Accordingly, novel agents or drugs that modify CR5 gene expression or CR5 function have the potential to provide new ways to alter ligand-stimulated gene expression and thereby alter cellular function. The sequences for the gene (SEQ. ID No:9), protein (SEQ. ID No:10), and protein coding region of the gene (SEQ. ID No:33) for CR5, the underlined being the protein coding region of the gene (SEQ. ID No:33), are shown in Table VI below.

The CR6 gene includes 1066 nucleotides (shown in SEQ ID NO:11 and FIG. 6) and encodes protein of 159 amino acids (about 17.5 kDa) (shown in SEQ ID NO:12 and FIG. 6). This gene belongs to a family of small nuclear-localizing gene products. Two other members of this family, GADD45 and MyD118, have been identified. GADD45 was cloned from human fibroblasts induced by UV irradiation (Papathanasiou, M. A. et al. (1991) *Mol. Cell Biol.* 11(2):1009–1016). This protein is regulated by p53 and suppresses growth of cells by binding to PCNA, a co-factor required for DNA polymerase 67 activity. (Smith, M. L. et al. (1994) *Science* 266:1376–1380). MyD118 was cloned from M1D+ myeloid precursors following induction of terminal differentiation and growth arrest by IL6. Abdollahi, A. et al. (1991) *Oncogene* 6:165–167. At the nucleotide level, CR6 is about 65% homologous to GADD45. At the protein level, CR6 is about 54% homologous to GADD45. At the nucleotide level, CR6 is about 66% homologous to MyD118. At the protein level, CR6 is about 53% homologous to MyD118. The CR6 protein is expressed only in testes, ovary and prostate, and its expression is suppressed by elevated cAMP.

By analogy to it's homology to GADD45 and MyD 118, the CR6 gene product most likely plays a role in DNA replication. Thus far, experiments have indicated that CR6 expression is not induced by agents that damage DNA, such as UV light. Moreover, CR6 does not bind to PCNA. However, CR6 does promote DNA replication in vitro, and it is likely to be a novel CD-factor necessary for DNA replication. Therefore, the CR6 gene product can be used to identify inhibitors of DNA replication which can be used as antiproliferative agents, e.g., in the treatment of cancer. The SEQ. ID No:11, SEQ. ID No:12, and SEQ. ID No:31, corresponding to the gene, protein and protein coding DNA sequences of CR6, the underlined corresponding to the protein coding region of the gene (SEQ. ID No:31), are shown in Table VII below.

The CR7 gene includes 2400 nucleotides and encodes a protein of 313 amino acids (about 34 kDa). The CR7 gene is identical to the putative proto-oncogene, pim-1, which has been reported to be over-expressed in about 50% of Moloney murine leukemia virus (MuLV)-induced T cell lymphomas. See Selten, G. et al. (1986) Cell 46:603–611 for the nucleotide and amino acid sequence of pim-1) Pim-1 is known to be an IL-2-induced gene and is a serine/threonine-specific protein kinase involved in T cell lymphomagenesis. The CR7 gene includes a 2400 nucleotide DNA (SEQ. ID No:25), encoding a protein of 313 amino acids (about 34 kD) of SEQ. ID No:26. The gene (SEQ. ID No:25), protein (SEQ. ID No:26), protein coding region of the gene (SEQ. ID No:35), and the DNA sequence complementary to the gene sequence (SEQ. ID No:34), the underlined being the protein coding region of the gene, are shown in Table VIII below.

The CR8 gene includes 2980 nucleotides (shown in SEQ ID NO:13 and FIG. 7) and encodes (via a 3.2 kb mRNA transcript) a protein of 412 amino acids (about 45 kDa) (shown in SEQ ID NO:14 and FIG. 7). There is significant sequence homology (40–45%) within an N-terminal 58 amino acid residue region to transcription factors that have a basic-Helix-Loop-Helix (bHLH) motif. The protein encoded by the bHLH region of the gene has been expressed in *E. coli* and has been found to bind to a hexanucleotide predicted by the binding specificity of other bHLH proteins. See Feder, J. et al. (1993) *Mol. Cell Biol.* 13(1):105–113. The N-terminal basic region binds to DNA and the HLH region serves as a protein dimerization motif. From the sequence of the bHLH region, CR8 fits into a class by itself. It shares most homology with Drosophila transcription repressors of the hairy family. However, CR8 lacks amino acid residues in the basic region and a C-terminal WRPW motif, characteristic for hairy proteins. CR8 also binds to Class B E-box sites (CACGTC/CATGTG), as do the c-myc family of bHLH proteins, rather than to Class C sites (CAGCCG) preferred by hairy-related family members. CR8 is ubiquitously expressed in all tissues examined except placenta. Its expression is induced by cytokines such as IL-2 and IL-3, which stimulate cellular proliferation, and also by IFNβ and elevated cAMP, which antagonize proliferation.

Because CR8 contains a bHLH domain, it is most likely a protein that binds to DNA and modifies gene expression, either by activation or by suppression. Since CR8 binds to class B E-bax sequences, which the proto-oncogene c-myc family members also bind, it is likely that CR8 modifies the expression of genes important for the intermediate and late phases of ligand-promoted cell cycle progression. It follows that CR8 is a prime candidate for the development of new assays to discover agents that modify cellular function by either enhancing or suppressing CR8 gene expression or CR8 function. The CR8 gene and its gene product are described in further detail below in Example VII. The CR8 gene includes a 2980 nucleotide fragment of SEQ. ID NO:13, which encodes (via a 3.2 Kb mRNA transcript) a protein of 412 amino acids (about 45 kD) of SEQ. ID NO:14. The SEQ. ID No:13, SEQ. ID No:14, and SEQ. ID No:32, corresponding to the gene, protein, and protein coding gene sequences, are shown in Table IX below.

In summary, of the eight CR genes isolated using the thiol-selected IL-2-induced cDNA library, two are DNA binding proteins, one is a newly recognized transmembrane receptor, one contains an SH2 domain, one is homologous to a newly recognized family of small proteins that regulate cellular proliferation, and another is a serine/threonine kinase already known to be IL-2-induced, and to be over-expressed in MuLV-induced T cell lymphomas. Allowing for redundancies, a conservative estimate is that there are still about 40–50 novel genes induced by IL-2 which can be isolated using the method of the present invention.

Accordingly, the present invention pertains to an isolated nucleic acid comprising the nucleotide sequence encoding one of the subject CR proteins, e.g., CR1, CR2, CR3, CR4, CR5, CR6, and CR8, and/or equivalents of such nucleic acids. The term "nucleic acid" as used herein is intended to include fragments and equivalents. The term "equivalent" as used herein refers to nucleotide sequences encoding functionally equivalent CR proteins or functionally equivalent peptides which retain other activities of an CR protein such as described herein. Equivalent nucleotide sequences include sequences that differ by one or more nucleotide substitutions, additions or deletions, such as allelic variants, and, therefore, include sequences that differ from the nucleotide sequence CR proteins shown in any of SEQ ID NOs:2, 4, 6, 8, 10, 12, and 14 due to the degeneracy of the genetic code. Equivalents also include nucleotide sequences that hybridize under stringent conditions (i.e., equivalent to about 20–27° C. below the melting temperature ($T_m$) of the DNA duplex formed in about 1M salt) to the nucleotide sequence of the presently claimed CR proteins represented in SEQ ID NOs:2, 4, 6, 8, 10, 12, and 14. In one embodiment, equivalents further include nucleic acid sequences derived from and evolutionarily related to, a nucleotide sequences shown in any of SEQ ID NOs:1, 3, 5, 7, 9, 11, and 13. Moreover, it is explicitly contemplated by the present invention that, under certain circumstances, it may be advantageous to provide homologs of the subject CR proteins which have at least one biological activity of a CR protein. Such homologs of the subject CR proteins can be generated by mutagenesis, such as by discrete point mutation(s) or by truncation. For instance, mutation can give rise to homologs which retain substantially the same, or merely a subset, of the biological activity of the CR protein from which it was derived. Alternatively, antagonistic forms of the protein can be generated which are able to inhibit the function of the naturally occurring form of the CR protein.

A protein has CR biological activity if it has one or more of the following properties: (1) its expression is regulated by ligand-receptor stimulation; and (2) it participates in ligand-receptor modification of cellular function, e.g. proliferation, differentiation, programmed cell death.

As used herein, the term "gene" or "recombinant gene" refers to a nucleic acid comprising an open reading frame encoding a CR protein of the present invention, including both exon and (optionally) intron sequences. A "recombinant gene" refers to nucleic acid encoding a CR protein and comprising CR encoding exon sequences, though it may optionally include intron sequences which are either derived from a chromosomal CR gene or from an unrelated chromosomal gene. The term "intron" refers to a DNA sequence present in a given CR gene which is not translated into protein and is generally found between exons.

As used herein, the term "transfection" means the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of the CR protein of the present invention or where antisense expression occurs from the transferred gene, the expression of a naturally-occurring form of the CR protein is disrupted.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA loops which, in their vector form are not bound to the chromosome. In the present application, "plasmid" and "vector" are used interchangeably as the plasmid is the most commonly used form of vector. However, the invention is intended to include such other forms of expression vectors which serve equivalent functions and which become known in the art subsequently hereto.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of a recombinant CR gene is under the control of a promoter sequence (or other transcriptional regulatory sequence) which controls the expression of the recombinant gene in a cell-type in which expression is intended. The recombinant gene can also be under the control of transcriptional regulatory sequences which are the same or which are different from those sequences which control transcription of the naturally-occurring form of the CR proteins.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue. The term also covers so-called "leaky" promoters, which regulate expression of a selected DNA primarily in one tissue, but cause expression in other tissues as well.

As used herein, a "transgenic animal" is any animal, preferably a non-human mammal, e.g. a rat, a mouse or pig, in which one or more of the cells of the animal includes a transgene. The transgene is introduced into the cell, directly or indirectly by introduction into a precursor of the cell, by way of deliberate genetic manipulation, such as by microinjection or by infection with a recombinant virus. The language "genetic manipulation" does not include classical cross-breeding, or in vitro fertilization, but rather is directed to the introduction of a recombinant DNA molecule. This molecule can be integrated within a chromosome, or it may be extrachromosomally replicating DNA. In the transgenic animals described herein, the transgene causes cells to express a recombinant form of one or more of the subject CR proteins, or alternatively, to disrupt expression of one or more of the naturally-occurring forms of the CR genes.

As used herein, the term "transgene" refers to a nucleic acid sequence which is partly or entirely heterologous, i.e., foreign, to the animal or cell into which it is introduced, or, is homologous to an endogenous gene of the animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

As is well known, genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding a CR protein" refers to one or more genes within a particular individual. Moreover, certain differences in nucleotide sequences may exist between individual organisms, which are called alleles. Such allelic differences may or may not result in differences in amino acid sequence of the encoded polypeptide yet still encode a protein with the same biological activity.

"Cells," "host cells" or "recombinant host cells" are terms used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric protein" or "fusion protein" is a fusion of a first amino acid sequence encoding one of the subject CR proteins with a second amino acid sequence defining a domain foreign to and not substantially homologous with any domain of the subject CR protein. A chimeric protein may present a foreign domain which is found (albeit in a different protein) in an organism which also expresses the first protein, or it may be an "interspecies", "intergeneric", etc. fusion of protein structures expressed by different kinds of organisms.

The language "evolutionarily related to", with respect to nucleic acid sequences encoding CR proteins, refers to nucleic acid sequences which have arisen naturally in an organism, including naturally occurring mutants. This language also refers to nucleic acid sequences which, while derived from a naturally occurring CR nucleic, have been altered by mutagenesis, as for example, combinatorial mutagenesis, yet still encode polypeptides which have at least one activity of a CR protein.

In one embodiment, the nucleic acid is a cDNA encoding a peptide having at least one activity of a subject CR proteins. Preferably, the nucleic acid is a cDNA molecule comprising at least a portion of the nucleotide sequence represented in one of SEQ ID NOs: 1, 3, 5, 7, 9, 11, and 13. A preferred portion of these cDNA molecules includes the coding region of the gene.

Preferred nucleic acids encode a CR protein comprising an amino acid sequence at least 60% homologous, more preferably 70% homologous and most preferably 80%, 90%, or 95% homologous with an amino acid sequence shown in one of SEQ ID NOs:2, 4, 6, 8, 10, 12, or 14. Nucleic acids which encode polypeptides having an activity of a subject CR protein and having at least about 90%, more preferably at least about 95%, and most preferably at least about 98–99% homology with a sequence shown in one of SEQ ID NOs:2, 4, 6, 8, 10, 12, or 14 are also within the scope of the invention. The term "homology" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. The degree of homology between sequences is a function of the number of matching or homologous positions shared by the sequences.

Another aspect of the invention provides a nucleic acid which hybridizes under high or low stringency conditions to a nucleic acid which encodes a peptide having all or a portion of an amino acid sequence shown in SEQ ID NO:2, SEQ ID NO:4, SEQ ID NO:6, SEQ ID NO:8, SEQ ID NO:10, SEQ ID NO:12 or SEQ ID NO:14. Appropriate stringency conditions which promote DNA hybridization, for example, 6.0× sodium chloride/sodium citrate (SSC) at about 45° C., followed by a wash of 2.0× SSC at 50° C., are known to those skilled in the art or can be found in Current Protocols in Molecular Biology, John Wiley & Sons, N.Y. (1989), 6.3.1–6.3.6. For example, the salt concentration in the wash step can be selected from a low stringency of about 2.0× SSC at 50° C. to a high stringency of about 0.2× SSC at 50° C. In addition, the temperature in the wash step can be increased from low stringency conditions at room temperature, about 22° C., to high stringency conditions at about 65° C.

Nucleic acids, having a sequence that differs from the nucleotide sequence shown in any of SEQ ID NOs:1, 3, 5, 7, 9, 11, and 13 due to degeneracy in the genetic code are also within the scope of the invention. Such nucleic acids encode functionally equivalent peptides (i.e., a peptide having a biological activity of a CR protein) but differ in sequence from the sequence shown in said sequence listings due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of the CR protein. However, it is expected that DNA sequence polymorphisms that do lead to changes in the amino acid sequences of the subject CR proteins will exist among vertebrates One skilled in the art will appreciate that these variations in one or more nucleotides (up to about 3–5% of the nucleotides) of the nucleic acids encoding polypeptides having an activity of an CR protein may exist among individuals of a given species due to natural allelic variation. Any and all such nucleotide variations and resulting amino acid polymorphisms are within the scope of this invention.

Fragments of the nucleic acids encoding the active portion of the presently claimed CR proteins are also within the scope of the invention. As used herein, a fragment of the nucleic acid encoding the active portion of a CR protein refers to a nucleic acid having fewer nucleotides than the nucleotide sequence encoding the entire amino acid sequence of a CR protein but which nevertheless encodes a peptide having a biological activity of the CR proteins described herein. Nucleic acid fragments within the scope of the present invention include those capable of hybridizing under high or low stringency conditions with nucleic acids from other species for use in screening protocols to detect CR homologs, as well as those capable of hybridizing with nucleic acids from human specimens for use in detecting the presence of a nucleic acid encoding one of the subject CR proteins, including alternate isoforms, e.g. mRNA splicing variants Nucleic acids within the scope of the invention can also contain linker sequences, modified restriction endonuclease sites and other sequences useful for molecular cloning, expression or purification of recombinant forms of the subject CR proteins.

A nucleic acid encoding a peptide having an activity of an CR protein can be obtained from mRNA present in any of a number of eukaryotic cells. Nucleic acids encoding CR proteins of the present invention can also be obtained from genomic DNA obtained from both adults and embryos. For example, a gene encoding a CR protein can be cloned from either a cDNA or a genomic library in accordance with protocols herein described, as well as those generally known to persons skilled in the art. A cDNA encoding one of the subject CR proteins can be obtained by isolating total mRNA from a cell, e.g. a mammalian cell, e.g. a human cell, including tumor cells. Double stranded cDNAs can then be prepared from the total mRNA, and subsequently inserted into a suitable plasmid or bacteriophage vector using any one of a number of known techniques. The gene encoding the CR protein can also be cloned using established polymerase chain reaction techniques in accordance with the nucleotide sequence information provided by the invention. The nucleic acid of the invention can be DNA or RNA. Preferred nucleic acids are the cDNAs represented by the sequences shown in SEQ ID NOs:1, 3, 5, 7, 9, 11, and 13.

This invention also provides expression vectors containing a nucleic acid encoding a peptide having an activity of an CR protein, operably linked to at least one transcriptional regulatory sequence. The language "operably linked" refers to linkage of the nucleotide sequence to a regulatory sequence in a manner which allows expression of the nucleotide sequence. Regulatory sequences are art-recognized and are selected to direct expression of the peptide having an activity of a CR protein. Accordingly, the language "transcriptional regulatory sequence" includes promoters, enhancers and other expression control elements. Such regulatory sequences are described in Goeddel; *Gene Expression Technology: Methods in Enzymology* 185, Academic Press, San Diego, Calif. (1990). The design of the expression vector may depend on such factors as the choice of the host cell to be transformed and/or the type of protein desired to be expressed. In one embodiment, the expression vector includes a recombinant gene encoding a peptide having an activity of a subject CR protein. Such expression vectors can be used to transfect cells and thereby produce proteins or peptides, including fusion proteins or peptides, encoded by nucleic acids as described herein. Moreover, such vectors can be used as a part of a gene therapy protocol to reconstitute the function of, or alternatively, abrogate the function of one of the subject CR proteins in a cell in which a CR protein is misexpressed.

Another aspect of the present invention concerns recombinant forms of the subject CR proteins which are encoded by genes derived from eukaryotic organisms, e.g. mammals, e.g. humans, and which have at least one biological activity of a CR protein. The term "recombinant protein" refers to a protein of the present invention which is produced by recombinant DNA techniques, wherein generally DNA encoding the subject CR protein is inserted into a suitable expression vector which is in turn used to transform a host cell to produce the heterologous protein. Moreover, the phrase "derived from", with respect to a recombinant gene encoding the recombinant CR protein, includes within the meaning of "recombinant protein" those proteins having an amino acid sequence of a native CR protein of the present invention, or an amino acid sequence similar thereto which is generated by mutations including substitutions and deletions (including truncation) of a naturally occurring CR protein of a organism. Recombinant proteins preferred by the present invention, in addition to native CR proteins, are at least 60% homologous, more preferably 70% homologous and most preferably 80% homologous with an amino acid sequence shown in one of SEQ ID NOs:2, 4, 6, 8, 10, 12, or 14. Polypeptides having an activity of the subject CR proteins and having at least about 90%, more preferably at least about 95%, and most preferably at least about 98–99% homology with a sequence of either in SEQ ID NO:2, 4, 6, 8, 10, 12, or 14 are also within the scope of the invention.

The present invention further pertains to recombinant forms of the subject CR proteins which are encoded by genes derived from an organism and which have amino acid sequences evolutionarily related to a CR protein of either SEQ ID NO:2, 4, 6, 8, 10, 12, or 14. The language "evolutionarily related to", with respect to amino acid sequences of the present recombinant CR proteins, refers to CR proteins having amino acid sequences which have arisen naturally, as well as mutational variants of CR proteins which are derived, for example, by combinatorial mutagenesis. Preferred evolutionarily derived CR proteins are at least 60% homologous, more preferably 70% homologous and most preferably 80% homologous with an amino acid sequence shown in either SEQ ID NO:2, SEQ ID NO:4, SEQ ID NO:6, SEQ ID NO:8, SEQ ID NO:10, SEQ ID NO:12 or SEQ ID NO:14. Polypeptides having at least about 90%, more preferably at least about 95%, and most preferably at least about 98–99% homology with a sequence shown in any of SEQ ID NOs:2, 4, 6, 8, 10, 12, or 14 are also within the scope of the invention.

The present invention further pertains to methods of producing the subject CR proteins. For example, a host cell transfected with a nucleic acid vector directing expression of a nucleotide sequence encoding the subject CR protein can be cultured under appropriate conditions to allow expression of the peptide to occur. The peptide can be secreted and isolated from a mixture of cells and medium containing the recombinant CR peptide. Alternatively, the peptide can be retained cytoplasmically and the cells harvested, lysed and the protein isolated. A cell culture includes host cells, media and other byproducts. Suitable media for cell culture are well known in the art. The recombinant CR peptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant CR protein is a fusion protein containing a domain which facilitates its purification.

This invention also pertains to a host cell transfected to express a recombinant form of at least one of the subject CR proteins. The host cell can be any prokaryotic or eukaryotic cell. Thus, a nucleotide sequence derived from the cloning of the CR proteins of the present invention, encoding all or a selected portion of a protein, can be used to produce a recombinant form of a CR protein via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins, e.g. insulin, interferons, human growth hormone, IL-1, IL-2, and the like. Similar procedures, or modifications thereof, can be employed to prepare recombinant CR proteins, or portions thereof, by microbial means or tissue-culture technology in accordance with the subject invention.

A recombinant CR gene can be produced by ligating nucleic acid encoding a subject CR protein, or a portion thereof, into a vector suitable for expression in either prokaryotic cells, eukaryotic cells, or both. Expression vectors for production of recombinant forms of the subject CR proteins include plasmids and other vectors. For instance, suitable vectors for the expression of a CR protein include plasmids of the types: pBR322-derived plasmids, pEMBL-derived plasmids, pEX-derived plasmids, pBTac-derived plasmids and pUC-derived plasmids for expression in prokaryotic cells, such as E. coli.

A number of vectors exist for the expression of recombinant proteins in yeast. For instance, YEP24, YIP5, YEP51, YEP52, pYES2, and YRP17 are cloning and expression vehicles useful in the introduction of genetic constructs into S. cerevisiae (see, for example, Broach et al. (1983) in *Experimental Manipulation of Gene Expression*, ed. M. Inouye Academic Press, p. 83, incorporated by reference herein). These vectors can replicate in E. coli due the presence of the pBR322 ori, and in S. cerevisiae due to the replication determinant of the yeast 2 micron plasmid. In addition, drug resistance markers such as ampicillin can be used.

The preferred mammalian expression vectors contain both prokaryotic sequences to facilitate the propagation of the vector in bacteria, and one or more eukaryotic transcription units that are expressed in eukaryotic cells, The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press: 1989) Chapters 16 and 17. In some instances, the recombinant CR protein can be expressed using a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When expression of a portion of one of the subject CR proteins is desired, i.e. a truncation mutant, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from E. coli (Ben-Bassat et al. (1987) *J. Bacteriol*. 169:751–757) and *Salmonella typhimurium* and its in vitro activity has been demonstrated on recombinant proteins (Miller et al. (1987) *PNAS* 84:2718–1722). Therefore, removal of an N-terminal methionine, if desired, can be achieved either in vivo by expressing CR-derived polypeptides in a host which produces MAP (e.g., E. coli or CM89 or S. cerevisiae), or in vitro by use of purified MAP (e.g., procedure of Miller et al., supra).

Alternatively, the coding sequences for the polypeptide can be incorporated as a part of a fusion gene including a nucleotide sequence encoding a different polypeptide. This type of expression system can be useful under conditions where it is desirable to produce an immunogenic fragment of a CR protein. The nucleic acid sequences corresponding to the portion of a subject CR protein to which antibodies are to be raised can be incorporated into a fusion gene construct which includes coding sequences for a late vaccinia virus structural protein to produce a set of recombinant viruses expressing fusion proteins comprising a portion of the CR protein as part of the virion, It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of a CR protein and the poliovirus capsid protein can be created to enhance immunogenicity of the set of polypeptide antigens (see, for example, EP Publication No: 0259149; and Evans et al. (1989) *Nature* 339:385; Huang et al. (1988) *J. Virol*. 62:3855; and Schlienger et al. (1992) *J. Virol*. 66:2).

The Multiple Antigen Peptide system for peptide-based immunization can also be utilized to generate an immunogen, wherein a desired portion of a subject CR protein is obtained directly from organo-chemical synthesis of the peptide onto an oligomeric branching lysine core (see, for example, Posnett et al. (1988) *JBC* 263:1719 and Nardelli et al. (1992) *J. Immunol*. 148:914). Antigenic determinants of the subject CR proteins can also be expressed and presented by bacterial cells.

In addition to utilizing fusion proteins to enhance immunogenicity, fusion proteins can also facilitate the expression of proteins, such as any one of the CR proteins of the present invention. For example, a CR protein of the present invention can be generated as a glutathione-S-transferase (GST- fusion protein). Such GST fusion proteins can enable easy purification of the CR protein, such as by the use of glutathione-derivatized matrices (see, for example, *Current Protocols in Molecular Biology*, eds. Ausabel et al. (N.Y.: John Wiley & Sons, 1991)).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al. John Wiley & Sons: 1992).

Another aspect of the invention pertains to isolated peptides having an activity of one of the subject CR proteins. In preferred embodiments, a biological activity of a CR protein includes: promotion of cell cycle progression (e.g., CR1); ligand-receptor signalling (e.g., CR3); cellular maturation, differentiation, and proliferation (e.g., CR4); enhancement or suppression of DNA replication (e.g., CR5, CR6); promotion of mRNA transcription by stimulating elongation of mRNA transcription (e.g., CR5, CR6); and transcriptional activation and repression (e.g., CR8). Other biological activities of the subject CR proteins are described herein or will be reasonably apparent to those skilled in the art. A polypeptide having at least one biological activity of the subject CR proteins may differ in amino acid sequence from the sequence shown in either SEQ ID NO:2, 4, 6, 8, 10, 12, or 14, but such differences result in a modified polypeptide which functions in the same or similar manner as the native CR or which has the same or similar characteristics of the native CR protein. Various modifications of a CR protein of the present invention to produce these and other functionally equivalent peptides are described in detail herein. The terms peptide, protein, and polypeptide are used interchangeably herein.

The present invention also pertains to isolated CR proteins which are isolated from, or otherwise substantially free of other cellular proteins normally associated with the CR protein. The language "substantially free of other cellular proteins" (also referred to herein as "contaminating proteins") or "substantially pure, substantially pure preparation, or purified preparations" are defined as encompassing CR protein preparations having less than 20% (by dry weight) contaminating protein, and preferably having less than 5% contaminating protein. Functional forms of the subject CR proteins can be prepared, for the first time, as purified preparations by using a cloned gene as described herein. As used herein, the term "purified", when referring to a peptide or DNA or RNA sequence, that the indicated molecule is present in the substantial absence of other biological macromolecules, such as other proteins. The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as the term "purified". "Isolated" and "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions.

The term "isolated" as also used herein with respect to nucleic acids, such as DNA or RNA, refers to molecules separated from other DNAs, or RNAs, respectively, that are present in the natural source of the macromolecule. For example, an isolated nucleic acid encoding one of the subject CR proteins preferably includes no more than 10 kilobases (kb) of nucleic acid sequence which naturally immediately flanks that particular CR gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

Furthermore, isolated peptidyl portions of the subject CR proteins can also be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry For example, a CR protein of the present invention can be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a CR protein activity, such as by microinjection assays.

The structure of the subject CR proteins can be modified for such purposes as enhancing therapeutic or prophylactic efficacy, or stability (e.g., ex vivo shelf life and resistance to proteolytic degradation in vivo). Such modified peptides, when designed to retain at least one activity of the naturally-occurring form of the protein, are considered functional equivalents of the CR proteins described in more detail herein. Such modified peptide can be produced, for instance, by amino acid substitution, deletion, or addition.

Moreover, it is reasonable to expect that an isolated replacement in CR proteins of the invention of a leucine with an isoleucine or valine, an aspartate with a glutamate, a threonine with a serine, or a similar replacement of an amino acid with a structurally related amino acid (i.e. conservative mutations) will not have a major effect on the biological activity of the resulting molecule. Conservative replacements are those that take place within a family of amino acids that are related in their side chains. Genetically encoded amino acids are divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur -containing= cysteine and methionine. (see, for example, *Biochemistry*, 2nd ed., Ed. by L. Stryer, W H Freeman and Co.: 1981). Whether a change in the amino acid sequence of a peptide results in a functional CR homolog can be readily determined by assessing the ability of the variant peptide to produce a response in cells in a fashion similar to the wild-type CR protein or peptide. Peptides in which more than one replacement has taken place can readily be tested in the same manner.

Another aspect of the invention pertains to an antibody or antibody preparation specifically reactive with at least one epitope of at least one of the subject CR proteins. For example, by using immunogens derived from the present CR proteins, based on the cDNA sequences, anti-protein/anti-peptide antisera or monoclonal antibodies can be made by standard protocols (See, for example, *Antibodies: A Laboratory Manual* ed. by Harlow and Lane (Cold Spring Harbor Press: 1988)). A mammal such as a mouse, a hamster or rabbit can be immunized with an immunogenic form of the peptide (e.g., CR protein or an antigenic fragment which is capable of eliciting an antibody response). Techniques for conferring immunogenicity on a protein or peptide include conjugation to carriers or other techniques well known in the art. An immunogenic portion of the subject CR proteins can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of the CR proteins of the present invention, e.g. antigenic determinants of a protein represented by one of SEQ ID NOs:2, 4, 6, 8, 10, 12, or 14 or a closely related human or non-human mammalian homolog (e.g. 90 percent homologous, more preferably at least 95 percent homologous). In yet a further preferred embodiment of the present invention, the anti-CR protein antibodies do not substantially cross react (i.e. react specifically) with a protein which is: e.g. less than 90 percent homologous to one of SEQ ID NOs:2, 4, 6, 8, 10, 12, or 14; e.g. less than 95 percent homologous with one of SEQ ID NOs:2, 4, 6, 8, 10, 12, or 14; e.g. less than 98–99 percent homologous with one of SEQ ID NOs:2, 4, 6, 8, 10, 12, or 14. The language "not substantially cross react" means that the antibody has a binding affinity for a non-homologous protein which is less than 10 percent, more preferably less than 5 percent, and even more preferably less than 1 percent, of the binding affinity for a protein of SEQ ID NOs:2, 4, 6, 8, 10, 12, or 14.

Following immunization, anti-CR antisera can be obtained and, if desired, polyclonal anti-CR antibodies isolated from the serum. To produce monoclonal antibodies, antibody producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) *Nature*, 256: 495–497), the human B cell hybridoma technique (Kozbar et al., (1983) *Immunology Today*, 4: 72), and the EBV-hybridoma technique to produce human monoclonal antibodies (Cole et al., (1985) *Monoclonal Antibodies and Cancer Therapy*, Alan R. Liss, Inc. pp. 77–96). Hybridoma cells can be screened immunochemically for production of antibodies specifically reactive with a CR protein of the present invention and monoclonal antibodies isolated from a culture comprising such hybridoma cells.

The term "antibody" as used herein is intended to include fragments thereof which are also specifically reactive with one of the subject CR proteins. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. Antibodies of the present invention are further intended to include bispecific and chimeric molecules having an anti-CR portion.

Both monoclonal and polyclonal antibodies (Ab) directed against CR or CR variants, and antibody fragments such as Fab' and F(ab')$_2$, can be used to block the action of a CR proteins and allow the study of the role of the particular CR protein of the present invention in cell signalling.

The nucleotide sequence determined from the cloning of the subject CR proteins from a human cell line allows for the generation of probes designed for use in identifying CR homologs in other human cell types, as well as CR homologs from other animals. For instance, the present invention also provides a probe/primer comprising a substantially purified oligonucleotide, wherein the oligonucleotide comprises a region of nucleotide sequence which hybridizes under stringent conditions to at least 10 consecutive nucleotides of sense or anti-sense sequence of one of SEQ ID NOs:1, 3, 5, 7, 9, 11, or 13, or naturally occurring mutants thereof. In preferred embodiments, the probe/primer further comprises a label group attached thereto and is able to be detected, e.g. the label group is selected from the group consisting of radioisotopes, fluorescent compounds, enzymes, and enzyme co-factors. Such probes can be used as a part of a test kit for measuring a level of an CR nucleic acid in a sample of cells from a patient; e.g. measuring a CR mRNA level; e.g. determining whether a genomic CR gene has been mutated or deleted.

In addition, nucleotide probes can be generated from the cloned sequence of the subject CR proteins, which allow for histological screening of intact tissue and tissue samples for the presence of a CR mRNA. Use of probes directed to CR mRNAs, or to genomic CR sequences, can be used for both predictive and therapeutic evaluation of allelic mutations which might be manifest in a variety of disorders including cancer, immunodeficiencies, autoimmune disorders, developmental abnormalities, infectious diseases, toxic damage due to irradiation, chemicals, and other noxious compounds or natural products. Used in conjunction with anti-CR antibody immunoassays, the nucleotide probes can help facilitate the determination of the molecular basis for a developmental disorder which may involve some abnormality associated with expression (or lack thereof) of a CR protein. For instance, variation in CR synthesis can be differentiated from a mutation in the CR coding sequence.

Also, the use of anti-sense techniques (e.g. microinjection of antisense molecules, or transfection with plasmids whose transcripts are anti-sense with regard to a CR mRNA or gene sequence) can be used to investigate the normal cellular function of each of the novel CR proteins, e.g. in cell signalling. Such techniques can be utilized in cell culture, but can also be used in the creation of transgenic animals.

Furthermore, by making available purified and recombinant CR proteins, the present invention facilitates the development of assays which can be used to screen for drugs which are either agonists or antagonists of the normal cellular function of the subject CR proteins, or of their role in cell signalling.

In another aspect, the invention features transgenic non-human animals which express a recombinant CR gene of the present invention, or which have had one or more of the subject CR gene(s), e.g. heterozygous or homozygous, disrupted in at least one of the tissue or cell-types of the animal.

In another aspect, the invention features an animal model for disorders related to cell signalling, which has a CR allele which is mis-expressed. For example, a mouse can be bred which has a CR allele deleted, or in which all or part of one or more CR exons are deleted. Such a mouse model can then be used to study disorders arising from mis-expressed CR genes.

This invention is further illustrated by the following examples which in no way should be construed as being further limiting. The contents of all cited references (including literature references, issued patents, published patent applications, and co-pending patent applications) cited throughout this application are hereby expressly incorporated by reference.

EXAMPLES

Example I

Construction of cDNA Library Containing Clones of Ligand-Induced Genes

Human peripheral blood mononuclear cells (PBMCs) were isolated by Ficoll/Hypaque discontinuous centrifugation, and cultured at $10^6$ cells/ml in complete medium comprised of RPMI 1640 (GIBCO Laboratories, Grand Island, N.Y.) supplemented with 10% heat-inactivated (56° C., 30 min) calf serum (Sterile Systems, Inc., Logan, Utah), 50 mg/ml L-glutamine, and 50 units/ml penicillin. T-cells were activated by stimulation of the CD3 component of the T-cell receptor complex with an anti-CD3 reactive monoclonal antibody (OKT3, 1: 10,000 dilution, Ortho Pharmaceuticals, Raritan, N.J.) in the presence of absence of 10 mg/ml CHX, and DNA synthesis was monitored at 48–52 hr by adding 0.5 mCi [$^3$H]-thymidine to 200 ml aliquots of cell cultures in 96-well microtiter plates. Cultures were harvested onto glass fiber filters, radioactivity was counted by liquid scintillation, and [$^3$H]-thymidine incorporation was calculated as cpm/$10^4$ cells/hr.

IL-2R-positive T-cell blasts were prepared by stimulation of PBMCs with OKT3 for 3 days, after which the cells were washed and replaced in culture for an additional 11 days in the presence of 500 pM IL-2. The cells were subsequently washed and placed in culture in the absence of IL-2 for 36 hr, followed by a 12 hr stimulation with 50 ng/ml phorbol 12,13 dibutyrate (PdBu) to augment high-affinity IL-2R expression. Cells were washed free of PdBU and placed in culture for 12 hr prior to restimulation. Such treatment enabled the generation of a $G_0/G_1$-synchronized cell population, made up of greater than 90% T8-positive T lymphocytes (Gullberg et al. (1986) *J. Exp. Med.* 163:270–284).

Human IL-2R-positive T-cell blasts were cultured in the presence of 1 nM IL-2, 10 mg/ml CHX, 250 mM 4-thiouridine (Sigma Chemical Co., St. Louis, Mo.) and 2.5 mCi/ml [5,6-$^3$H]-uridine (48 Ci/mmole, Amersham, Arlington Heights, Ill.) for 2 hr. CHX was included in the 2 hr IL-2 stimulation of the IL-2R-positive, $G_0$/G1-synchronized human T-cells from which the cDNA library was generated in order to isolate immediate-early genes, and also to possibly superinduce the expression of lowabundance messages. Total RNA was isolated essentially as described by Caligiuri et al. ((1989) *J. Exp. Med.* 171:1509–1526), and the 4-thiouridine-labelled RNA purified by passage over a phenylmercury agarose column as described by Woodford et al. ((1988) *Anal. Biochem.* 171:166–172). The cells were labelled with 4-thiouridine during stimulation, to enable isolation of only those transcripts which were synthesized during the period of IL-2 and CHX treatment (Stetler et al. (1984) *Proc. Nat. Acad. Sci.* (USA) 81:1144–1148) and Woodford et al. ((1988) Anal. Biochem. 171:166–172). Fractionation of total cellular RNA resulted in a 10-fold enrichment for newly-synthesized transcripts.

This thiol-selected RNA was used in the synthesis of Not-1 primer/adapter-primed cDNA, utilizing the Riboclone cDNA Synthesis System (Promega, Madison, Wis.) according to manufacturers instructions. After addition of EcoRI adapters (Promega), Not-1 digestion, and size selection for fragments greater than 500 base pairs (bp), the cDNA was ligated directionally into an EcoRI- and Not-1-digested pBluescript II SK+ plasmid vector (Stratagene, La Jolla, Calif.), followed by transformation into Epicurian Coli XL-1 Blue competent cells (Stratagene). A cDNA library of approximately 10,000 clones resulted.

Example II

Screening of cDNA Library for Clones Containing Ligand-Induced Genes

About 10% of the cDNA library was then screened using radiolabelled cDNA probes made from mRNA isolated from T-cells induced with IL-2 or from uninduced cells as follows. Single-stranded [$^{32}$P]-labelled cDNA probes were prepared from poly(A)$^+$ RNA isolated from human T-cell blasts stimulated for 2 hr with medium (unstimulated probe), or 1 nM IL-2 and 10 mg/ml CHX (stimulated probe). Total cellular RNA was prepared as described by Caligiuri et al. ((1989) *J. Exp. Med.* 171:1509–1526), and poly(A)$^+$ RNA was isolated by three passages over an oligo-dT-cellulose column (5 Prime-3 Prime, West Chester, Pa.). First strand cDNA synthesis was performed with an oligo-dT 12–18 primer (United States Biochemical Corp., Cleveland, Ohio), using the Riboclone cDNA Synthesis System (Promega, Madison, Wis.) according to manufacturers instructions, with the exception of dCTP at a final concentration of 35 mM and the addition of 2.5 mCi/ml [$^{32}$P]-dCTP. Hybridization was carried out for 72–96 hr at 42° C. in 50% formamide, with a final probe concentration of approximately $2 \times 10^6$ cpm/ml (W. M. Strauss, in *Current Protocols in Molecular Biology*, (1989) pp. 6.3.1–6.3.6). Subsequent to hybridization, filters were washed repeatedly at 62° C. in 0.1× SSC (1× SSC=0.15M NaCl, 0.015M sodium citrate, pH 7.0), 0.1% SDS and placed on film (Kodak XAR-5) with Dupont Cronex intensifying screens overnight at −70° C. The initial screening yielded 18 putative positive clones which exhibited differential hybridization to the stimulated and unstimulated probes after three independent screens. These clones were isolated for further characterization by Northern Blot analysis.

Total cellular RNA was isolated by the guanidine thiocyanate method described by Caligiuri et al. (ibid.), and denatured in glyoxal and DMSO. The RNA was fractionated on a 1% agarose gel in 0.01M $NaH_2PO_4$ with 0.5 mg/ml ethidium bromide (Selden, *Current Protocols in Molecular Biology*, (1989) pp. 4.9.5–4.9.8). To estimate sizes of RNA transcripts, a 0.24–9.5 kb RNA ladder (Bethesda Research Laboratories, Gaithersburg, Md.) was run alongside the cellular RNA samples. After visualization under ultraviolet light, the RNA was transferred to nitrocellulose by capillary transfer in 10× SSC. Plasmids were purified from the clones of interest, and the Not-1- and EcoRI-excised inserts [$^{32}$P]-labelled with random primers. Hybridization was carried out in 50% formrnamide at 42° C. for 48–72 hr, followed by repeated washes in 0.1× SSC, 0.1% SDS at 56–62° C. (Selden, ibid.). Filters were exposed to Kodak XAR-5 film with Dupont Cronex intensifying screens, and specific bands quantitated with an EC densitometer (EC Apparatus Corp., St. Petersburg, Fla.).

In as much as CHX was included in both the library and probe preparation, it was essential to verify that the differential expression of putative clones observed upon colony screening was not due solely to the effects of this drug. In addition, determination of the sizes and patterns of induction of the RNA transcripts was necessary to enable estimation of the redundancy of the clones. Therefore, Northern blot analysis was performed with RNA isolated from human IL-2R-positive T-cell blasts stimulated with either CHX or IL-2 alone, or with a combination of the two agents.

Hybridization of the RNA with probes generated from the inserts of each of the 18 putative clones resulted in the identification of 4 clones that were solely CHX-induced. For the remaining 14 clones, the induction by the combination of IL-2 and CHX could not be accounted for by the effects of CHX alone. Based upon the patterns of induction and approximate sizes of the RNA transcripts, 8 readily distinguishable and apparently unique IL-2-induced genes were discerned, as partial sequences, among these 14. These are described in Table X.

TABLE 2

| Clone | Nucleotide Sequence | Insert (kb) Size of Partial Sequence | RNA (bases) Size of Partial Sequence | IL-2 Induction |
|---|---|---|---|---|
| CR1 (1A8) | nucleotide 857 to 2406 of SEQ ID NO: 1 | 1.6 | 2406 | 24 |
| CR2 (1F5) | nucleotides 1 to 163 and nucleotides 1093 to 1283 of SEQ ID NO: 3 | 1.1 | 1283 | 7 |
| CR3 (10A8) | nucleotides 718 to 901 and nucleotides 2265 to 2450 of SEQ ID NO: 5 | 2.0 | 2450 | 22 |
| CR4 (10D6) | nucleotides 2101 to 2291 and nucleotides 2679 to 2928 of SEQ ID NO: 7 | 1.0 | 2946 | 6 |
| CR5 (10F9) | nucleotides 763 to 902 and nucleotides 1641 to 2020 of SEQ ID NO: 9 | 1.4 | 2020 | >50 |
| CR6 (11B2) | nucleotides 310 to 513 and nucleotides 687 to 1066 of SEQ ID NO: 11 | 1.0 | 1066 | 5 |
| CR7 (11E6) | corresponds to nucleotides of pim-1 sequence in Selten et al. | 0.7 | 2400 | 17 |
| CR8 (13E2) | nucleotides 1721 to 1915 of SEQ ID NO: 13 | 1.5 | 2980 | 7 |

The original designations of the CR clones are included in parentheses in the left-hand column of Table II. The original designations are used herein to refer to the partial sequences shown in the column second from the left in Table II. As shown in Table II and in FIGS. 8A–8H, three of the genes, CR1, CR3, and CR5, were induced by IL-2 alone, while five of the genes, CR2, CR4, CR6, CR7, and CR8, were induced by both CHX and IL-2. In several instances, the combination of IL-2 and CHX resulted in a marked synergistic induction.

Example III

Kinetic Analysis of IL-2-Induced Gene Expression

The temporal expression of the novel, IL-2-induced genes was determined by Northern blot analysis, using RNA isolated from human IL-2R-positive T-cell blasts after IL-2 stimulation in the presence or absence of CHX. Northern blots were prepared with 15 mg total RNA isolated from $G_0/G_1$-synchronized human T-cells stimulated for 0, 0.5, 1, 2, 4, or 8 hours with 1 nM IL-2 or IL-2+10 mg/ml CHX. Filters were probed with the cDNA inserts of the IL-2-induced clones.

As shown in FIGS. 9A–9H, two of the genes, 1A8 (FIG. 9A) and 10D6 (FIG. 9B), exhibited rapid induction, reaching peak levels within 1–4 hr of IL-2 stimulation and returning to basal levels after 8 hr, while the other six clones (FIGS. 9C–9H) remained at elevated levels for at least 8 hr after IL-2 treatment. The magnitude of IL-2 induction of steady state RNA levels of the clones ranged from an approximately 5-fold elevation of clone 11B2 (FIG. 9F) to a greater than 50-fold stimulation of clone 10F9 (FIG. 9E) during the interval examined. These results are also summarized in Table II. Several of the clones were superinduced by CHX, with an increase observed in both the magnitude and duration of the IL-2 response.

The kinetics of induction of previously characterized IL-2-responsive genes have been found to range from those such as c-fos, which are rapidly and transiently induced within minutes of IL-2 stimulation (Dautry et al. (1988) *J. Biol. Chem.* 263:17615–17620), to those which remain at elevated levels through $G_1$ to S phase entry (Sabath et al. (1990) *J. Biol. Chem.* 265:12671–12678).

Example IV

Sequence Analysis of Clones Containing Ligand-Induced Genes

To verify the redundancy of the clones as estimated from Northern analysis, as well as to determine the identities of the genes, the cDNA clones were subjected to sequence analysis.

Plasmids were isolated from the clones of interest essentially as described by Kraft et al. ((1988) *Biotechniques* 6:544–547), and vector primers were used to sequence the termini of the cDNA inserts, employing the Sequenase 2.0 dideoxy sequencing kit (United States Biochemical, Cleveland, Ohio). Approximately 200 bases of sequence were attained from each end of the inserts. These partial sequences are described in Table II. Searches of the GenBank and EMBL data bases were performed with the FASTA program as described by Pearson et al. ((1988) *Proc. Natl. Acad. Sci.* (USA) 85:2444–2448).

The combination of sequence and Northern analyses revealed that the 14 putative IL-2-induced clones consisted of 8 unique genes, three of which, 1A8, 11B2, and 13E2, were isolated three times each. Searches of the GenBank and EMBL data bases with the partial sequences enabled the identification of one clone, 11E6, as pim-1, a previously characterized IL-2-induced gene (Dautry et al. (1988) *J. Biol. Chem.* 263:17615–17620; and Kakut-Houri et al. (1987) *Gene* 54:105–111) which encodes a 33 kD cytoplasmic kinase (Telerman et al. (1988) *Mol. Cell. Biol.* 8:1498–1503).

Thus, by utilizing the method of the invention seven unique IL-2 induced genes were cloned, representing novel human genes. These clones were identified after screening only approximately 800 library colonies, and thus, it is estimated that as many as 80 additional novel IL-2-induced genes remain to be detected in the 10,000-clone library.

To determine the complete sequences of these clones described in Table II the original partial cDNAs were used as probes to screen a second cDNA library. It is standard procedure to use partial cDNA inserts identified by an initial screen of a cDNA library to make radiolabeled cDNA probes to screen a second library to obtain clones with the portions missing in the initial cDNA clones. This was done, briefly, as follows: a second cDNA library was prepared from mRNA obtained from human T cells stimulated for two hours with interleukin-2 in the presence of cycloheximide by cloning into the λgt-10 phage vector using standard methods. (Sambrook, J. et al. Molecular Cloning: A Laboratory Manual (Cold Spring Harbor Laboratory Press, New York, 1989) pp. 2.82–2.122).

This second cDNA library was then screened using as probes each of the cDNA fragments obtained from the first, thiol-selected cDNA library. Candidate clones that corresponded to the correct size according to the mRNA were then subcloned and sequenced. The complete cDNA sequences (and the predicted amino acid sequences) of seven out of eight of these clones are set forth in SEQ ID NOs:1–14 and FIGS. 1–7. The complete cDNA sequence (and the predicted amino acid sequence) of the eighth clone was determined to be identical to that of the IL-2 induced gene pim-1. The nucleotide sequence as well as the predicted amino acid sequence of pin-1 are set forth at page 605 in Selten, G. et al. (1986) *Cell* 46:603–611.

Example V

Determination of Sensitivity of IL-2-Induced Gene Expression

As a further means of characterizing the regulation of expression of these genes, the sensitivity of induction to the known IL-2 functional antagonist was investigated. Human IL-2R-positive T-cell blasts were stimulated with IL-2 in the absence or presence of 0.5 mM dibutyryl-cAMP, a concentration of the membrane-permeant cAMP analog sufficient to inhibit IL-2-mediated GI progression without adversely affecting cellular viability. The effect of an equivalent molar amount of sodium butyrate, which does not inhibit the IL-2 response, was also tested to control for the actions of free butyric acid.

Northern blots were prepared as follows: Human IL-2R-positive T cells were treated with 1 nM IL-2 alone or in combination with 0.5 mM dibutyryl cAMP or sodium butyrate (NaBt) for 1, 2, or 4 hours. Filters were prepared with 15 mg total RNA and hybridized with cDNA inserts or the IL-2 induced clones.

These analyses demonstrate that the IL-2 induction of one gene, 1A8 (FIG. 10A) is markedly inhibited when the intracellular level of cAMP is raised by the addition of dibutyryl cAMP, whereas the expression of two others, 10D6 (FIG. 10B) and 13E2 (FIG. 10C), is augmented approximately 3-fold. By comparison, the expression of five of the genes was not affected by elevated cAMP (FIGS. 10D–10H). Thus, the sequences in clone 1A8 may be involved in T-cell proliferation. The fact that not all genes were sensitive to cAMP indicated that the observed results were not due to nonspecific effects, and furthermore that the previously documented down-regulation of IL-2R binding capacity by cAMP (Johnson et al. (1990) *J. Immunol.* 145:1144–1151) could not account for the inhibition of gene expression.

Example VI

Determination of Role of T-cell Receptor Activation in the Stimulation of Expression of IL-2-Induced Genes In order to determine if activation of the T-cell receptor mediates the stimulation of expression of cytokine IL-2-induced genes, the following study was performed. Northern blots were prepared from 20 mg total cellular RNA isolated from human peripheral blood mononuclear cells (PBMCs) stimulated with a monoclonal antibody (OKT3) specific to the CD3 component of the T-cell antigen receptor complex. Blots were probed with cDNA inserts of the IL-2-induced clones. Data was determined as the mean±SEM (n=6).

By isolation of RNA at early time intervals, it was possible to identify those genes which were induced by T-cell receptor triggering in the absence of IL-2 effects. As shown in FIGS. 11A–11H, only one of the genes, 10D6 exhibited heightened levels of expression after 2 hr of T-cell receptor activation, while the seven others were apparently insensitive to this stimulus. Two of the clones, 1F5 and 11 B2, were undetectable, even after seven days of autoradiographic exposure of the Northern blots. Two other genes, 11E6 and 13E2, were expressed at relatively high levels regardless of the stimulus; activation with anti-CD3 did not induce RNA expression beyond the level observed by culture in medium alone. Identical results were obtained after 1 and 4 hr of stimulation.

To determine whether the cells were actually activated via CD3, aliquots of the cells were left in culture for 52 hr in the presence of 10 mg/ml CHX, alone, OKT3 alone, or OKT3+CHX, after which cell cycle progression was monitored by [$^3$H]-thymidine incorporation into RNA.

As shown in FIG. 12, the cells were sufficiently stimulated by anti-CD3. Thus, the T-cell receptor-induced expression of only one of the genes was comparable to that seen with IL-2 stimulation, while the expression of the seven others was unique to the IL-2 signaling pathway. Thus, the methods described herein to identify IL-2-induced gene successfully selected and enriched for these genes that are highly specific for cytokine (IL-2) activation.

Of the 8 IL-2 induced $G_1$ progression genes reported here, only one appears to also be induced during the T cell receptor-mediated competence phase of the cell cycle. Thus, while several genes such as c-fos, c-myc and c-raf-1 are known to be induced during both the initial $G_0$-$G_1$ and subsequent $G_1$-S phase transitions, the expression of a number of IL-2-stimulated genes is unique to the latter event. In addition, the immediate-early genes reported here appear to define a class distinct from the IL-2-induced genes isolated by Sabath et al. ((1990) *J. Biol. Chem.* 265:12671–12678). These investigators utilized a differential screening procedure to isolate genes expressed at the $G_1$/S phase boundary in a murine T helper clone which was stimulated with IL-2 for 20 hr in the absence of protein synthesis inhibitors. In this case, the expression of only 3 of the 21 clones isolated was inhibited by CHX, while the remainder were insensitive to this agent. This pattern of regulation markedly contrasts with the CHX superinduction observed with the immediate-early IL-2-induced genes described here. Moreover, these observations indicate that IL-2 stimulates a complex program of gene expression, ranging from those genes induced very early in $G_1$ through those subsequently expressed at the $G_1$/S phase transition.

Example VII

Cloning and Analysis of CR8

As described above, the CR8 gene encodes a novel basic helix-loop-helix (bHLH) protein. While the CR8 transcript is ubiquitously expressed in many tissues, it is induced by IL-2 as well as by IL-3 in cytokine-dependent lymphoid cell lines. In an IL-2-dependent human T cell line Kit 225, the CR8 transcript is induced not only by IL-2, but also by interferon b and forskolin, which elevates intracellular cAMP. The bHLH domain of CR8 shows the highest structural homology to a Drosophila transcriptional repressor hairy. The recombinant CR8 protein binds preferentially to the Class B E-box DNA sequence (CACGTG), which is found in the promoter/enhancer regions of a number of genes associated with cell growth and differentiation, suggesting that CR8 may regulate the transcription of such genes.

The cloning of the full-length cDNA for CR8 is described in detail herein. The predicted amino acid sequence revealed that CR8 contains a helix-loop-helix (HLH) domain, characteristic for transcription factors. The HLH domain is a dimerization motif characterized by the two amphipathic a-helices separated by a nonhelical loop of variable length (Davis, R. L. et al.(1990) Cell 60:733–746). Most of the HLH family members possess a cluster of basic amino acid residues immediately N-terminal to the HLH region [basic helix-loop-helix (bHLH)], which are required for site-specific DNA binding, while others lack the basic region and function as negative regulators of DNA binding (Benezra, R. et al. (1990) Cell 61:49–59; Ellis, H. M. et al. (1990) Cell 61:27–38; Garrell, J. et al. (1990) Cell 61:39–48.22,28). A wide variety of developmental processes are regulated by HLH proteins; the MyoD family of myogenic transcription factors directly induce the expression of muscle-specific genes, thereby functioning as master regulators of muscle cell lineage specification (reviewed in (Edmonson, D. G. et al. (1993) J. Biol. Chem. 268:755–758; Weintraub, H. (1993) Cell 75:1241–1244)). The crucial role of the bHLH protein encoded by the tal-1/SCL gene in hematopoiesis, originally discovered as a chromosomal breakpoint in leukemia (Begley, C. G. et al. (1989) Proc. Natl. Acad. Sci. USA 86:10128–10132; Chen, G. et al. (1990) EMBO J. 9:415–424; Finger, L. et al. (1989) Proc. Natl. Acad. Sci. USA 86:5039–5043), is illustrated by the absence of blood formation in tal-1 null mutant mice (Shivdasani, R. A. et al. (1995) Nature 373:432–434).

The regulation of immunoglobulin (Ig) gene expression has been extensively studied, and has been shown to be controlled by numerous transcription factors that recognize specific DNA sequences in the Ig enhancers (Kadesch, T. (1992) Immunol. Today 13:31–36). Recent reports on E2A null mutant mice that lack mature B cells clearly depict the impact of these bHLH proteins on B cell development (Bain, G. et al. (1994) Cell 79:885–892; Zhuang, Y. et al. (1994) Cell 79:875–884). Genetic analysis of neural cell fate and sex determination in Drosophila provided in vivo evidence for interaction between bHLH proteins (reviewed in (Jan, Y. N. et al. (1993) Cell 75:827–830)). For instance, bHLH proteins encoded by daughterless (da) and the achaete-scute complex (AS-C) heterodimerize and positively regulate sensory organ formation. On the other hand, the genes encoding negative regulators such as hairy and extramacrochaetae are required to control the appropriate pattern of neural precursor distribution. Moreover, because cell differentiation is often associated with the suppression of proliferation, some HLH proteins have also been implicated in the regulation of cell growth. One of the most extensively studied may be Myc, a bHLH protein encoded by the c-myc oncogene (reviewed in Marcu, K. B. et al. (1992) Annu. Rev. Biochem. 61:809–860). The negative regulator Id proteins which inhibit differentiation by forming inactive heterodimers with bHLH proteins, thereby may be required for proliferation. For example, the level of Id expression is higher in undifferentiated proliferating cells (Benezra, R. et al. (1990) Cell 61:49–59). Also, antisense oligonucleotide against Id mRNA inhibits re-entry to the cell cycle (Barone, M. V. et al. (1994) Proc. Natl. Acad. Sci. USA 91:4985–4988; Hara, E. et al. (1994) J. Biol. Chem. 269:2139–2145), and cell cycle progression is accelerated in 1d2 stable transfectant cell lines (Ivarone, A. et al. (1994) Genes & Dev 8:1270–1284).

The following Materials and Methods were used in this Example:

Cell Culture and Reagents:

Human T cells were prepared as described previously (Beadling, C. et al. (1993) Proc. Natl. Acad. Sci. USA 90:2719–2723); in short, peripheral blood mononuclear cells were cultured in RPMI 1640 supplemented with 10% (v/v) heat-inactivated fetal calf serum (FCS) and antibiotics in the presence of OKT3 (Ortho Pharmaceuticals) for 3 days, then for an additional 11 days in the presence of IL-2 (Takeda Chemical). The cells were subsequently removed from of IL-2 for 36 hr, followed by a 12 hr stimulation with phorbol-12, 13-dibutyrate (Sigma) to augment the expression of high-affinity IL-2 receptor. Such treatment enabled the generation of a G1/G1-synchronized cell population, comprised of >90% CD8+T lymphocytes (Gullberg, M. et al. (1986) J. Exp. Med. 163:270–284). Kit 225 is an IL-2-dependent human T cell line (Hori, T. et al. (1987) Blood 70:1069–1072). Ba/F3 and CTLL2 are mouse cell lines dependent on IL-3 and IL-2, respectively. Both Kit 225 and CTLL2 were maintained in RPMI 1640 supplemented with 10% (v/v) FCS and 500 pM recombinant human IL-2. Ba/F3 was maintained in RPM11640 supplemented with 10% (v/v) FCS and 5% (v/v) conditioned medium from fibroblasts transfected with mouse IL-3 as a source of IL-3. Recombinant mouse IL-3 was purchased from Genzyme. Before using for experiments, cell lines were made quiescent by growth factor deprivation for 72 hr for Kit 225, 12 hr for Ba/F3 and 2 hr for CTLL2.

Forskolin was obtained from Sigma. Human interferon (IFN) β was from GIBCO BRL. Proliferation was monitored by measuring the incorporation of [$^3$H-methyl]thymidine (Amersham) into ten thousand cells incubated with indicated reagents in 200 fl for 24 hr at 37° C. The culture was pulsed with 0.5 fCi [$^3$H]thymidine for the last 4 hr prior to harvest.

Northern Hybridization:

Total cellular RNA was isolated by RNAzolB (Tel-Test) and fractionated on a 1.2% agarose formaldehyde gel. RNA was visualized with ethidium bromide. After electrophoresis, RNA was transferred and fixed to Hybond-N+nylon membrane (Amersham) with 40 mM NaOH. Multiple Tissue Northern Blot membranes were purchased from Clontech. Membranes were hybridized with the radiolabeled probe for 3 hr to overnight at 65° C. in Rapid-Hyb hybridization solution (Amersham), washed twice with 2x SSC/0.1% SDS (1x SSC=150 mM NaCl/15 mM sodium citrate, pH 7.0) at room temperature for 15 min, once with 0.5x SSC/0.1% SDS at 60° C. for 15 min and subjected to autoradiography.

cDNA Library Screening:

The λgt10 cDNA libraries were constructed and screened according to the standard molecular biology procedure (Sambrook, J., E. F. Fritsch, and T. Maniatis. 1989. Molecular Cloning: A Laboratory Manual, Second Edition. Cold Spring Harbor Laboratory Press, Cold Spring Harbor, N.Y.). Poly(A)+RNA was isolated from IL-2-stimulated normal human T cells prepared as above and cDNA synthesis was primed with both oligo(dT)12–18 and random hexamers. The recombinant phages were screened with radiolabeled CR8 insert. For mouse CR8, a λgt10 cDNA library from IL-2-stimulated mouse splenocytes were screened with human CR8 insert under low-stringency condition.

Sequence Analysis:

CR8 cDNA sequence was analyzed by the fluorescence-based dideoxynucleotide termination method (Taq DyeDeoxyTM Terminator Cycle Sequencing Kit, Perkin Elmer) on the Applied Biosystems Model 373A DNA sequencer. Consensus sequences were constructed and analyzed with the help of the University of Wisconsin GCG software package. The BLAST algorithm from the National Center for Biotechnology Information (NCBI) was also employed for nucleotide and amino acid sequence homology search (Altschul, S. F. et al. (1990) *J. Mol. Biol.* 215:403–410).

Preparation of Recombinant Proteins:

The recombinant CR8 protein with histidine-tag was prepared using the XpressTM System (Invitrogen) according to the manufacturer's protocol. cDNA corresponding to the CR8 bHLH domain was obtained by PCR. The sequences of the primers, 5'-GGGGTCTACCAGGGATGTAC-3' (SEQ ID NO:15) for the 5' side, and 5'-GTAAACCACTCTGCAGGGCAATGA-3' (SEQ ID NO:16) for the 3' side, were slightly different from the final consensus sequence for CR8, but the difference did not affect the core bHLH motif. The PCR product was cloned into pT7Blue T-vector (Novagen) and subsequently into pRSET-A vector at BamHI and HindIII sites. Constructs were confirmed by DNA sequencing. The protein was overexpressed in JM109 at 37° C. in the presence of isopropylthio-b-D-galactoside (IPTG) by infecting the bacteria with M13 phages that contain the T7 RNA polymerase gene. The cells were lysed with 100 fg/ml lysozyme in native binding buffer (20 mM sodium phosphate, pH 7.8, 500 mM NaCl), the lysate was loaded on a ProBondTM Ni2+column, and the recombinant protein was eluted with native-imidazole elution buffer (20 mM sodium phosphate, pH 6.0, 500 mM NaCl, 500 mM imidazole). The protein was then dialyzed against lysis buffer (50 mM Tris-HCl, pH 7.5, 150 mM NaCl, 1 mM EDTA, 10% glycerol, 0.1% Triton X-100, 1 mM DTT) and concentrated on a Microcon 10 (Amicon). To confirm the purity and the quantity, the protein was fractionated on a 12% SDS-polyacrylamide gel with protein standards of known concentrations and visualized by silver staining. The recombinant protein corresponding to the bHLH domain of da was supplied by Dr. Michael Caudy (Cornell University Medical College).

Mobility Shift Assay:

The oligonucleotide probes used for the electrophoretic mobility shift assay (EMSA) are as follows: the Class A site used was the CACCTG hexamer (CAGGTG for the opposite strand) from the T5 promoter region of the Drosophila AS-C (Villares, R. et al. (1987) *Cell* 550:415–424) (5'-GATCGTAGTCACGCAGGTGGGATCCCTA-3' (SEQ ID NO:17) and 5'-GATCTAGGGATCCCACCTGCGTGACTAC-3' (SEQ ID NO:18) for the opposite strand), the Class B site was the CACGTG hexamer from the USF binding site in the adenovirus major late promoter (Gregor, P. D. et al. (1990) *Genes & Dev.* 4:1730–1740) (5'-GATCGGTGTAGGCCACGTGACCGGGTGT-3' (SEQ ID NO:19) and 5'-GATCACACCCGGTCACGTGGCCTACACC-3') (SEQ ID NO:20), the Class C site was the CACGCG hexamer (CGCGTG for the opposite strand) from the AS-C T5 promoter (5'-GATCGGCAGCCGGCACGCGACAGGGCC-3' (SEQ ID NO:21) and 5'-GATCGGCCCTGTCGCGTGCCGGCTGCC-3') (SEQ ID NO:22), and the N-box (CACNAG) was the double hexamer sequence from the Enhancer of split [E(spl)] m8 promoter (Klimbt, C. et al. (1989) *EMBO J.* 8:203–210) (5'-GATCACGCCACGAGCCACAAGGATTG-3' (SEQ ID NO:23) and 5'-GATCCAATCCTTGTGGCTCGTGGCGT-3' (SEQ ID NO:24). One strand of the oligonucleotide was labeled with [g-32P]ATP by T4 polynucleotide kinase, hybridized with three times excess of the opposite strand, and purified using MERmaid oligonucleotide purification kit (BIO 101). 150 ng of the protein was allowed to bind to 50,000 cpm (equivalent to 0.5 ng in a typical experiment) of the labeled probe for 15 min at room temperature in 20 mM Hepes, pH 7.6, 50 mM KCl, 10 mM DTT, 5% glycerol, 0.5 mM EDTA and 0.3 mg/ml BSA. Two microgram of poly (dI-dC) was added to each 20 fl reaction as on-specific DNA. Samples were analyzed on a 5% native polyacrylamide gel and visualized by autoradiography.

Regulation of CR8:

CR genes were originally defined in IL-2 stimulated normal human T cells. To examine CR8 expression in cytokine-dependent cell lines, the level of CR8 expression was measured by Northern hybridization in the IL-2-dependent human T cell line Kit 225, the IL-3-dependent mouse pro-B cell line Ba/F3, and the IL-2-dependent mouse T cell line CTLL2. The results of this experiment are illustrated in FIGS. 13A–13C. In FIG. 13A, RNA was isolated from quiescent normal human T cells (lanes 1 and 2), IL-2-dependent human T cell line Kit 225 (lanes 3 and 4), IL-3-dependent mouse pro-B cell line Ba/F3 (lanes 5 and 6) and IL-2-dependent mouse T cell line CTLL2 (lanes 7 and 8) left untreated (lanes 1, 3, 5, and 7) or stimulated with 500 pM recombinant human IL-2 (lanes 2, 4, and 8) or 10 U/ml recombinant mouse IL-3 (lane 6) for 2 hr at 37° C. The amount of the growth factor used in the experiment was sufficient to induce maximal [$^3$H]thymidine incorporation. Ten microgram of total RNA was analyzed on formaldehyde/agarose gel and hybridized with either human (lanes 1 to 4) or mouse (lane 5 to 8) CR8 cDNA.

As shown in FIG. 13A, a single 3.2 kb species hybridized to the cDNA probe, and in all three cell lines tested, the level of CR8 was clearly augmented when the cells were stimulated with their respective growth factors. Correlation between the level of CR8 and that of DNA synthesis was in the presence of growth-inhibitory agents was also examined. In this regard, increases in cytoplasmic cAMP are known to inhibit the growth of many cell types, including lymphocytes (Johnson, K. W. et al. (1988) *Proc. Natl. Acad. Sci. USA* 85:6072–6076). IFNs also exert antiproliferative activity on many cell types (Pestka, S. et al. (1987) *Annu. Rev. Biochem.* 56:727–777). Therefore, Kit 225 was stimulated with IL-2, IFN β, or forskolin, which increases cytoplasmic cAMP by activating adenylate cyclase, either alone or in combination. IL-2-dependent [$^3$H]thymidine incorporation was inhibited by IFNb and forskolin in Kit 225 cells in a dose-dependent fashion (FIG. 13B). FIG. 13B demonstrates that IFNP and forskolin inhibit IL-2-dependent [$^3$H] thymidine incorporation by Kit 225 cells. Ten thousand quiescent Kit 225 cells were incubated with indicated reagents in 200 fl for 24 hr at 37° C. The culture was pulsed with [$^3$H]thymidine for the last 4 hr to monitor the DNA synthesis. (●), IL-2 only (500 pM); (◇), IL-2 500 pM+varying concentrations of IFNb (U/ml); (○), IL-2 500 pM+varying concentrations of forskolin (fM). While forskolin was capable of reducing the IL-2-dependent [$^3$H] thymidine incorporation almost to the basal level, IFNβ-mediated inhibition never exceeded 70% of the maximal incorporation in several independent experiments. The expression of CR8 was compared with that of c-myc, an IL-2-inducible immediate-early gene that encodes a bHLH protein and is implicated for cell proliferation (Marcu, K. B. et al. (1992) *Annu. Rev. Biochem.* 61:809–860).

FIG. 13C shows the effect of antiproliferative agents on the expression of CR8 and c-myc transcripts in Kit 225.

Quiescent Kit 225 cells were left untreated (lane 1) or incubated with 500 pM IL-2 (lane 2), 1000 U/ml IFNb (lane 3), 100 fM forskolin (lane 4), 500 pM IL-2+1000 U/ml IFNa (lane 5) or 500 pM IL-2+100 fM forskolin (lane 6) for 2 hr at 37° 15 fg of total RNA was analyzed. The same membrane was probed with CR8 and c-myc. As shown in FIG. 13C, CR8 transcripts were moderately induced, not only by IL-2, but also by IFNβ or forskolin alone. Furthermore, the simultaneous stimulation of quiescent Kit 225 cells with IL-2 and IFNβ, or IL-2 and forskolin, did not suppress the IL-2-induced expression of CR8 transcripts. In contrast, IL-2-induction of c-myc expression was substantially inhibited in the presence of forskolin, while IFNβ did not significantly reduce IL-2-promoted c-myc expression.

Cloning of CR8:

The original human CR8 clone isolated from the thiol-selected library had a 1.5 kb insert, while the full-length mRNA transcript was estimated to be 3.2 kb from Northern blotting experiments. As the CR8 clone did not have a long open reading frame, two fulllength cDNA clones of human CR8 were isolated from a λgt10 human T cell cDNA library after two rounds of screening with cDNA fragments of the CR8 clone. These two clones were fully sequenced on both strands, and the amino acid sequence was deduced (FIG. 14). In FIG. 14, the asterisk denotes the stop codon. In-frame termination codon in the 5'-untranslated region, the nucleotide sequences used for PCR and the polyadenylation signal are underlined. The amino acid residues in the bHLH region are double-underlined. When the final consensus cDNA sequence of 2970 bp (excluding the poly(A) stretch) was screened against the nonredundant nucleotide databases using the NCBI BLAST E-mail server (GenBank release 86.0), no known genes in the database shared significant homology with CR8 except for nine EST sequences (Adams, M. D. et al. (1991) *Science* 252:1651–1656.). CR8 has an open reading frame of 412 amino acids, with an in-frame termination codon at position 198 followed by Met at position 240 in a reasonable context for translation initiation (CGCCATGG) (Kozak, M. (1986) *Cell* 44:283–292). The MOTIFS program in the GCG package predicted the presence of an HLH motif in CR8.

A mouse CR8 cDNA fragment corresponding to nt 388 to 2720 of the human sequence was also isolated from a λgt10 mouse cDNA library by comparison of CR8 with other bHLH Proteins. The protein database search with the putative peptide sequence revealed that CR8 shares homology with the bHLH proteins encoded by Drosophila hairy gene and the enhancer of split complex [E(spl)-C] of neurogenic genes. FIGS. 15A–15B show a sequence comparison of CR8 and other HLH proteins. Protein alignments were made to maximize homology within the bHLH domain. Amino acids conserved among most HLH proteins are shaded. The proline residues in the basic region and the arginine residues at position 13 ("R13") are boxed. The boxed alanine residue in MyoD is the one whose substitution to proline abrogated the DNA binding and muscle-specific gene activation activity of MyoD (Davis, R. L. et al. (1990) *Cell* 60:733–746). [h], human; [D], Drosophila melanogaster; [r], rat; and [m], mouse. Sources for sequences: hairy, (Rushlow, C. A. et al. (1989) *EMBO J*. 8:3095–3103); Enhancer of split [E(spl)] m7, (Klimbt, C. et al. (1989) *EMBO J*. 8:203–210); deadpan (dpn), (Bier, E. et al. (1992) *Genes & Dev* 6:2137–2151); HES-1, (Sasai, Y. et al. (1992) *Genes & Dev* 6:2620–2634); daughterless (da), (Caudy, M. et al. (1988) *Cell* 55:1061–1067); E12 and E47, (Murre, C. et al. (1989) *Cell* 56:777–783); MyoD, (Davis, R. L. et al. (1987) *Cell* 51:987–1000); Tal-1, (Begley, C. G. et al. (1989) *Proc. Natl.* *Acad. Sci. USA* 86:10128–10132); USF, (Gregor, P. D. et al. (1990) *Genes & Dev* 4:1730–1740); Max, (Blackwood, E. M. et al. (1991) *Science* 251:1211–1217); N-myc, (Slamon, D. J. et al. (1986) *Science* 232:768–772); L-myc, (Kaye, F. et al. (1988) *Mol. Cell. Biol.* 8:186–195); c-myc, (Gazin, C. et al. (1984) *EMBO J*. 3:383–387); extramacrochaetae (emc), (Ellis, H. M. et al. (1990) *Cell* 61:27–38; Garrell, J. et al. (1990) *Cell* 61:39–48) and Id1, (Benezra, R. et al. (1990) *Cell* 61:49–59).

When CR8 was aligned with other bHLH proteins (FIGS. 15A–15B), it was clear that most of the residues conserved throughout the family were present in CR8. Taken together with the result of the MOTIFS program, it was concluded that CR8 is a bHLH protein. The amino acid sequence of the 58-residue bHLH domain of CR8 showed 40% identity to hairy, 41% to E(spl)m7, and 45% to one of their mammalian counterparts HES-1. This degree of amino acid identity accounts well for the failure to detect any significant homology to any known bHLH proteins at the nucleotide sequence level. The amino acid sequence for human and mouse CR8 was 100% identical in the bHLH domain.

FIG. 15B shows a sequence comparison of CR8 and hairy-related bHLH. Conserved amino acids are shaded. Note that HES-2, 3 and 5 proteins do not align perfectly in the hairy-related homology region (HRHR)-2. Sources for sequences: HES-2, (Ishibashi, M. et al. (1993) *Eur. J. Biochem.* 215:645–652); HES-3, (Sasai, Y. et al. (1992) *Genes & Dev* 6:2620–2634); HES-5, (Akazawa, C. et al. (1992) *J. Biol. Chem.* 267:21879–21885); human hairy-like (HHL), (Feder, J. N. et al. (1994) *Genomics* 20:56–61); Drosophila melanogaster hairy [h(m)], (Rushlow, C. A. et al. (1989) *EMBO J*. 8:3095–3103); Drosophila virilis hairy [h(v)], (Wainwright, S. M. et al. (1992) *Mol. Cell. Biol.* 12:2475–2483); Tribolium hairy [h(T)], (Sommer, R. J. et al. (1993) *Nature* 361:448–450); E(spl)m5 and m8, (Klimbt, C. et al. (1989) *EMBO J*. 8:203–210); E(spl)m3, b/A, g/B, and d/C, (Deldakis, C. et al. (1 992) *Proc. Natl. Acad. Sci. USA* 89:8731–8735; Knust, E. et al. (1992) *Genetics* 132:505–518). As shown in FIG. 15B, the amino acid sequence of the bHLH region of CR8 is aligned with hairy, bHLH proteins of the E(spl)-C, deadpan (dpn) and their mammalian homologs (the term "hairy-related bHLH proteins" refer to them collectively). Among all the bHLH proteins described thus far, CR8 is the only one with a proline residue in the basic region, other than the hairy-related bHLH proteins. However, while the position of the proline residue is strictly conserved throughout the hairy-related bHLH proteins, in CR8 it is offset N-terminally by two residues. CR8 and hairy-related bHLH proteins are different in the C-terminus as well; all the hairy-related bHLH proteins terminate with a specific Trp-Arg-Pro-Trp (WRPW) motif, which is absent in CR8. Nevertheless, CR8 showed appreciable homology to other hairy-related bHLH proteins in the region immediately C-terminal to the bHLH domain, which has been shown previously to be rich in hydrophobic residues, and proposed to form two more α-helices in bHLH proteins of the E(spi)-C (43). This region is referred to herein as the "hairy-related homology region (HRHR)-2", the HRHR-1 being the bHLH domain. The region N-terminal to the bHLH domain and the C-terminal half of the CR8 protein are rich in proline (8 proline residues between positions 1 and 30, 22 between 310 and 405). Notably, there are no known proteins in the data bases that share homologies to these most N-terminal and C-terminal regions of CR8.

Tissue distribution of CR8 transcripts:

Murre et al. ((1989) *Cell* 58:537–544) categorized bHLH proteins based upon their tissue distribution. While proteins such as MyoD and AS-C gene products show a cell-type specific expression, others such as E12/E47 and da are fairly ubiquitously expressed. The tissue distribution of CR8 was analyzed using a Multiple Tissue Northern blot. CR8 transcripts of the expected size (3.2 kb) were detected in all tissues examined except placenta (see FIG. 16). FIG. 16 demonstrates that the Multiple Tissue Northern Blot membranes (Clontech; each lane contains 2 fg poly(A)+ RNA from indicated human tissue) were hybridized with human CR8 probe.

The expression of CR8 in peripheral blood leukocytes was unexpected, in that CR8 is not expressed by quiescent T cells. This may reflect much higher sensitivity of Multiple Tissue Northern blot prepared from poly(A)+ RNA compared to our previous Northern blots, which used total RNA. Alternatively, the contribution of other leukocytes such as B cells, NK cells, monocytes and granulocytes that were not present in the original T cell preparations could account for CR8 expression by the peripheral blood leukocytes.

DNA-binding activity of CR8:

The canonical bHLH binding sequence is called the E-box, CANNTG, originally identified in the immunoglobulin heavy chain enhancer (Ephrussi, A. et al. (1985) *Science* 227:134–140). Many bHLH proteins were later divided into two mutually exclusive classes, depending on whether they bind to the Class A sites (CAGCTG/CACCTG) or the Class B sites (CACGTG/CATGTG) (Dang, C. V. et al. (1992) *Proc. Natl. Acad. Sci.* USA 89:599602). The presence of an arginine residue at position 13 ("R13", see FIG. 15A) in the basic region, which CR8 contains, is considered to be the key structural criterion that defines Class B binding specificity. However, despite the presence of "R13", hairy-related bHLH proteins are reported to prefer noncanonical binding sites such as the N-box (CACNAG) (Akazawa, C. et al. (1992) *J. Biol. Chem.* 267:21879–21885; Sasai, Y. et al. (1992) *Genes & Dev* 6:2620–2634; Tietze, K. et al. (1992) *Proc. Natl. Acad. Sci.* USA 89:6152–6156) or the Class C (CACGCG) sites (Ohsako, S. et al (1994) *Genes & Dev* 8:2743–2755; Van Doren, M. et al. (1994) *Genes & Dev* 8:2729–2742.). Therefore, the binding of CR8 to all of these sites was tested.

Since it is well documented that the bHLH domain is sufficient to determine its DNA binding specificity (Pognonec, P. et al. (1994) *Mol. Cell. Biol.* 11:5125–5136), the bHLH domain of CR8 (CR8 bHLH) expressed in *E. coli* was employed for this study. A histidine-tag was added to facilitate the purification of the recombinant protein. While most of the recombinant protein localized in inclusion bodies, there was still enough soluble protein in the cytoplasm, thereby enabling its purification under native conditions using a $Ni^{2+}$ column. A single band of protein was detected at the expected size (16.6 kD with the histidine-tag) by silver staining. EMSA was carried out using this recombinant protein.

FIG. 17A is an EMSA shows binding of recombinant bHLH proteins to the radiolabeled probes. CR8 bHLH protein strongly binds to the Class B (CACGTG, lane 3) and the Class C (CACGCG, lane 4) sites, and weakly to the N box (CACNAG, lane 5) sequence but not to the Class A (CACCTG, lane 2) site. Binding of the bHLH region of da protein to the Class A site is shown as control (lane 1). As shown in FIG. 17A, CR8 bHLH bound to the Class B and the Class C probes, but only weakly to the N-box probe, and not at all to the Class A probe. However, the control da bHLH protein effectively recognized and bound to the same Class A probe.

To examine the relative binding affinity, a large excess of non-labeled oligonucleotide was added to the reaction as competitor. FIG. 17B shows competition of the binding of CR8 bHLH to the Class B sites. 0.5 ng of the radiolabeled Class B probe was incubated with CR8 bHLH in the absence (lane 1) or the presence (lanes 2 to 7) of either 25 ng (50-fold excess; lanes 2, 4 and 6) and 250 ng (500-fold excess; lanes 3, 5 and 7) of unlabeled competitors. FIG. 17B demonstrates that the binding of CR8 bHLH to the radiolabeled Class B site can be abolished partially by a 50-fold excess, and completely by a 500-fold excess of Class B site (lanes 2 and 3), while a 500-fold excess of Class C site only partially displaced CR8 bHLH from the labeled Class B probe (lanes 4 and 5) and the N-box sequence did not affect the binding at all (lanes 6 and 7). Thus, since all these experiments were done in the absence of other HLH proteins, it appears that CR8 bHLH bound to the Class B sequence as a homodimer with the highest affinity.

The CR8 gene encodes a novel bHLH protein that appears to fit into a class by itself. Other than c-myc, CR8 is the first bHLH-containing protein found to be induced by cytokines. Also, from its predicted amino acid sequence, CR8 clearly contains a bHLH motif most closely related to the hairy family, but the amino acid sequence of the basic region differs from other hairy-related proteins: the position of the proline residue is N-terminal to the defining proline of the hairy-related proteins, and CR8 lacks the C-terminal WRPW sequence found in all other hairy-related-related proteins. These differences in the amino acid sequence, especially of the basic region, most likely account for the unique binding specificity of the CR8 bHLH domain. Instead of preferring Class C sites according to the other hairy-related family members (Ohsako, S. et al. (1994) *Genes & Dev* 8:2743–275572; Van Doren, M. et al. (1994) *Genes & Dev* 8:2729–2742), CR8 binds preferentially to Class B sites.

The identification of CR8 as a bHLH protein, thereby functioning, most likely, as a regulator of subsequent gene expression stimulated by IL-2, provides a link between the immediate biochemical events triggered by cytokine receptors and the subsequent events of proliferation and/or differentiation. Thus far, IL-2 has been found to activate the serine/threonine kinase proto-oncogene Raf-1 (Turner, B. et al. (1991) Proc. Natl. Acad. Sci. USA 88:1227–1231; Zmuidzinas, A. et al. (1991) Mol. Cell Biol. 11:2794–2803) and the tyrosine-specific kinases JAK 1 and JAK 3 (Beadling, C. et al. (1994) EMBO J. 13:5605–5615; Miyazaki, T. et al. (1994) *Science* 266:1045–1047; Russell, S. M. et al. (1994) *Science* 266:1042–1045).

From the results described herein comparing the effects of IFNa and forskolin on CR8 and c-myc gene expression, the regulation of these two bHLH genes is clearly distinct. It is also of interest that although IFNβ antagonizes IL-2-promoted cell cycle progression, it promotes the expression of both CR8 and c-myc. Indeed, induction of c-myc by IFNβ was unexpected, as it was previously reported to be suppressed by IFNs (Einat, M. et al. (1985) *Nature* 313:597–600). The bHLH region of CR8 is most homologous to that of hairy and the bHLH proteins of the E(spl)-C. In Drosophila, the hairy-related bHLH proteins function as transcriptional repressors, and this activity requires the basic DNA binding region, as well as the interaction with a non-HLH protein termed groucho (gro) via the C-terminal WRPW motif (Paroush, Z. et al. (1994) *Cell* 79:805–815). Although mammalian homologues of gro have been identified (Stifani, S. et al. (1992) *Nat. Genet.* 2:119–127), they are not likely to interact with CR8 because CR8 lacks the WRPW motif.

The results described herein indicate that CR8 recombinant protein binds to Class B E-box sites as a homodimer.

This result is consistent with the predictions from DNA-bHLH protein co-crystals (Ferr-D'Amar, A. R. et al. (1994) *EMBO J.* 13:180–189; Ferr-D'Amar, A. R. et al. (1993) *Nature* 363:38–45). However, it is noteworthy in that CR8 is the first bHLH vertebrate protein without a leucine zipper (LZ) motif found to bind Class B sites. Protein dimerization is more selective than DNA binding, but currently no rules are available that predict the dimerization preference of any given HLH proteins. Even so, a Class A-binding protein seems to form DNA binding heterodimers only with other Class A proteins, and a bHLH protein with a LZ does not form heterodimers with those without LZs (Blackwood, E. M. et al. (1991) *Science* 251:1211–1217; Prendergast, G. C. et al. (1991) *Cell* 65:395–407). Therefore, if CR8 does form heterodimers, the most likely partner is a class B-binding bHLH protein without a LZ.

Although CR8 is most homologous to hairy in its bHLH domain, its preference for Class B E-box binding sites rather than class C sites, and its lack of a C-terminal WPRW motif, clearly sets CR8 apart and does not predict necessarily that CR8 may act as a transcriptional repressor as do hairy-related proteins. Recently, Id proteins that lack a basic region have been shown to favor proliferation, presumably by forming heterodimers with differentiation inducing bHLH proteins, thereby preventing DNA binding and transcriptional activation of genes that program differentiation (Barone, M. V. et al. (1994) *Proc. Natl. Acad. Sci. USA* 91:4985–4988; Hara, E. et al. (1994) *J. Biol. Chem.* 269:2139–2145; Iavarone, A. et al. (1994) *Genes & Dev* 1270–1284). Therefore, CR8 could promote proliferation by suppressing differentiation by either of these transcriptional repressor mechanisms. Alternatively, CR8 could also activate transcription like the bHLH-LZ Myc family.

Equivalents

Those skilled in the art will recognize, or be able to ascertain using no more than routine experimentation, many equivalents of the specific embodiments of the invention described herein. Such equivalents are intended to be encompassed by the following claims.

SEQUENCE LISTING (1) GENERAL INFORMATION:

(iii) NUMBER OF SEQUENCES: 35

(2) INFORMATION FOR SEQ ID NO:1:

(i) SEQUENCE CHARACTERISTICS:
      (A) LENGTH: 2406 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 116..722

(xi) SEQUENCE DESCRIPTION: SEQ ID NO:1:

```
AACCCAACCG CAGTTGACTA GCACCTGCTA CCGCGCCTTT GCTTCCTGGC GCACGCGGAG        60

CCTCCTGGAG CCTGCCACCA TCCTGCCTAC TACGTGCTGC CCTGCGCCCG CAGCC ATG       118

TGC CGC ACC CTG GCC GCC TTC CCC ACC ACC TGC CTG GAG AGA GCC AAA        166

GAG TTC AAG ACA CGT CTG GGG ATC TTT CTT CAC AAA TCA GAG CTG GGC        214

TGC GAT ACT GGG AGT ACT GGC AAG TTC GAG TGG GGC AGT AAA CAC AGC        262

AAA GAG AAT AGA AAC TTC TCA GAA GAT GTG CTG GGG TGG AGA GAG TCG        310

TTC GAC CTG CTG CTG AGC AGT AAA AAT GGA GTG GCT GCC TTC CAC GCT        358

TTC CTG AAG ACA GAG TTC AGT GAG GAG AAC CTG GAG TTC TGG CTG GCC        406

TGT GAG GAG TTC AAG AAG ATC CGA TCA GCT ACC AAG CTG GCC TCC AGG        454

GCA CAC CAG ATC TTT GAG GAG TTC ATT TGC AGT GAG GCC CCT AAA GAG        502

GTC AAC ATT GAC CAT GAG ACC CGC GAG CTG ACG AGG ATG AAC CTG CAG        550

ACT GCC ACA GCC ACA TGC TTT GAT GCG GCT CAG GGG AAG ACA CGT ACC        598

CTG ATG GAG AAG GAC TCC TAC CCA CGC TTC CTG AAG TCG CCT GCT TAC        646

CGG GAC CTG GCT GCC CAA GCC TCA GCC GCC TCT GCC ACT CTG TCC AGC        694

TGC AGC CTG GAC CAG CCC TCA CAC ACC T GAGTCTCCAC GGCAGTGAGG            742
```

```
AAGCCAGCCG GGAAGAGAGG TTGAGTCACC CATCCCCGAG GTGGCTGCCC CTGTGTGGGA       802

GGCAGGTTCT GCAAAGCAAG TGCAAGAGGA CAAAAAAAAA AAAAAAAAAA AAAAATGCGC       862

TCCAGCAGCC TGTTTGGGAA GCAGCAGTCT CTCCTTCAGA TACTGTGGGA CTCATGCTGG       922

AGAGGAGCCG CCCACTTCCA GGACCTGTGA ATAAGGGCTA ATGATGAGGG TTGGTGGGGC       982

TCTCTGTGGG GCAAAAAGGT GGTATGGGGG TTAGCACTGG CTCTCGTTCT CACCGGAGAA      1042

GGAAGTGTTC TAGTGTGGTT TAGGAAACAT GTGGATAAAG GGAACCATGA AAATGAGAGG      1102

AGGAAAGACA TCCAGATCAG CTGTTTTGCC TGTTGCTCAG TTGACTCTGA TTGCATCCTG      1162

TTTTCCTAAT TCCCAGACTG TTCTGGGCAC GGAAGGGACC CTGGATGTGG AGTCTTCCCC      1222

TTTGGCCCTC CTCACTGGCC TCTGGGCTAG CCCAGAGTCC CTTAGCTTGT ACCTCGTAAC      1282

ACTCCTGTGT GTCTGTCCAG CCTTGCAGTC ATGTCAAGGC CAGCAAGCTG ATGTGACTCT      1342

TGCCCCATGC GAGATATTTA TACCTCAAAC ACTGGCCTGT GAGCCCTTTC CAAGTCAGTG      1402

GAGAGCCCTG AAAGGAGCCT CACTTGAATC CAGCTCAGTG CTCTGGGTGG CCCCCTGCAG      1462

GTGCCCCCTG ACCCTGCGTT GCAGCAGGGT CCACCTGTGA GCAGGCCCGC CCTGGGCCCT      1522

CTTCCTGGAT GTGCCCTCTC TGAGTTCTGT GCTGTCTCTT GGAGGCAGGG CCCAGGAGAA      1582

CAAAGTGTGG AGGCCTCGGG GAGTGACTTT TCCAGCTCTC ATGCCCCGCA GTGTGGAACA      1642

AGGCAGAAAA GGATCCTAGG AAATAAGTCT CTTGGCGGTC CCTGAGAGTC CTGCTGAAAT      1702

CCAGCCAGTG TTTTTTGTGG TATGAGAACA GCCAAAAAGA GATGCCCCGA GATAGAAGGG      1762

GAGCCTTGTG TTTCTTTCCT GCAGACGTGA GATGAACACT GGAGTGGGCA GAGGTGGCCC      1822

AGGACCATGA CACCCTTAGA GTGCAGAAGC TGGGGGAGA GGCTGCTTCG AAGGGCAGGA      1882

CTGGGGATAA TCAGAACCTG CCTGTCACCT CAGGGCATCA CTGAACAAAC ATTTCCTGAT      1942

GGGAACTCCT GCGGCAGAGC CCAGGCTGGG GAAGTGAACT ACCCAGGGCA GCCCCTTTGT      2002

GGCCCAGGAT AATCAACACT GTTCTCTCTG TACCATGAGC TCCTCAGGA GATTATTTAA      2062

GTGTATTGTA TCATTGGTTT CTGTGATTG TCATAACATT GTTTTTGTTA CTGTTGGTGC      2122

TGTTGTTATT TATTATTGTA ATTTCAGTTT GCCTCTACTG GAGAATCTCA GCAGGGGTTT      2182

CAGCCTGACT GTCTCCCTTT CTCTACCAGA CTCTACCTCT GAATGTGCTG GGAACCTCTT      2242

GGAGCCTGTC AGGAACTCCT CACTGTTTAA ATATTTAGGT ATTGTGACAA ATGGAGCTGG      2302

TTTCCTAGAA ATGAATGATG TTTGCAATCC CCATTTTCCT GTTTCAGCAT GTTATATTCT      2362

TATGAAATAA AAGCCCAAGT CCAATATGAA AAAAAAAAA AAAA                        2406

(2) INFORMATION FOR SEQ ID NO:2:

(i) SEQUENCE CHARACTERISTICS:
        (A) LENGTH: 202 amino acids
        (B) TYPE: amino acid
        (D) TOPOLOGY: linear (ii) MOLECULE TYPE: protein (xi) SEQUENCE DESCRIPTION: SEQ ID NO:2:

Met Cys Arg Thr Leu Ala Ala Phe Pro Thr Thr Cys Leu Glu Arg Ala
 1               5                  10                  15

Lys Glu Phe Lys Thr Arg Leu Gly Ile Phe Leu His Lys Ser Glu Leu
            20                  25                  30

Gly Cys Asp Thr Gly Ser Thr Gly Lys Phe Glu Trp Gly Ser Lys His
        35                  40                  45

Ser Lys Glu Asn Arg Asn Phe Ser Glu Asp Val Leu Gly Trp Arg Glu
    50                  55                  60
```

```
Ser Phe Asp Leu Leu Leu Ser Lys Asn Gly Val Ala Ala Phe His
 65                  70                  75                  80

Ala Phe Leu Lys Thr Glu Phe Ser Glu Glu Asn Leu Glu Phe Trp Leu
                 85                  90                  95

Ala Cys Glu Glu Phe Lys Lys Ile Arg Ser Ala Thr Lys Leu Ala Ser
            100                 105                 110

Arg Ala His Gln Ile Phe Glu Glu Phe Ile Cys Ser Glu Ala Pro Lys
        115                 120                 125

Glu Val Asn Ile Asp His Glu Thr Arg Glu Leu Thr Arg Met Asn Leu
    130                 135                 140

Gln Thr Ala Thr Ala Thr Cys Phe Asp Ala Ala Gln Gly Lys Thr Arg
145                 150                 155                 160

Thr Leu Met Glu Lys Asp Ser Tyr Pro Arg Phe Leu Lys Ser Pro Ala
                165                 170                 175

Tyr Arg Asp Leu Ala Ala Gln Ala Ser Ala Ala Ser Ala Thr Leu Ser
            180                 185                 190

Ser Cys Ser Leu Asp Gln Pro Ser His Thr
            195                 200 202
```

(2) INFORMATION FOR SEQ ID NO:3:

(i) SEQUENCE CHARACTERISTICS:
        (A) LENGTH: 1223 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 171..351

(xi) SEQUENCE DESCRIPTION: SEQ ID NO:3:

```
ATTTAGAGCA ACTCAGGAAA TAGGTGCACA CAAGCAAACC ATGTGGTTAA AGCCTTTGGA    60

ACTGGTTTGA GCAAAGCTGT AGGTGATTTG ACAAAATCAT CTGCAAAACC AGATTTCTAA   120

CACCTCCCTG CTGTGTATCT CATTTCTGCT GATGTGTGGT GCTTCATAAG ATG GGG     176

ACG TTA AGC ATG CAG CAA CTA CAG TCA TTT GTT CTC AGA GGT CTG GAC    224

CAA AGA GAA ACA AGA AAA GCT GGA GTC ACA CTA CCA AAG GCC GAA GCT    272

GAG CAA CAG AGC TCT GGA GTC AGC TGC CTG GGT TCA GCA TGC AGC GCT    320

GCC GTG GAC GAT CTG TCT CTC TTG CAT ATA T GACTTACCAG TTTTACTTTC    371

AGTCTCTCCA TTTCTAATTA AATGAGATGC AGAAATGCTG GTGCCTTGCT ATGATGTTTG   431

CAGTTATTAT TTCTAGGAAA AAAAATATTA TTGTTACTCA GTATCTGGTC TAGCTACTTG   491

GACAACTGGA CTATCCCCCT CCTTTCAAGG GAGGGCAAAG CATTTCAGAA AGAACTAAG   551

TGCTATTTCT CTGCTTCAGG AATGTCTCCC GTATGTAAAA GAATGTGGCT TCAGGGAGTA   611

GCATGTGTTG TAAAGGTGGA TGGGTCTAAC TTCATGGACA GCTCTGACAT CCACTAGCTA   671

TGCCACCTGA TGCAAACCAC TTGGGCTGTC TGCAGTTTCG TTTATCTTTC TGGAATTGGT   731

AATAACAACC ACCTGGCAAG ATCACTGTTA TGAATACGGA GGATCAAAGT TGTGAAGTTA   791

TTTTGTAAAG TGAAATGTTC TGAAAAATGG ATTTTAACAG TGTCAGCGAA AAGTAGATTT   851

TTGACATTTA TCAAGAGTTC AGCTAATGAA AACAAGTATG GATAATAGTT ACATAGAACT   911

GTCTACTTTA CTCAGTACTT TAGCATATGC TATTATATTT AATCTTCTTA AAAAGTAGGA   971

AATTATACAA GCCATGTATT GATATTATTG TGGTGGTTGT CGTTCTCAAT TACACACTGA  1031
```

```
ATATTAAGAC CTCTCAGGTA GCAGCTGGAA GGACATTGTA TCCAGTTTCC TGATTGTTTT       1091

CAATGGAATA ATCATGTATA CATGCACTAC TAATGAGACA ATGGTGATTC TAAAAGCTTA       1151

ATCAGGGGA CTTTTGTGTA TTCCAAATCT ACTAAAAATA AAGAAACACA GAAATGAGAA        1211

AAAAAAAAAA AA                                                           1223
```

(2) INFORMATION FOR SEQ ID NO:4:

(i) SEQUENCE CHARACTERISTICS:
        (A) LENGTH: 60 amino acids
        (B) TYPE: amino acid
        (D) TOPOLOGY: linear (ii) MOLECULE TYPE: protein (xi) SEQUENCE DESCRIPTION: SEQ ID NO:4:

```
Met Gly Thr Leu Ser Met Gln Gln Leu Gln Ser Phe Val Leu Arg Gly
 1               5                  10                  15

Leu Asp Gln Arg Glu Thr Arg Lys Ala Gly Val Thr Leu Pro Lys Ala
                20                  25                  30

Glu Ala Glu Gln Gln Ser Ser Gly Val Ser Cys Leu Gly Ser Ala Cys
            35                  40                  45

Ser Ala Ala Val Asp Asp Leu Ser Leu Leu His Ile
            50                  55                  60
```

(2) INFORMATION FOR SEQ ID NO:5:

(i) SEQUENCE CHARACTERISTICS:
        (A) LENGTH: 2450 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 229..1303

(xi) SEQUENCE DESCRIPTION: SEQ ID NO:5:

```
CGCGGGAGCC TCGAGCGCCG CTCGGATGCA GAAGCCGAGC CGCCACTCGG CGCGCGGTGG        60

GAGACCCAGG GCAAGCCGCC GTCGGCGCGC TGGGTGCGGG AAGGGGGCTC TGGATTTCGG       120

TCCCTCCCCT TTTTCCTCTG AGTCTCGGAA CGCTCCAGAT CTCAGACCCT CTTCCTCCCA       180

GGTAAAGGCC GGGAGAGGAG GGCGCATCTC TTTTCCAGGC ACCCCACC ATG GGA AAT        237

GCC TCC AAT GAC TCC CAG TCT GAG GAC TGC GAG ACG CGA CAG TGG TTT        285

CCC CCA GGC GAA AGC CCA GCC ATC AGT TCC GTC ATG TTC TCG GCC GGG        333

GTG CTG GGG AAC CTC ATA GAA CTG GCG CTG CTG GCG CGC CGC TGG CAG        381

GGG GAC GTG GGG TGC AGC GCC GGC CGT AGG AGC TCC CTC TCC TTG TTC        429

CAC GTG CTG GTG ACC GAG CTG GTG TTC ACC GAC CTG CTC GGG ACC TGC        477

CTC ATC AGC CCA GTG GTA CTG GCT TCG TAC GCG CGG AAC CAG ACC CTG        525

GTG GCA CTG GCG CCC GAG AGC CGC GCG TCC ACC TAC TTC GCT TTC GCC        573

ATG ACC TTC TTC AGC CTG GCC ACG ATG CTC ATG CTC TTC ACC ATG GCC        621

CTG GAG CGC TAC CTC TCG ATC GGG CAC CCC TAC TTC TAC CAG CGC CGC        669

GTC TCG CGC TCC GGG GGC CTG GCC GTG CTG CCT GTC ATC TAT GCA GTC        717

TCC CTG CTC TTC TGC TCA CTG CCG CTG CTG GAC TAT GGG CAG TAC GTC        765

CAG TAC TGC CCC GGG ACC TGG TGC TTC ATC CGG CAC GGG CGG ACC GCT        813
```

| | |
|---|---:|
| TAC CTG CAG CTG TAC GCC ACC CTG CTG CTG CTT CTC ATT GTC TCG GTG | 861 |
| CTC GCC TGC AAC TTC AGT GTC ATT CTC AAC CTC ATC CGC ATG CAC CGC | 909 |
| CGA AGC CGG AGA AGC CGC TGC GGA CCT TCC CTG GGC AGT GGC CGG GGC | 957 |
| GGC CCC GGG GCC CGC AGG AGA GGG GAA AGG GTG TCC ATG GCG GAG GAG | 1005 |
| ACG GAC CAC CTC ATT CTC CTG GCT ATC ATG ACC ATC ACC TTC GCC GTC | 1053 |
| TGC TCC TTG CCT TTC ACG ATT TTT GCA TAT ATG AAT GAA ACC TCT TCC | 1101 |
| CGA AAG GAA AAA TGG GAC CTC CAA GCT CTT AGG TTT TTA TCA ATT AAT | 1149 |
| TCA ATA ATT GAC CCT TGG GTC TTT GCC ATC CTT AGG CCT CCT GTT CTG | 1197 |
| AGA CTA ATG CGT TCA GTC CTC TGT TGT CGG ATT TCA TTA AGA ACA CAA | 1245 |
| GAT GCA ACA CAA ACT TCC TGT TCT ACA CAG TCA GAT GCC AGT AAA CAG | 1293 |
| GCT GAC CTT T GAGGTCAGTA GTTTAAAAGT TCTTAGTTAT ATAGCATCTG | 1343 |
| GAAGATCATT TTGAAATTGT TCCTTGGAGA ATGAAAACA GTGTGTAAAC AAAATGAAGC | 1403 |
| TGCCCTAATA AAAGGAGTA TACAAACATT TAAGCTGTGG TCAAGGCTAC AGATGTGCTG | 1463 |
| ACAAGGCACT TCATGTAAAG TGTCAGAAGG AGCTACAAAA CCTACCCTCA GTGAGCATGG | 1523 |
| TACTTGGCCT TTGGAGGAAC AATCGGCTGC ATTGAAGATC CAGCTGCCTA TTGATTTAAG | 1583 |
| CTTTCCTGTT GAATGACAAA GTATGTGGTT TTGTAATTTG TTTGAAACCC CAAACAGTGA | 1643 |
| CTGTACTTTC TATTTTAATC TTGCTACTAC CGTTATACAC ATATAGTGTA CAGCCAGACC | 1703 |
| AGATTAAACT TCATATGTAA TCTCTAGGAA GTCAATATGT GGAAGCAACC AAGCCTGCTG | 1763 |
| TCTTGTGATC ACTTAGCGAA CCCTTTATTT GAACAATGAA GTTGAAAATC ATAGGCACCT | 1823 |
| TTTACTGTGA TGTTTGTGTA TGTGGGAGTA CTCTCATCAC TACAGTATTA CTCTTACAAG | 1883 |
| AGTGGACTCA GTGGGTTAAC ATCAGTTTTG TTTACTCATC CTCCAGGAAC TGCAGGTCAA | 1943 |
| GTTGTCAGGT TATTTATTTT ATAATGTCCA TATGCTAATA GTGATCAAGA AGACTTTAGG | 2003 |
| AATGGTTCTC TCAACAAGAA ATAATAGAAA TGTCTCAAGG CAGTTAATTC TCATTAATAC | 2063 |
| TCTTTATCCT ATTTCTGGGG GAGGATGTAC GTGGCCATGT ATGAAGCCAA ATATTAGGCT | 2123 |
| TAAAAACTGA AAAATCTGGT TCATTCTTCA GATATACTGG AACCCTTTTA AAGTTGATAT | 2183 |
| TGGGGCCATG AGTAAAATAG ATTTTATAAG ATGACTGTGT TGTACTAAAA TTCATCTGTC | 2243 |
| TATATTTTAT TTAGGGGACA TGGTTTGACT CATCTTATAT GGGAAACCAT GTAGCAGTGA | 2303 |
| GTCATATCTT AATATATTTC TAAATGTTTG GCATGTAAAC GTAAACTCAG CATCACAATA | 2363 |
| TTTCAGTGAA TTTGCACTGT TAATCATAG TTACTGTGTA AACTCATCTG AAATGTTACC | 2423 |
| AAAAATAAAC TATAAAACAA AATTTGA | 2450 |

(2) INFORMATION FOR SEQ ID NO:6:

(i) SEQUENCE CHARACTERISTICS:
        (A) LENGTH: 358 amino acids
        (B) TYPE: amino acid
        (D) TOPOLOGY: linear (ii) MOLECULE TYPE: protein (xi) SEQUENCE DESCRIPTION: SEQ ID NO:6:

Met Gly Asn Ala Ser Asn Asp Ser Gln Ser Glu Asp Cys Glu Thr Arg
 1               5                  10                  15

Gln Trp Phe Pro Pro Gly Glu Ser Pro Ala Ile Ser Ser Val Met Phe
            20                  25                  30

Ser Ala Gly Val Leu Gly Asn Leu Ile Glu Leu Ala Leu Leu Ala Arg

```
                    35                  40                  45
Arg Trp Gln Gly Asp Val Gly Cys Ser Ala Gly Arg Ser Ser Leu
     50                   55                  60

Ser Leu Phe His Val Leu Val Thr Glu Leu Val Phe Thr Asp Leu Leu
 65                  70                  75                  80

Gly Thr Cys Leu Ile Ser Pro Val Val Leu Ala Ser Tyr Ala Arg Asn
                     85                  90                  95

Gln Thr Leu Val Ala Leu Ala Pro Glu Ser Arg Ala Ser Thr Tyr Phe
                100                 105                 110

Ala Phe Ala Met Thr Phe Phe Ser Leu Ala Thr Met Leu Met Leu Phe
            115                 120                 125

Thr Met Ala Leu Glu Arg Tyr Leu Ser Ile Gly His Pro Tyr Phe Tyr
        130                 135                 140

Gln Arg Arg Val Ser Arg Ser Gly Gly Leu Ala Val Leu Pro Val Ile
145                 150                 155                 160

Tyr Ala Val Ser Leu Leu Phe Cys Ser Leu Pro Leu Leu Asp Tyr Gly
                165                 170                 175

Gln Tyr Val Gln Tyr Cys Pro Gly Thr Trp Cys Phe Ile Arg His Gly
            180                 185                 190

Arg Thr Ala Tyr Leu Gln Leu Tyr Ala Thr Leu Leu Leu Leu Leu Ile
        195                 200                 205

Val Ser Val Leu Ala Cys Asn Phe Ser Val Ile Leu Asn Leu Ile Arg
    210                 215                 220

Met His Arg Arg Ser Arg Arg Ser Arg Cys Gly Pro Ser Leu Gly Ser
225                 230                 235                 240

Gly Arg Gly Gly Pro Gly Ala Arg Arg Gly Glu Arg Val Ser Met
                245                 250                 255

Ala Glu Glu Thr Asp His Leu Ile Leu Leu Ala Ile Met Thr Ile Thr
            260                 265                 270

Phe Ala Val Cys Ser Leu Pro Phe Thr Ile Phe Ala Tyr Met Asn Glu
        275                 280                 285

Thr Ser Ser Arg Lys Glu Lys Trp Asp Leu Gln Ala Leu Arg Phe Leu
    290                 295                 300

Ser Ile Asn Ser Ile Ile Asp Pro Trp Val Phe Ala Ile Leu Arg Pro
305                 310                 315                 320

Pro Val Leu Arg Leu Met Arg Ser Val Leu Cys Cys Arg Ile Ser Leu
                325                 330                 335

Arg Thr Gln Asp Ala Thr Gln Thr Ser Cys Ser Thr Gln Ser Asp Ala
            340                 345                 350

Ser Lys Gln Ala Asp Leu
    355             358

(2) INFORMATION FOR SEQ ID NO:7:

(i) SEQUENCE CHARACTERISTICS:
        (A) LENGTH: 2946 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 215..2503

(xi) SEQUENCE DESCRIPTION: SEQ ID NO:7:

GGGGGGAAAG GAAAATAATA CAATTTCAGG GGAAGTCGCC TTCAGGTCTG CTGCTTTTTT    60
```

```
ATTTTTTTTT TTTTAATTAA AAAAAAAAAG GACATAGAAA ACATCAGTCT TGAACTTCTC         120

TTCAAGAACC CGGGCTGCAA AGGAAATCTC CTTTGTTTTT GTTATTTATG TGCTGTCAAG         180

TTTTGAAGTG GTGATCTTTA GACAGTGACT GAGT ATG GAT CAT TTG AAC GAG            232

GCA ACT CAG GGG AAA GAA CAT TCA GAA ATG TCT AAC AAT GTG AGT GAT          280

CCG AAG GGT CCA CCA GCC AAG ATT GCC CGC CTG GAG CAG AAC GGG AGC          328

CCG CTA GGA AGA GGA AGG CTT GGG AGT ACA GGT GCA AAA ATG CAG GGA          376

GTG CCT TTA AAA CAC TCG GGC CAT CTG ATG AAA ACC AAC CTT AGG AAA          424

GGA ACC ATG CTG CCA GTT TTC TGT GTG GTG GAA CAT TAT GAA AAC GCC          472

ATT GAA TAT GAT TGC AAG GAG GAG CAT GCA GAA TTT GTG CTG GTG AGA          520

AAG GAT ATG CTT TTC AAC CAG CTG ATC GAA ATG GCA TTG CTG TCT CTA          568

GGT TAT TCA CAT AGC TCT GCT GCC CAG GCC AAA GGG CTA ATC CAG GTT          616

GGA AAG TGG AAT CCA GTT CCA CTG TCT TAC GTG ACA GAT GCC CCT GAT          664

GCT ACA GTA GCA GAT ATG CTT CAA GAT GTG TAT CAT GTG GTC ACA TTG          712

AAA ATT CAG TTA CAC AGT TGC CCC AAA CTA GAA GAC TTG CCT CCC GAA          760

CAA TGG TCG CAC ACC ACA GTG AGG AAT GCT CTG AAG GAC TTA CTG AAA          808

GAT ATG AAT CAG AGT TCA TTG GCC AAG GAG TGC CCC CTT TCA CAG AGT          856

ATG ATT TCT TCC ATT GTG AAC AGT ACT TAC TAT GCA AAT GTC TCA GCA          904

GCA AAA TGT CAA GAA TTT GGA AGG TGG TAC AAA CAT TTC AAG AAG ACA          952

AAA GAT ATG ATG GTT GAA ATG GAT AGT CTT TCT GAG CTA TCC CAG CAA         1000

GGC GCC AAT CAT GTC AAT TTT GGC CAG CAA CCA GTT CCA GGG AAC ACA         1048

GCC GAG CAG CCT CCA TCC CCT GCG CAG CTC TCC CAT GGC AGC CAG CCC         1096

TCT GTC CGG ACA CCT CTT CCA AAC CTG CAC CCT GGG CTC GTA TCA ACA         1144

CCT ATC AGT CCT CAA TTG GTC AAC CAG CAG CTG GTG ATG GCT CAG CTG         1192

CTG AAC CAG CAG TAT GCA GTG AAT AGA CTT TTA GCC CAG CAG TCC TTA         1240

AAC CAA CAA TAC TTG AAC CAC CCT CCC CCT GTC AGT AGA TCT ATG AAT         1288

AAG CCT TTG GAG CAA CAG GTT TCG ACC AAC ACA GAG GTG TCT TCC GAA         1336

ATC TAC CAG TGG GTA CGC GAT GAA CTG AAA CGA GCA GGA ATC TCC CAG         1384

GCG GTA TTT GCA CGT GTG GCT TTT AAC AGA ACT CAG GGC TTG CTT TCA         1432

GAA ATC CTC CGA AAG GAA GAG GAC CCC AAG ACT GCA TCC CAG TCT TTG         1480

CTG GTA AAC CTT CGG GCT ATG CAG AAT TTC TTG CAG TTA CCG GAA GCT         1528

GAA AGA GAC CGA ATA TAC CAG GAC GAA AGG GAA AGG AGC TTG AAT GCT         1576

GCC TCG GCC ATG GGT CCT GCC CCC CTC ATC AGC ACA CCA CCC AGC CGT         1624

CCT CCC CAG GTG AAA ACA GCT ACT ATT GCC ACT GAA AGG AAT GGG AAA         1672

CCA GAG AAC AAT ACC ATG AAC ATT AAT GCT TCC ATT TAT GAT GAG ATT         1720

CAG CAG GAA ATG AAG CGT GCT AAA GTG TCT CAA GCA CTG TTT GCA AAG         1768

GTT GCA GCA ACC AAA AGC CAG GGA TGG TTG TGC GAG CTG TTA CGC TGG         1816

AAA GAA GAT CCT TCT CCA GAA AAC AGA ACC CTG TGG GAG AAC CTC TCC         1864

ATG ATC CGA AGG TTC CTC AGT CTT CCT CAG CCA GAA CGT GAT GCC ATT         1912

TAT GAA CAG GAG AGC AAC GCG GTG CAT CAC CAT GGC GAC AGG CCG CCC         1960

CAC ATT ATC CAT GTT CCA GCA GAG CAG ATT CAG CAA CAG CAG CAG CAA         2008
```

| | | | | | | | | | | | | | | | |
|---|---|---|---|---|---|---|---|---|---|---|---|---|---|---|---|
| CAG | CAA | CAG | CAG | CAG | CAG | CAG | CAG | CAG | GCA | CCG | CCG | CCT | CCA | CAG | CCA | 2056 |
| CAG | CAG | CAG | CCA | CAG | ACA | GGC | CCT | CGG | CTC | CCC | CCA | CGG | CAA | CCC | ACG | 2104 |
| GTG | GCC | TCT | CCA | GCA | GAG | TCA | GAT | GAG | GAA | AAC | CGA | CAG | AAG | ACC | CGG | 2152 |
| CCA | CGA | ACA | AAA | ATT | TCA | GTG | GAA | GCC | TTG | GGA | ATC | CTC | CAG | AGT | TTC | 2200 |
| ATA | CAA | GAC | GTG | GGC | CTG | TAC | CCT | GAC | GAA | GAG | GCC | ATC | CAG | ACT | CTG | 2248 |
| TCT | GCC | CAG | CTC | GAC | CTT | CCC | AAG | TAC | ACC | ATC | ATC | AAG | TTC | TTT | CAG | 2296 |
| AAC | CAG | CGG | TAC | TAT | CTC | AAG | CAC | CAC | GGC | AAA | CTG | AAG | GAC | AAT | TCC | 2344 |
| GGT | TTA | GAG | GTC | GAT | GTG | GCA | GAA | TAT | AAA | GAA | GAG | GAG | CTG | CTG | AAG | 2392 |
| GAT | TTG | GAA | GAG | AGT | GTC | CAA | GAT | AAA | AAT | ACT | AAC | ACC | CTT | TTT | TCA | 2440 |
| GTG | AAA | CTA | GAA | GAA | GAG | CTG | TCA | GTG | GAA | GGA | AAC | ACA | GAC | ATT | AAT | 2488 |

ACT GAT TTG AAA GAC TGAGATAAAA GTATTTGTTT CGTTCAACAG TGCCACTGGT 2543

ATTTACTAAC AAAATGAAAA GTCCACCTTG TCTTCTCTCA GAAAACCTTT GTTGTTCATT 2603

GTTTGGCCAA TGAACTTTCA AAAACTTGCA CAAACAGAAA AGTTGGAAAA GGATAATACA 2663

GACTGCACTA AATGTTTTCC TCTGTTTTAC AAACTGCTTG GCAGCCCAG GTGAAGCATC 2723

AAGGATTGTT TGGTATTAAA ATTTGTGTTC ACGGGATGCA CCAAAGTGTG TACCCCGTAA 2783

GCATGAAACC AGTGTTTTTT GTTTTTTTT TAGTTCTTAT TCCGGAGCCT CAAACAAGCA 2843

TTATACCTTC TGTGATTATG ATTTCCTCTC CTATAATTAT TTCTGTAGCA CTCCACACTG 2903

ATCTTTGGAA ACTTGCCCCT TATTTAAAAA AAAAAAAAAA AAA 2946

(2) INFORMATION FOR SEQ ID NO:8:

(i) SEQUENCE CHARACTERISTICS:
        (A) LENGTH: 763 amino acids
        (B) TYPE: amino acid
        (D) TOPOLOGY: linear (ii) MOLECULE TYPE: protein (xi) SEQUENCE DESCRIPTION: SEQ ID NO:8:

Met Asp His Leu Asn Glu Ala Thr Gln Gly Lys Glu His Ser Glu Met
 1               5                  10                  15

Ser Asn Asn Val Ser Asp Pro Lys Gly Pro Ala Lys Ile Ala Arg
            20                  25                  30

Leu Glu Gln Asn Gly Ser Pro Leu Gly Arg Gly Arg Leu Gly Ser Thr
        35                  40                  45

Gly Ala Lys Met Gln Gly Val Pro Leu Lys His Ser Gly His Leu Met
    50                  55                  60

Lys Thr Asn Leu Arg Lys Gly Thr Met Leu Pro Val Phe Cys Val Val
65                  70                  75                  80

Glu His Tyr Glu Asn Ala Ile Glu Tyr Asp Cys Lys Glu Glu His Ala
                85                  90                  95

Glu Phe Val Leu Val Arg Lys Asp Met Leu Phe Asn Gln Leu Ile Glu
            100                 105                 110

Met Ala Leu Leu Ser Leu Gly Tyr Ser His Ser Ser Ala Ala Gln Ala
        115                 120                 125

Lys Gly Leu Ile Gln Val Gly Lys Trp Asn Pro Val Pro Leu Ser Tyr
    130                 135                 140

Val Thr Asp Ala Pro Asp Ala Thr Val Ala Asp Met Leu Gln Asp Val
145                 150                 155                 160

Tyr His Val Val Thr Leu Lys Ile Gln Leu His Ser Cys Pro Lys Leu

```
                165                 170                 175
Glu Asp Leu Pro Pro Glu Gln Trp Ser His Thr Thr Val Arg Asn Ala
                180                 185                 190
Leu Lys Asp Leu Leu Lys Asp Met Asn Gln Ser Ser Leu Ala Lys Glu
                195                 200                 205
Cys Pro Leu Ser Gln Ser Met Ile Ser Ser Ile Val Asn Ser Thr Tyr
                210                 215                 220
Tyr Ala Asn Val Ser Ala Ala Lys Cys Gln Glu Phe Gly Arg Trp Tyr
225                 230                 235                 240
Lys His Phe Lys Lys Thr Lys Asp Met Met Val Glu Met Asp Ser Leu
                245                 250                 255
Ser Glu Leu Ser Gln Gln Gly Ala Asn His Val Asn Phe Gly Gln Gln
                260                 265                 270
Pro Val Pro Gly Asn Thr Ala Glu Gln Pro Ser Pro Ala Gln Leu
                275                 280                 285
Ser His Gly Ser Gln Pro Ser Val Arg Thr Pro Leu Pro Asn Leu His
                290                 295                 300
Pro Gly Leu Val Ser Thr Pro Ile Ser Pro Gln Leu Val Asn Gln Gln
305                 310                 315                 320
Leu Val Met Ala Gln Leu Leu Asn Gln Gln Tyr Ala Val Asn Arg Leu
                325                 330                 335
Leu Ala Gln Gln Ser Leu Asn Gln Gln Tyr Leu Asn His Pro Pro Pro
                340                 345                 350
Val Ser Arg Ser Met Asn Lys Pro Leu Glu Gln Gln Val Ser Thr Asn
                355                 360                 365
Thr Glu Val Ser Ser Glu Ile Tyr Gln Trp Val Arg Asp Glu Leu Lys
                370                 375                 380
Arg Ala Gly Ile Ser Gln Ala Val Phe Ala Arg Val Ala Phe Asn Arg
385                 390                 395                 400
Thr Gln Gly Leu Leu Ser Glu Ile Leu Arg Lys Glu Asp Pro Lys
                405                 410                 415
Thr Ala Ser Gln Ser Leu Leu Val Asn Leu Arg Ala Met Gln Asn Phe
                420                 425                 430
Leu Gln Leu Pro Glu Ala Glu Arg Asp Arg Ile Tyr Gln Asp Glu Arg
                435                 440                 445
Glu Arg Ser Leu Asn Ala Ala Ser Ala Met Gly Pro Ala Pro Leu Ile
                450                 455                 460
Ser Thr Pro Pro Ser Arg Pro Pro Gln Val Lys Thr Ala Thr Ile Ala
465                 470                 475                 480
Thr Glu Arg Asn Gly Lys Pro Glu Asn Thr Met Asn Ile Asn Ala
                485                 490                 495
Ser Ile Tyr Asp Glu Ile Gln Gln Glu Met Lys Arg Ala Lys Val Ser
                500                 505                 510
Gln Ala Leu Phe Ala Lys Val Ala Ala Thr Lys Ser Gln Gly Trp Leu
                515                 520                 525
Cys Glu Leu Leu Arg Trp Lys Glu Asp Pro Ser Pro Glu Asn Arg Thr
                530                 535                 540
Leu Trp Glu Asn Leu Ser Met Ile Arg Arg Phe Leu Ser Leu Pro Gln
545                 550                 555                 560
Pro Glu Arg Asp Ala Ile Tyr Glu Gln Glu Ser Asn Ala Val His His
                565                 570                 575
His Gly Asp Arg Pro Pro His Ile Ile His Val Pro Ala Glu Gln Ile
                580                 585                 590
```

```
Gln Gln Gln Gln Gln Gln Gln Gln Gln Gln Gln Gln Gln Ala
        595                 600                 605
Pro Pro Pro Pro Gln Pro Gln Gln Pro Gln Thr Gly Pro Arg Leu
610                 615                 620
Pro Pro Arg Gln Pro Thr Val Ala Ser Pro Ala Glu Ser Asp Glu Glu
625                 630                 635                 640
Asn Arg Gln Lys Thr Arg Pro Arg Thr Lys Ile Ser Val Glu Ala Leu
                645                 650                 655
Gly Ile Leu Gln Ser Phe Ile Gln Asp Val Gly Leu Tyr Pro Asp Glu
                660                 665                 670
Glu Ala Ile Gln Thr Leu Ser Ala Gln Leu Asp Leu Pro Lys Tyr Thr
                675                 680                 685
Ile Ile Lys Phe Phe Gln Asn Gln Arg Tyr Tyr Leu Lys His His Gly
                690                 695                 700
Lys Leu Lys Asp Asn Ser Gly Leu Glu Val Asp Val Ala Glu Tyr Lys
705                 710                 715                 720
Glu Glu Glu Leu Leu Lys Asp Leu Glu Glu Ser Val Gln Asp Lys Asn
                725                 730                 735
Thr Asn Thr Leu Phe Ser Val Lys Leu Glu Glu Leu Ser Val Glu
                740                 745                 750
Gly Asn Thr Asp Ile Asn Thr Asp Leu Lys Asp
            755                 760     763

(2) INFORMATION FOR SEQ ID NO:9:

(i) SEQUENCE CHARACTERISTICS:
        (A) LENGTH: 1960 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 112..886

(xi) SEQUENCE DESCRIPTION: SEQ ID NO:9:

CGCCCGCGCG CCCCGGGAGC CTACCCAGCA CGCGCTCCGC GCCCACTGGT TCCCTCCAGC        60

CGCCGCCGTC CAGCCGAGTC CCCACTCCGG AGTCGCCGCT GCCGCGGGGA C ATG GTC       117

CTC TGC GTT CAG GGA CCT CGT CCT TTG CTG GCT GTG GAG CGG ACT GGG       165

CAG CGG CCC CTG TGG GCC CCG TCC CTG GAA CTG CCC AAG CCA GTC ATG       213

CAG CCC TTG CCT GCT GGG GCC TTC CTC GAG GAG GTG GCA GAG GGT ACC       261

CCA GCC CAG ACA GAG AGT GAG CCA AAG GTG CTG GAC CCA GAG GAG GAT       309

CTG CTG TGC ATA GCC AAG ACC TTC TCC TAC CTT CGG GAA TCT GGC TGG       357

TAT TGG GGT TCC ATT ACG GCC AGC GAG GCC CGA CAA CAC CTG CAG AAG       405

ATG CCA GAA GGC ACG TTC TTA GTA CGT GAC AGC ACG CAC CCC AGC TAC       453

CTG TTC ACG CTG TCA GTG AAA ACC ACT CGT GGC CCC ACC AAT GTA CGC       501

ATT GAG TAT GCC GAC TCC AGC TTC GTT CTG GAC TCC AAC TGC TTG TCC       549

AGG CCA CGC ATC CTG GCC TTT CCG GAT GTG GTC AGC CTT GTG CAG CAC       597

TAT GTG GCC TCC TGC ACT GCT GAT ACC CGA AGC GAC AGC CCC GAT CCT       645

GCT CCC ACC CCG GCC CTG CCT ATG CCT AAG GAG GAT GCG CCT AGT GAC       693

CCA GCA CTG CCT GCT CCT CCA CCA GCC ACT GCT GTA CAC CTA AAA CTG       741
```

```
GTG CAG CCC TTT GTA CGC AGA AGA AGT GCC CGC AGC CTG CAA CAC CTG          789

TGC CGC CTT GTC ATC AAC CGT CTG GTG GCC GAC GTG GAC TGC CTG CCA          837

CTG CCC CGG CGC ATG GCC GAC TAC CTC CGA CAG TAC CCC TTC CAG CTC T        886

GACTGTACGG GGCAATCTGC CCACCCTCAC CCAGTCGCAC CCTGGAGGGG ACATCAGCCC        946

CAGCTGGACT TGGGCCCCCA CTGTCCCTCC TCCAGGCATC CTGGTGCCTG CATACCTCTG       1006

GCAGCTGGCC CAGGAAGAGC CAGCAAGAGC AAGGCATGGG AGAGGGGAGG TGTCACACAA       1066

CTTGGAGGTA AATGCCCCCA GGCCGCATGT GGCTTCATTA TACTGAGCCA TGTGTCAGAG       1126

GATGGGGAGA CAGGCAGGAC CTTGTCTCAC CTGTGGGCTG GCCCAGACCT CCACTCGCT        1186

TGCCTGCCCT GGCCACCTGA ACTGTATGGG CACTCTCAGC CCTGGTTTTT CAATCCCCAG       1246

GGTCGGGTAG GACCCCTACT GGCAGCCAGC CTCTGTTTCT GGGAGGATGA CATGCAGAGG       1306

AACTGAGATC GACAGTGACT AGTGACCCCT TGTTGAGGGG TAAGCCAGGC TAGGGGACTG       1366

CACAATTATA CACTCCTGAG CCCTGGTAGT CCAGAGACCC CAACTCTGCC CTGGCTTCTC       1426

TGGTTCTTCC CTGTGGAAAG CCCATCCTGA GACATCTTGC TGGAACCAAG GCAATCCTGG       1486

ATGTCCTGGT ACTGACCCAC CCGTCTGTGA ATGTGTCCAC TCTCTTCTGC CCCCAGCCAT       1546

ATTTGGGGAG GATGGACAAC TACAATAGGT AAGAAAATGC AGCCGGAGCC TCAGTCCCCA       1606

GCAGAGCCTG TGTCTCACCC CCTCACAGGA CAGAGCTGTA TCTGCATAGA GCTGGTCTCA       1666

CTGTGGCGCA GGCCCCGGGG GGAGTGCCTG TGCTGTCAGG AAGAGGGGGT GCTGGTTTGA       1726

GGGCCACCAC TGCAGTTCTG CTAGGTCTGC TTCCTGCCCA GGAAGGTGCC TGCACATGAG       1786

AGGAGAGAAA TACACGTCTG ATAAGACTTC ATGAAATAAT AATTATAGCA AGAACAGTT        1846

TGGTGGTCTT TTCTCTTCCA CTGATTTTTC TGTAATGACA TTATACCTTT ATTACCTCTT       1906

TATTTTATTA CCTCTATAAT AAAATGATAC CTTTCATGTA AAAAAAAAA AAAA             1960
```

(2) INFORMATION FOR SEQ ID NO:10:

(i) SEQUENCE CHARACTERISTICS:
        (A) LENGTH: 258 amino acids
        (B) TYPE: amino acid
        (D) TOPOLOGY: linear (ii) MOLECULE TYPE: protein (xi) SEQUENCE DESCRIPTION: SEQ ID NO:10:

```
Met Val Leu Cys Val Gln Gly Pro Arg Pro Leu Leu Ala Val Glu Arg
  1               5                  10                  15

Thr Gly Gln Arg Pro Leu Trp Ala Pro Ser Leu Glu Leu Pro Lys Pro
                 20                  25                  30

Val Met Gln Pro Leu Pro Ala Gly Ala Phe Leu Glu Glu Val Ala Glu
             35                  40                  45

Gly Thr Pro Ala Gln Thr Glu Ser Glu Pro Lys Val Leu Asp Pro Glu
         50                  55                  60

Glu Asp Leu Leu Cys Ile Ala Lys Thr Phe Ser Tyr Leu Arg Glu Ser
 65                  70                  75                  80

Gly Trp Tyr Trp Gly Ser Ile Thr Ala Ser Glu Ala Arg Gln His Leu
                 85                  90                  95

Gln Lys Met Pro Glu Gly Thr Phe Leu Val Arg Asp Ser Thr His Pro
                100                 105                 110

Ser Tyr Leu Phe Thr Leu Ser Val Lys Thr Thr Arg Gly Pro Thr Asn
            115                 120                 125

Val Arg Ile Glu Tyr Ala Asp Ser Ser Phe Arg Leu Asp Ser Asn Cys
        130                 135                 140
```

```
Leu Ser Arg Pro Arg Ile Leu Ala Phe Pro Asp Val Val Ser Leu Val
145                 150                 155                 160

Gln His Tyr Val Ala Ser Cys Thr Ala Asp Thr Arg Ser Asp Ser Pro
            165                 170                 175

Asp Pro Ala Pro Thr Pro Ala Leu Pro Met Pro Lys Glu Asp Ala Pro
        180                 185                 190

Ser Asp Pro Ala Leu Pro Ala Pro Pro Ala Thr Ala Val His Leu
    195                 200                 205

Lys Leu Val Gln Pro Phe Val Arg Arg Ser Ala Arg Ser Leu Gln
210                 215                 220

His Leu Cys Arg Leu Val Ile Asn Arg Leu Val Ala Asp Val Asp Cys
225                 230                 235                 240

Leu Pro Leu Pro Arg Arg Met Ala Asp Tyr Leu Arg Gln Tyr Pro Phe
                245                 250                 255

Gln Leu
    258
```

(2) INFORMATION FOR SEQ ID NO:11:

(i) SEQUENCE CHARACTERISTICS:
        (A) LENGTH: 1065 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 98..575

(xi) SEQUENCE DESCRIPTION: SEQ ID NO:11:

```
GTGGGTGCGC CGTGCTGAGC TCTGGCTGTC AGTGTGTTCG CCCGCGTCCC CTCCGCGCTC      60

TCCGCTTGTG GATAACTAGC TGCTGGTTGA TCGCACT ATG ACT CTG GAA GAA GTC     115

CGC GGC CAG GAC ACA GTT CCG GAA AGC ACA GCC AGG ATG CAG GGT GCC      163

GGG AAA GCG CTG CAT GAG TTG CTG CTG TCG GCG CAG CGT CAG GGC TGC      211

CTC ACT GCC GGC GTC TAC GAG TCA GCC AAA GTC TTG AAC GTG GAC CCC      259

GAC AAT GTG ACC TTC TGT GTG CTG GCT GCG GGT GAG GAG GAC GAG GGC      307

GAC ATC GCG CTG CAG ATC CAT TTT ACG CTG ATC CAG GCT TTC TGC TGC      355

GAG AAC GAC ATC GAC ATA GTG CGC GTG GGC GAT GTG CAG CGG CTG GCG      403

GCT ATC GTG GGC GCC GGC GAG GAG GCG GGT GCG CCG GGC GAC CTG CAC      451

TGC ATC CTC ATT TCG AAC CCC AAC GAG GAC GCC TGG AAG GAT CCC GCC      499

TTG GAG AAG CTC AGC CTG TTT TGC GAG GAG AGC CGC AGC GTT AAC GAC      547

TGG GTG CCC AGC ATC ACC CTC CCC GAG T GACAGCCCGG CGGGGACCTT          595

GGTCTGATCG ACGTGGTGAC GCCCCGGGGC GCCTAGAGCG CGGCTGGCTC TGTGGAGGGG     655

CCCTCCGAGG GTGCCCGAGT GCGGCGTGGA GACTGGCAGG CGGGGGGGGC GCCTGGAGAG     715

CGAGGAGGCG CGGCCTCCCG AGGAGGGGCC CGGTGGCGGC AGGGCCAGGC TGGTCCGAGC     775

TGAGGACTCT GCAAGTGTCT GGAGCGGCTG CTCGCCCAGG AAGGCCTAGG CTAGGACGTT     835

GGCCTCAGGG CCAGGAAGGA CAGACTGGCC GGGCAGGCGT GACTCAGCAG CCTGCGCTCG     895

GCAGGAAGGA GCGGCGCCCT GGACTTGGTA CAGTTTCAGG AGCGTGAAGG ACTTAACCGA     955

CTGCCGCTGC TTTTTCAAAA CGGATCCGGG CAATGCTTCG TTTTCTAAAG GATGCTGCTG    1015
```

```
TTGAGCTTTG AATTTTACAA TAAACTTTTT GAAACAAAAA AAAAAAAAAA              1065

(2) INFORMATION FOR SEQ ID NO:12:

(i) SEQUENCE CHARACTERISTICS:
        (A) LENGTH: 159 amino acids
        (B) TYPE: amino acid
        (D) TOPOLOGY: linear (ii) MOLECULE TYPE: protein (xi) SEQUENCE DESCRIPTION: SEQ ID NO:12:

Met Thr Leu Glu Glu Val Arg Gly Gln Asp Thr Val Pro Glu Ser Thr
  1               5                  10                  15

Ala Arg Met Gln Gly Ala Gly Lys Ala Leu His Glu Leu Leu Leu Ser
             20                  25                  30

Ala Gln Arg Gln Gly Cys Leu Thr Ala Gly Val Tyr Glu Ser Ala Lys
         35                  40                  45

Val Leu Asn Val Asp Pro Asp Asn Val Thr Phe Cys Val Leu Ala Ala
     50                  55                  60

Gly Glu Glu Asp Glu Gly Asp Ile Ala Leu Gln Ile His Phe Thr Leu
 65                  70                  75                  80

Ile Gln Ala Phe Cys Cys Glu Asn Asp Ile Asp Ile Val Arg Val Gly
             85                  90                  95

Asp Val Gln Arg Leu Ala Ala Ile Val Gly Ala Gly Glu Glu Ala Gly
            100                 105                 110

Ala Pro Gly Asp Leu His Cys Ile Leu Ile Ser Asn Pro Asn Glu Asp
            115                 120                 125

Ala Trp Lys Asp Pro Ala Leu Glu Lys Leu Ser Leu Phe Cys Glu Glu
        130                 135                 140

Ser Arg Ser Val Asn Asp Trp Val Pro Ser Ile Thr Leu Pro Glu
145                 150                 155

(2) INFORMATION FOR SEQ ID NO:13:

(i) SEQUENCE CHARACTERISTICS:
        (A) LENGTH: 2980 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 240..1475

(xi) SEQUENCE DESCRIPTION: SEQ ID NO:13:

CACACCGCCA GTCTGTGCGC TGAGTCGGAG CCAGAGGCCG CGGGGACACC GGGCCATGCA      60

CGCCCCCAAC TGAAGCTGCA TCTCAAAGCC GAAGATTCCA GCAGCCCAGG GGATTTCAAA     120

GAGCTCAGAC TCAGAGGAAC ATCTGCGGAG AGACCCCCGA AGCCCTCTCC AGGGCAGTCC     180

TCATCCAGAC GCTCCGTTAG TGCAGACAGG AGCGCGCAGT GGCCCCGGCT CGCCGCGCC      239

ATG GAG CGG ATC CCC AGC GCG CAA CCA CCC CCC GCC TGC CTG CCC AAA      287

GCA CCG GGA CTG GAG CAC CGA GAC CTA CCA GGG ATG TAC CCT GCC CAC      335

ATG TAC CAA GTG TAC AAG TCA AGA CGG GGA ATA AAG CGG AGC GAG GAC      383

AGC AAG GAG ACC TAC AAA TTG CCG CAC CGG CTC TTC GAG AAA AAG AGA      431

CGT GAC CGG ATT AAC GAG TGC ATC GCC CAG CTG AAG GAT CTC CTA CCC      479

GAA CAT CTC AAA CTT ACA ACT TTG GGT CAC TTG GAA AAA GCA GTG GTT      527
```

| | |
|---|---|
| CTT GAA CTT ACC TTG AAG CAT GTG AAA GCA CTA ACA AAC CTA ATT GAT | 575 |
| CAG CAG CAG CAG AAA ATC ATT GCC CTG CAG AGT GGT TTA CAA GCT GGT | 623 |
| GAG CTG TCA GGG AGA AAT GTC GAA ACA GGT CAA GAG ATG TTC TGC TCA | 671 |
| GGT TTC CAG ACA TGT GCC CGG GAG GTG CTT CAG TAT CTG GCC AAG CAC | 719 |
| GAG AAC ACT CGG GAC CTG AAG TCT TCG CAG CTT GTC ACC CAC CTC CAC | 767 |
| CGG GTG GTC TCG GAG CTG CTG CAG GGT GGT ACC TCC AGG AAG CCA TCA | 815 |
| GAC CCA GCT CCC AAA GTG ATG GAC TTC AAG GAA AAA CCC AGC TCT CCG | 863 |
| GCC AAA GGT TCG AAA GGT CCT GGG AAA AAC TGC GTG CCA GTC ATC CAG | 911 |
| CGG ACT TTC GCT CAC TCG AGT GGG GAG CAG AGC GGC AGC GAC ACG GAC | 959 |
| ACA GAC AGT GGC TAT GGA GGA GAT TCG GAG AAG GGC GAC TTG CGC AGT | 1007 |
| GAG CAG CCG TGC TTC AAA AGT GAC CAC GGA CGC AGG TTC ACG ATG GGA | 1055 |
| GAA AGG ATC GGC GCA ATT AAG CAA GAG TCC GAA GAA CCC CCC ACA AAA | 1103 |
| AAG AAC CGG ATG CAG CTT TCG GAT GAT GAA GGC CAT TTC ACT AGC AGT | 1151 |
| GAC CTG ATC AGC TCC CCG TTC CTG GGC CCA CAC CCA CAC CAG CCT CCT | 1199 |
| TTC TGC CTG CCC TTC TAC CTG ATC CCA CCT TCA GCG ACT GCC TAC CTG | 1247 |
| CCC ATG CTG GAG AAG TGC TGG TAT CCC ACC TCA GTG CCA GTG CTA TAC | 1295 |
| CCA GGC CTC AAC GCC TCT GCC GCA GCC CTC TCT AGC TTC ATG AAC CCA | 1343 |
| GAC AAG ATC TCG GCT CCC TTG CTC ATG CCC AGA GAC TCC CCT TCT CCC | 1391 |
| TTG CCA GCT CAT CCG TCC GTC GAC TCT TCT GTC TTG CTC CAA GCT CTG | 1439 |
| AAG CCA ATC CCC CCT TTA AAC TTA GAA ACC AAA GAC T AAACTCTCTA | 1486 |
| GGGGATCCTG CTGCTTNGCT TTCCTNCCTC GCTACTTCCT AAAAAGCAAC CNNAAAGNTT | 1546 |
| TNGTGAATGC TGNNAGANTG TTGCATTGTG TATACTGAGA TAATCTGAGG CATGGAGAGC | 1606 |
| AGANNCAGGG TGTGTGTGTG TGTGTGTGTG TGTGTGTGTG TATGTGCGTG TGCGTGCACA | 1666 |
| TGTGTGCCTG CGTGTTGGTA TAGGACTTTA NNGCTCCTTNN GGCATAGGG AAGTCACGAA | 1726 |
| GGATTGCTNG ACATCAGGAG ACTNGGGGGG GATTGTAGCA GACGTCTGGG CTTNNCCCCA | 1786 |
| CCCAGAGAAT AGCCCCCNNC NANACANATC AGCTGGATTT ACAAAAGCTT CAAAGTCTTG | 1846 |
| GTCTGTGAGT CACTCTTCAG TTTGGGAGCT GGGTCTGTGG CTTTGATCAG AAGGTACTTT | 1906 |
| CAAAAGAGGG CTTTCCAGGG CTCAGCTCCC AACCAGCTGT TAGGACCCCA CCCTTTTGCC | 1966 |
| TTTATTGTCG ACGTGACTCA CCAGACGTCG GGGAGAGAGA GCAGTCAGAC CGAGCTTTTC | 2026 |
| TGCTAACATG GGGAGGGTAG CAGACACTGG CATAGCACGG TAGTGGTTTG GGGGAGGGTT | 2086 |
| TCCGCAGGTC TGCTCCCCAC CCCTGCCTCG GAAGAATAAA GAGAATGTAG TTCCCTACTC | 2146 |
| AGGCTTTCGT AGTGATTAGC TTACTAAGGA ACTGAAAATG GGCCCCTTGT ACAAGCTGAG | 2206 |
| CTGCCCCGGA GGGAGGGAGG AGTTCCCTGG GCTTCTGGCA CCTGTTTCTA GGCCTAACCA | 2266 |
| TTAGTACTTA CTGTGCAGGG AACCAAACCA AGGTCTGAGA AATGCGGACA NCCCGAGCGA | 2326 |
| GCACCCCAAA GTGCACAAAG CTGAGTAAAA AGCTGCCCCC TTCAAACAGA ACTAGACTCA | 2386 |
| GTTTTCAATT CCATCCTAAA ACTCCTTTTA ACCAAGCTTA GCTTCTCAAA GGGCTAACCA | 2446 |
| AGCCTTGGAA CCGCCAGATC CTTTCTGTAG GCTAATTCCT CTTGGCCAAC GGCATATGGA | 2506 |
| GTGTCCTTAT TGCTAAAAAG GATTCCGNCT CCTTCAAAGA AGTTTTATTT TTGGTCCAGA | 2566 |
| GTACTTGTTT TCCCGATGTG TCCAGCCAGC TCCGCAGCAG CTTTTCAAAA TGCACTATGC | 2626 |
| CTGATTGCTG ATCGTGTTTT AACTTTTTCT TTTCCTGTTT TTATTTTGGT ATTAAGTCGC | 2686 |

-continued

```
TGGCTTTATT TGTAAAGCTG TTATAAATAT ATATTATATN AANTATATTA AAAAGGAAAN    2746

TGTTNCAGAT GTTTATTTGT ATAATTACTT GATTCACANA GNGAGAAAAA NTGANTGTAT    2806

TCCTGTNTTN GAAGAGAAGA NNAATTTTTT TTTTCTCTAG GGAGAGGTAC AGNGTTNNTN    2866

TTTTGGGGCC TNCCNGAAGG GGTAAANNNG AAAATNTTTC TATNTATGAG TAAATGTTAA    2926

GTAGTTGTNT NAAAATACTN AATAAAATAA TTCTCTCCCT GTGGNNGAGA NAAC          2980
```

(2) INFORMATION FOR SEQ ID NO:14:

(i) SEQUENCE CHARACTERISTICS:
        (A) LENGTH: 412 amino acids
        (B) TYPE: amino acid
        (D) TOPOLOGY: linear (ii) MOLECULE TYPE: protein (xi) SEQUENCE DESCRIPTION: SEQ ID NO:14:

```
Met Glu Arg Ile Pro Ser Ala Gln Pro Pro Ala Cys Leu Pro Lys
 1               5                  10                  15

Ala Pro Gly Leu Glu His Arg Asp Leu Pro Gly Met Tyr Pro Ala His
                20                  25                  30

Met Tyr Gln Val Tyr Lys Ser Arg Arg Gly Ile Lys Arg Ser Glu Asp
        35                  40                  45

Ser Lys Glu Thr Tyr Lys Leu Pro His Arg Leu Phe Glu Lys Lys Arg
    50                  55                  60

Arg Asp Arg Ile Asn Glu Cys Ile Ala Gln Leu Lys Asp Leu Leu Pro
65                  70                  75                  80

Glu His Leu Lys Leu Thr Thr Leu Gly His Leu Glu Lys Ala Val Val
                85                  90                  95

Leu Glu Leu Thr Leu Lys His Val Lys Ala Leu Thr Asn Leu Ile Asp
                100                 105                 110

Gln Gln Gln Gln Lys Ile Ile Ala Leu Gln Ser Gly Leu Gln Ala Gly
            115                 120                 125

Glu Leu Ser Gly Arg Asn Val Glu Thr Gly Gln Glu Met Phe Cys Ser
        130                 135                 140

Gly Phe Gln Thr Cys Ala Arg Glu Val Leu Gln Tyr Leu Ala Lys His
145                 150                 155                 160

Glu Asn Thr Arg Asp Leu Lys Ser Ser Gln Leu Val Thr His Leu His
                165                 170                 175

Arg Val Val Ser Glu Leu Leu Gln Gly Gly Thr Ser Arg Lys Pro Ser
                180                 185                 190

Asp Pro Ala Pro Lys Val Met Asp Phe Lys Glu Lys Pro Ser Ser Pro
            195                 200                 205

Ala Lys Gly Ser Glu Gly Pro Gly Lys Asn Cys Val Pro Val Ile Gln
        210                 215                 220

Arg Thr Phe Ala His Ser Ser Gly Glu Gln Ser Gly Ser Asp Thr Asp
225                 230                 235                 240

Thr Asp Ser Gly Tyr Gly Gly Asp Ser Glu Lys Gly Asp Leu Arg Ser
                245                 250                 255

Glu Gln Pro Cys Phe Lys Ser Asp His Gly Arg Arg Phe Thr Met Gly
                260                 265                 270

Glu Arg Ile Gly Ala Ile Lys Gln Glu Ser Glu Glu Pro Pro Thr Lys
            275                 280                 285

Lys Asn Arg Met Gln Leu Ser Asp Asp Glu Gly His Phe Thr Ser Ser
        290                 295                 300
```

```
Asp Leu Ile Ser Ser Pro Phe Leu Gly Pro His Pro His Gln Pro Pro
305                 310                 315                 320

Phe Cys Leu Pro Phe Tyr Leu Ile Pro Pro Ser Ala Thr Ala Tyr Leu
                325                 330                 335

Pro Met Leu Glu Lys Cys Trp Tyr Pro Thr Ser Val Pro Val Leu Tyr
                340                 345                 350

Pro Gly Leu Asn Ala Ser Ala Ala Ala Leu Ser Ser Phe Met Asn Pro
                355                 360                 365

Asp Lys Ile Ser Ala Pro Leu Leu Met Pro Gln Arg Leu Pro Ser Pro
370                 375                 380

Leu Pro Ala His Pro Ser Val Asp Ser Ser Val Leu Leu Gln Ala Leu
385                 390                 395                 400

Lys Pro Ile Pro Pro Leu Asn Leu Glu Thr Lys Asp
                405                 410 412
```

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

GGGGTCTACC AGGGATGTAC          20

(2) INFORMATION FOR SEQ ID NO:16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

GTAAACCACT CTGCAGGGCA ATGA      24

(2) INFORMATION FOR SEQ ID NO:17:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

GATCGTAGTC ACGCAGGTGG GATCCCTA  28

(2) INFORMATION FOR SEQ ID NO:18:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

GATCTAGGGA TCCCACCTGC GTGACTAC  28

(2) INFORMATION FOR SEQ ID NO:19:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

GATCGGTGTA GGCCACGTGA CCGGGTGT                            28

(2) INFORMATION FOR SEQ ID NO:20:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

GATCACACCC GGTCACGTGG CCTACACC                            28

(2) INFORMATION FOR SEQ ID NO:21:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

GATCGGCAGC CGGCACGCGA CAGGGCC                              27

(2) INFORMATION FOR SEQ ID NO:22:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

GATCGGCCCT GTCGCGTGCC GGCTGCC                              27

(2) INFORMATION FOR SEQ ID NO:23:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

GATCACGCCA CGAGCCACAA GGATTG                                26

(2) INFORMATION FOR SEQ ID NO:24:

(i) SEQUENCE CHARACTERISTICS:

```
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

GATCCAATCC TTGTGGCTCG TGGCGT                                           26

(2) INFORMATION FOR SEQ ID NO:25:

(i) SEQUENCE CHARACTERISTICS:
        (A) LENGTH: 2297 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

GCGCCGCATC CTGGAGGTTG GGATGCTCTT GTCCAAAATC AACTCGCTTG                 50

CCCACCTGCG CGCCCGCGCC TGCAACGACC TGCACGCCAC CAAGCTGGCG                 100

CCGGGCAAGG AGAAGGAGCC CCTGGAGTCG CAGTACCAGG TGGGCCCGCT                 150

ACTGGGCAGC GGCGGCTTCG GCTCGGTCTA CTCAGGCATC CGCGTCTCCG                 200

ACAACTTGCC GGTGGCCATC AAACACGTGG AGAAGGACCG GATTTCCGAC                 250

TGGGGAGAGC TGCCTAATGG CACTCGAGTG CCCATGGAAG TGGTCCTGCT                 300

GAAGAAGGTG AGCTCGGGTT CTCCGGCGT CATTAGGCTC CTGGACTGGT                  350

TCGAGAGGCC CGACAGTTTC GTCCTGATCC TGGAGAGGCC CGAGCCGGTG                 400

CAAGATCTCT TCGACTTCAT CACGGAAAGG GGAGCCCTGC AAGAGGAGCT                 450

GGCCCGCAGC TTCTTCTGGC AGGTGCTGGA GGCCGTGCGG CACTGCCACA                 500

ACTGCGGGGT GCTCCACCGC GACATCAAGG ACGAAAACAT CCTTATCGAC                 550

CTCAATCGCG GCGAGCTCAA GCTCATCGAC TTCGGGTCGG GGGCGCTGCT                 600

CAAGGACACC GTCTACACGG ACTTCGATGG GACCCGAGTG TATAGCCCTC                 650

CAGAGTGGAT CCGCTACCAT CGCTACCATG GCAGGTCGGC GGCAGTCTGG                 700

TCCCTGGGGA TCCTGCTGTA TGATATGGTG TGTGGAGATA TTCCTTTCGA                 750

GCATGACGAA GAGATCATCA GGGGCCAGGT TTTCTTCAGG CAGAGGGTCT                 800

CTTCAGAATG TCAGCATCTC ATTAGATGGT GCTTGGCCCT GAGACCATCA                 850

GATAGGCCAA CCTTCGAAGA AATCCAGAAC CATCCATGGA TGCAAGATGT                 900

TCTCCTGCCC CAGGAAACTG CTGAGATCCA CCTCCACAGC CTGTCGCCGG                 950

GGCCCAGCAA ATAGCAGCCT TTCTGGCAGG TCCTCCCCTC TCTTGTCAGA                 1000

TGCCCAGGAG GGAAGCTTCT GTCTCCAGCT TTCCCGAGTA CCAGTGACAC                 1050

GTCTCGCCAA GCAGGACAGT GCTTGATACA GGAACAACAT TTACAACTCA                 1100

TTCCAGATCC CAGGCCCCTG GAGGCTGCCT CCCAACAGTG GGGAAGAGTG                 1150

ACTCTCCAGG GGTCCTAGGC CTCAACTCCT CCCATAGATA CTCTCTTCTT                 1200

CTCATAGGTG TCCAGCATTG CTGGACTCTG AAATATCCCG GGGGTGGGGG                 1250

GTGGGGGTGG GTCAGAACCC TGCCATGGAA CTGTTTCCTT CATCATGAGT                 1300

TCTGCTGAAT GCCGCGATGG GTCAGGTAGG GGGGAAACAG GTTGGGATGG                 1350

GATAGGACTA GCACCATTTT AAGTCCCTGT CACCTCTTCC GACTCTTTCT                 1400
```

-continued

```
GAGTGCCTTC TGTGGGGACT CCGGCTGTGC TGGGAGAAAT ACTTGAACTT    1450

GCCTCTTTTA CCTGCTGCTT CTCCAAAAAT CTGCCTGGGT TTTGTTCCCT    1500

ATTTTTCTCT CCTGTCCTCC CTCACCCCCT CCTTCATATG AAAGGTGCCA    1550

TGGAAGAGGC TACAGGGCCA AACGCTGAGC CACCTGCCCT TTTTTCTCCT    1600

CCTTTAGTAA AACTCCGAGT GAACTGGTCT TCCTTTTTGG TTTTTACTTA    1650

ACTGTTTCAA AGCCAAGACC TCACACACAC AAAAAATGCA CAAACAATGC    1700

AATCAACAGA AAAGCTGTAA ATGTGTGTAC AGTTGGCATG GTAGTATACA    1750

AAAAGATTGT AGTGGATCTA ATTTTTAAGA AATTTTGCCT TTAAGTTATT    1800

TTACCTGTTT TTGTTTCTTG TTTTGAAAGA TGCGCATTCT AACCTGGAGG    1850

TCAATGTTAT GTATTTATTT ATTTATTTAT TTGGTTCCCT TCCTANNNNN    1900

NNNNNNGCTG CTGCCCTAGT TTTCTTTCCT CCTTTCCTCC TCTGACTTGG    1950

GGACCTTTTG GGGGAGGGCT GCGACGCTTG CTCTGTTTGT GGGGTGACGG    2000

GACTCAGGCG GGACAGTGCT GCAGCTCCCT GGCTTCTGTG GGGCCCCTCA    2050

CCTACTTACC CAGGTGGGTC CCGGCTCTGT GGGTGATGGG GAGGGGCATT    2100

GCTGACTGTG TATATAGGAT AATTATGAAA AGCAGTTCTG GATGGTGTGC    2150

CTTCCAGATC CTCTCTGGGG CTGTGTTTTG AGCAGCAGGT AGCCTGCTGG    2200

TTTTATCTGA GTGAAATACT GTACAGGGGA ATAAAAGAGA TCTTATTTTT    2250

TTTTTTATAC TTGGCGTTTT TTGAATAAAA ACCTTTTGTC TTAAAAC      2297
```

(2) INFORMATION FOR SEQ ID NO:26:

(i) SEQUENCE CHARACTERISTICS:
        (A) LENGTH: 313 amino acids
        (B) TYPE:AMINO
        (B) TYPE:AMINO
        (C) STRANDEDNESS: Not Relevant
        (D) TOPOLOGY: Not Relevant (ii) MOLECULE TYPE: peptide (xi) SEQUENCE DESCRIPTION: SEQ ID NO:26:

```
        Met Leu Leu Ser Lys Ile Asn Ser Leu Ala
          1               5                  10

His Leu Arg Ala Arg Ala Cys Asn Asp Leu His Ala Thr Lys Leu Ala
             15                  20                  25

Pro Gly Lys Glu Lys Glu Pro Leu Glu Ser Gln Tyr Gln Val Gly Pro
         30                  35                  40

Leu Leu Gly Ser Gly Gly Phe Gly Ser Val Tyr Ser Gly Ile Arg Val
             45                  50                  55

Ser Asp Asn Leu Pro Val Ala Ile Lys His Val Glu Lys Asp Arg Ile
         60                  65                  70

Ser Asp Trp Gly Glu Leu Pro Asn Gly Thr Arg Val Pro Met Glu Val
75                  80                  85                  90

Val Leu Leu Lys Lys Val Ser Ser Gly Phe Ser Gly Val Ile Arg Leu
             95                 100                 105

Leu Asp Trp Phe Glu Arg Pro Asp Ser Phe Val Leu Ile Leu Glu Arg
         110                 115                 120

Pro Glu Pro Val Gln Asp Leu Phe Asp Phe Ile Thr Glu Arg Gly Ala
         125                 130                 135

Leu Gln Glu Glu Leu Ala Arg Ser Phe Phe Trp Gln Val Leu Glu Ala
         140                 145                 150
```

| | | | | | | | | | | | |
|---|---|---|---|---|---|---|---|---|---|---|---|
|Val|Arg|His|Cys|His|Asn|Cys|Gly|Val|Leu|His|Arg|Asp|Ile|Lys|Asp|
|155| | | |160| | | | |165| | | | |170| |

Glu Asn Ile Leu Ile Asp Leu Asn Arg Gly Glu Leu Lys Leu Ile Asp
            175             180             185

Phe Gly Ser Gly Ala Leu Leu Lys Asp Thr Val Tyr Thr Asp Phe Asp
190     195             200

Gly Thr Arg Val Tyr Ser Pro Pro Glu Trp Ile Arg Tyr His Arg Tyr
        205             210             215

His Gly Arg Ser Ala Ala Val Trp Ser Leu Gly Ile Leu Leu Tyr Asp
        220             225             230

Met Val Cys Gly Asp Ile Pro Phe Glu His Asp Glu Glu Ile Ile Arg
235             240             245             250

Gly Gln Val Phe Phe Arg Gln Arg Val Ser Ser Glu Cys Gln His Leu
                255             260             265

Ile Arg Trp Cys Leu Ala Leu Arg Pro Ser Asp Arg Pro Thr Phe Glu
            270             275             280

Glu Ile Gln Asn His Pro Trp Met Gln Asp Val Leu Leu Pro Gln Glu
            285             290             295

Thr Ala Glu Ile His Leu His Ser Leu Ser Pro Gly Pro Ser Lys
300             305             310     313

(2) INFORMATION FOR SEQ ID NO:27:

(i) SEQUENCE CHARACTERISTICS:
        (A) LENGTH: 606 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

```
ATG                                                               3

TGC CGC ACC CTG GCC GCC TTC CCC ACC ACC TGC CTG GAG AGA GCC AAA  51

GAG TTC AAG ACA CGT CTG GGG ATC TTT CTT CAC AAA TCA GAG CTG GGC  99

TGC GAT ACT GGG AGT ACT GGC AAG TTC GAG TGG GGC AGT AAA CAC AGC 147

AAA GAG AAT AGA AAC TTC TCA GAA GAT GTG CTG GGG TGG AGA GAG TCG 195

TTC GAC CTG CTG CTG AGC AGT AAA AAT GGA GTG GCT GCC TTC CAC GCT 243

TTC CTG AAG ACA GAG TTC AGT GAG GAG AAC CTG GAG TTC TGG CTG GCC 291

TGT GAG GAG TTC AAG AAG ATC CGA TCA GCT ACC AAG CTG GCC TCC AGG 339

GCA CAC CAG ATC TTT GAG GAG TTC ATT TGC AGT GAG GCC CCT AAA GAG 387

GTC AAC ATT GAC CAT GAG ACC CGC GAG CTG ACG AGG ATG AAC CTG CAG 435

ACT GCC ACA GCC ACA TGC TTT GAT GCG GCT CAG GGG AAG ACA CGT ACC 483

CTG ATG GAG AAG GAC TCC TAC CCA CGC TTC CTG AAG TCG CCT GCT TAC 531

CGG GAC CTG GCT GCC CAA GCC TCA GCC GCC TCT GCC ACT CTG TCC AGC 579

TGC AGC CTG GAC CAG CCC TCA CAC ACC                             606
```

(2) INFORMATION FOR SEQ ID NO:28:

(i) SEQUENCE CHARACTERISTICS:
        (A) LENGTH: 180 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 28:

| | |
|---|---|
| ATG GGG | 6 |
| ACG TTA AGC ATG CAG CAA CTA CAG TCA TTT GTT CTC AGA GGT CTG GAC | 54 |
| CAA AGA GAA ACA AGA AAA GCT GGA GTC ACA CTA CCA AAG GCC GAA GCT | 102 |
| GAG CAA CAG AGC TCT GGA GTC AGC TGC CTG GGT TCA GCA TGC AGC GCT | 150 |
| GCC GTG GAC GAT CTG TCT CTC TTG CAT ATA | 180 |

(2) INFORMATION FOR SEQ ID NO: 29:

(i) SEQUENCE CHARACTERISTICS:
        (A) LENGTH: 1074 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

| | |
|---|---|
| ATG GGA AAT | 9 |
| GCC TCC AAT GAC TCC CAG TCT GAG GAC TGC GAG ACG CGA CAG TGG TTT | 57 |
| CCC CCA GGC GAA AGC CCA GCC ATC AGT TCC GTC ATG TTC TCG GCC GGG | 105 |
| GTG CTG GGG AAC CTC ATA GAA CTG GCG CTG CTG GCG CGC CGC TGG CAG | 153 |
| GGG GAC GTG GGG TGC AGC GCC GGC CGT AGG AGC TCC CTC TCC TTG TTC | 201 |
| CAC GTG CTG GTG ACC GAG CTG GTG TTC ACC GAC CTG CTC GGG ACC TGC | 249 |
| CTC ATC AGC CCA GTG GTA CTG GCT TCG TAC GCG CGG AAC CAG ACC CTG | 297 |
| GTG GCA CTG GCG CCC GAG AGC CGC GCG TCC ACC TAC TTC GCT TTC GCC | 345 |
| ATG ACC TTC TTC AGC CTG GCC ACG ATG CTC ATG CTC TTC ACC ATG GCC | 393 |
| CTG GAG CGC TAC CTC TCG ATC GGG CAC CCC TAC TTC TAC CAG CGC CGC | 441 |
| GTC TCG CGC TCC GGG GGC CTG GCC GTG CTG CCT GTC ATC TAT GCA GTC | 489 |
| TCC CTG CTC TTC TGC TCA CTG CCG CTG CTG GAC TAT GGG CAG TAC GTC | 537 |
| CAG TAC TGC CCC GGG ACC TGG TGC TTC ATC CGG CAC GGG CGG ACC GCT | 585 |
| TAC CTG CAG CTG TAC GCC ACC CTG CTG CTG CTT CTC ATT GTC TCG GTG | 633 |
| CTC GCC TGC AAC TTC AGT GTC ATT CTC AAC CTC ATC CGC ATG CAC CGC | 681 |
| CGA AGC CGG AGA AGC CGC TGC GGA CCT TCC CTG GGC AGT GGC CGG GGC | 729 |
| GGC CCC GGG GCC GCC AGG AGA GGG GAA AGG GTG TCC ATG GCG GAG GAG | 777 |
| ACG GAC CAC CTC ATT CTC CTG GCT ATC ATG ACC ATC ACC TTC GCC GTC | 825 |
| TGC TCC TTG CCT TTC ACG ATT TTT GCA TAT ATG AAT GAA ACC TCT TCC | 873 |
| CGA AAG GAA AAA TGG GAC CTC CAA GCT CTT AGG TTT TTA TCA ATT AAT | 921 |
| TCA ATA ATT GAC CCT TGG GTC TTT GCC ATC CTT AGG CCT CCT GTT CTG | 969 |
| AGA CTA ATG CGT TCA GTC CTC TGT TGT CGG ATT TCA TTA AGA ACA CAA | 1017 |
| GAT GCA ACA CAA ACT TCC TGT TCT ACA CAG TCA GAT GCC AGT AAA CAG | 1065 |
| GCT GAC CTT | 1074 |

(2) INFORMATION FOR SEQ ID NO: 30:

(i) SEQUENCE CHARACTERISTICS:
        (A) LENGTH: 2289 base pairs (B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:30:

| | |
|---|---:|
| ATG GAT CAT TTG AAC GAG | 18 |
| GCA ACT CAG GGG AAA GAA CAT TCA GAA ATG TCT AAC AAT GTG AGT GAT | 66 |
| CCG AAG GGT CCA CCA GCC AAG ATT GCC CGC CTG GAG CAG AAC GGG AGC | 114 |
| CCG CTA GGA AGA GGA AGG CTT GGG AGT ACA GGT GCA AAA ATG CAG GGA | 162 |
| GTG CCT TTA AAA CAC TCG GGC CAT CTG ATG AAA ACC AAC CTT AGG AAA | 210 |
| GGA ACC ATG CTG CCA GTT TTC TGT GTG GTG GAA CAT TAT GAA AAC GCC | 258 |
| ATT GAA TAT GAT TGC AAG GAG GAG CAT GCA GAA TTT GTG CTG GTG AGA | 306 |
| AAG GAT ATG CTT TTC AAC CAG CTG ATC GAA ATG GCA TTG CTG TCT CTA | 354 |
| GGT TAT TCA CAT AGC TCT GCT GCC CAG GCC AAA GGG CTA ATC CAG GTT | 402 |
| GGA AAG TGG AAT CCA GTT CCA CTG TCT TAC GTG ACA GAT GCC CCT GAT | 450 |
| GCT ACA GTA GCA GAT ATG CTT CAA GAT GTG TAT CAT GTG GTC ACA TTG | 498 |
| AAA ATT CAG TTA CAC AGT TGC CCC AAA CTA GAA GAC TTG CCT CCC GAA | 546 |
| CAA TGG TCG CAC ACC ACA GTG AGG AAT GCT CTG AAG GAC TTA CTG AAA | 594 |
| GAT ATG AAT CAG AGT TCA TTG GCC AAG GAG TGC CCC CTT TCA CAG AGT | 642 |
| ATG ATT TCT TCC ATT GTG AAC AGT ACT TAC TAT GCA AAT GTC TCA GCA | 690 |
| GCA AAA TGT CAA GAA TTT GGA AGG TGG TAC AAA CAT TTC AAG AAG ACA | 738 |
| AAA GAT ATG ATG GTT GAA ATG GAT AGT CTT TCT GAG CTA TCC CAG CAA | 786 |
| GGC GCC AAT CAT GTC AAT TTT GGC CAG CAA CCA GTT CCA GGG AAC ACA | 834 |
| GCC GAG CAG CCT CCA TCC CCT GCG CAG CTC TCC CAT GGC AGC CAG CCC | 882 |
| TCT GTC CGG ACA CCT CTT CCA AAC CTG CAC CCT GGG CTC GTA TCA ACA | 930 |
| CCT ATC AGT CCT CAA TTG GTC AAC CAG CAG CTG GTG ATG GCT CAG CTG | 978 |
| CTG AAC CAG CAG TAT GCA GTG AAT AGA CTT TTA GCC CAG CAG TCC TTA | 1026 |
| AAC CAA CAA TAC TTG AAC CAC CCT CCC CCT GTC AGT AGA TCT ATG AAT | 1074 |
| AAG CCT TTG GAG CAA CAG GTT TCG ACC AAC ACA GAG GTG TCT TCC GAA | 1122 |
| ATC TAC CAG TGG GTA CGC GAT GAA CTG AAA CGA GCA GGA ATC TCC CAG | 1170 |
| GCG GTA TTT GCA CGT GTG GCT TTT AAC AGA ACT CAG GGC TTG CTT TCA | 1218 |
| GAA ATC CTC CGA AAG GAA GAG GAC CCC AAG ACT GCA TCC CAG TCT TTG | 1266 |
| CTG GTA AAC CTT CGG GCT ATG CAG AAT TTC TTG CAG TTA CCG GAA GCT | 1314 |
| GAA AGA GAC CGA ATA TAC CAG GAC GAA AGG GAA AGG AGC TTG AAT GCT | 1362 |
| GCC TCG GCC ATG GGT CCT GCC CCC CTC ATC AGC ACA CCA CCC AGC CGT | 1410 |
| CCT CCC CAG GTG AAA ACA GCT ACT ATT GCC ACT GAA AGG AAT GGG AAA | 1458 |
| CCA GAG AAC AAT ACC ATG AAC ATT AAT GCT TCC ATT TAT GAT GAG ATT | 1506 |
| CAG CAG GAA ATG AAG CGT GCT AAA GTG TCT CAA GCA CTG TTT GCA AAG | 1554 |
| GTT GCA GCA ACC AAA AGC CAG GGA TGG TTG TGC GAG CTG TTA CGC TGG | 1602 |
| AAA GAA GAT CCT TCT CCA GAA AAC AGA ACC CTG TGG GAG AAC CTC TCC | 1650 |
| ATG ATC CGA AGG TTC CTC AGT CTT CCT CAG CCA GAA CGT GAT GCC ATT | 1698 |

```
TAT GAA CAG GAG AGC AAC GCG GTG CAT CAC CAT GGC GAC AGG CCG CCC          1746

CAC ATT ATC CAT GTT CCA GCA GAG CAG ATT CAG CAA CAG CAG CAG CAA          1794

CAG CAA CAG CAG CAG CAG CAG CAG CAG GCA CCG CCG CCT CCA CAG CCA          1842

CAG CAG CAG CCA CAG ACA GGC CCT CGG CTC CCC CCA CGG CAA CCC ACG          1890

GTG GCC TCT CCA GCA GAG TCA GAT GAG GAA AAC CGA CAG AAG ACC CGG          1938

CCA CGA ACA AAA ATT TCA GTG GAA GCC TTG GGA ATC CTC CAG AGT TTC          1986

ATA CAA GAC GTG GGC CTG TAC CCT GAC GAA GAG GCC ATC CAG ACT CTG          2034

TCT GCC CAG CTC GAC CTT CCC AAG TAC ACC ATC ATC AAG TTC TTT CAG          2082

AAC CAG CGG TAC TAT CTC AAG CAC CAC GGC AAA CTG AAG GAC AAT TCC          2130

GGT TTA GAG GTC GAT GTG GCA GAA TAT AAA GAA GAG GAG CTG CTG AAG          2178

GAT TTG GAA GAG AGT GTC CAA GAT AAA AAT ACT AAC ACC CTT TTT TCA          2226

GTG AAA CTA GAA GAA GAG CTG TCA GTG GAA GGA AAC ACA GAC ATT AAT          2274

ACT GAT TTG AAA GAC                                                      2289

(2) INFORMATION FOR SEQ ID NO: 31:

(i) SEQUENCE CHARACTERISTICS:
        (A) LENGTH: 477 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 31:

ATG ACT CTG GAA GAA GTC                    18

CGC GGC CAG GAC ACA GTT CCG GAA AGC ACA GCC AGG ATG CAG GGT GCC           66

GGG AAA GCG CTG CAT GAG TTG CTG CTG TCG GCG CAG CGT CAG GGC TGC           114

CTC ACT GCC GGC GTC TAC GAG TCA GCC AAA GTC TTG AAC GTG GAC CCC           162

GAC AAT GTG ACC TTC TGT GTG CTG GCT GCG GGT GAG GAG GAC GAG GGC           210

GAC ATC GCG CTG CAG ATC CAT TTT ACG CTG ATC CAG GCT TTC TGC TGC           258

GAG AAC GAC ATC GAC ATA GTG CGC GTG GGC GAT GTG CAG CGG CTG GCG           306

GCT ATC GTG GGC GCC GGC GAG GAG GCG GGT GCG CCG GGC GAC CTG CAC           354

TGC ATC CTC ATT TCG AAC CCC AAC GAG GAC GCC TGG AAG GAT CCC GCC           402

TTG GAG AAG CTC AGC CTG TTT TGC GAG GAG AGC CGC AGC GTT AAC GAC           450

TGG GTG CCC AGC ATC ACC CTC CCC GAG                                       477

(2) INFORMATION FOR SEQ ID NO: 32:

(i) SEQUENCE CHARACTERISTICS:
        (A) LENGTH: 1236 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 32:

ATG GAG CGG ATC CCC AGC GCG CAA CCA CCC CCC GCC TGC CTG CCC AAA           48

GCA CCG GGA CTG GAG CAC CGA GAC CTA CCA GGG ATG TAC CCT GCC CAC           96

ATG TAC CAA GTG TAC AAG TCA AGA CGG GGA ATA AAG CGG AGC GAG GAC          144
```

```
AGC AAG GAG ACC TAC AAA TTG CCG CAC CGG CTC TTC GAG AAA AAG AGA        192

CGT GAC CGG ATT AAC GAG TGC ATC GCC CAG CTG AAG GAT CTC CTA CCC        240

GAA CAT CTC AAA CTT ACA ACT TTG GGT CAC TTG GAA AAA GCA GTG GTT        288

CTT GAA CTT ACC TTG AAG CAT GTG AAA GCA CTA ACA AAC CTA ATT GAT        336

CAG CAG CAG CAG AAA ATC ATT GCC CTG CAG AGT GGT TTA CAA GCT GGT        384

GAG CTG TCA GGG AGA AAT GTC GAA ACA GGT CAA GAG ATG TTC TGC TCA        432

GGT TTC CAG ACA TGT GCC CGG GAG GTG CTT CAG TAT CTG GCC AAG CAC        480

GAG AAC ACT CGG GAC CTG AAG TCT TCG CAG CTT GTC ACC CAC CTC CAC        528

CGG GTG GTC TCG GAG CTG CTG CAG GGT GGT ACC TCC AGG AAG CCA TCA        576

GAC CCA GCT CCC AAA GTG ATG GAC TTC AAG GAA AAA CCC AGC TCT CCG        624

GCC AAA GGT TCG GAA GGT CCT GGG AAA AAC TGC GTG CCA GTC ATC CAG        672

CGG ACT TTC GCT CAC TCG AGT GGG GAG CAG AGC GGC AGC GAC ACG GAC        720

ACA GAC AGT GGC TAT GGA GGA GAT TCG GAG AAG GGC GAC TTG CGC AGT        768

GAG CAG CCG TGC TTC AAA AGT GAC CAC GGA CGC AGG TTC ACG ATG GGA        816

GAA AGG ATC GGC GCA ATT AAG CAA GAG TCC GAA GAA CCC CCC ACA AAA        864

AAG AAC CGG ATG CAG CTT TCG GAT GAT GAA GGC CAT TTC ACT AGC AGT        912

GAC CTG ATC AGC TCC CCG TTC CTG GGC CCA CAC CCA CAC CAG CCT CCT        960

TTC TGC CTG CCC TTC TAC CTG ATC CCA CCT TCA GCG ACT GCC TAC CTG       1008

CCC ATG CTG GAG AAG TGC TGG TAT CCC ACC TCA GTG CCA GTG CTA TAC       1056

CCA GGC CTC AAC GCC TCT GCC GCA GCC CTC TCT AGC TTC ATG AAC CCA       1104

GAC AAG ATC TCG GCT CCC TTG CTC ATG CCC AGA GAC TCC CCT TCT CCC       1152

TTG CCA GCT CAT CCG TCC GTC GAC TCT TCT GTC TTG CTC CAA GCT CTG       1200

AAG CCA ATC CCC CCT TTA AAC TTA GAA ACC AAA GAC                       1236

(2) INFORMATION FOR SEQ ID NO: 33:

(i) SEQUENCE CHARACTERISTICS:
        (A) LENGTH: 774 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 33:

ATG GTC                                                                  6

CTC TGC GTT CAG GGA CCT CGT CCT TTG CTG GCT GTG GAG CGG ACT GGG         54

CAG CGG CCC CTG TGG GCC CCG TCC CTG GAA CTG CCC AAG CCA GTC ATG        102

CAG CCC TTG CCT GCT GGG GCC TTC CTC GAG GAG GTG GCA GAG GGT ACC        150

CCA GCC CAG ACA GAG AGT GAG CCA AAG GTG CTG GAC CCA GAG GAG GAT        198

CTG CTG TGC ATA GCC AAG ACC TTC TCC TAC CTT CGG GAA TCT GGC TGG        246

TAT TGG GGT TCC ATT ACG GCC AGC GAG GCC CGA CAA CAC CTG CAG AAG        294

ATG CCA GAA GGC ACG TTC TTA GTA CGT GAC AGC ACG CAC CCC AGC TAC        342

CTG TTC ACG CTG TCA GTG AAA ACC ACT CGT GGC CCC ACC AAT GTA CGC        390

ATT GAG TAT GCC GAC TCC AGC TTC CGT CTG GAC TCC AAC TGC TTG TCC        438
```

| | |
|---|---|
| AGG CCA CGC ATC CTG GCC TTT CCG GAT GTG GTC AGC CTT GTG CAG CAC | 486 |
| TAT GTG GCC TCC TGC ACT GCT GAT ACC CGA AGC GAC AGC CCC GAT CCT | 534 |
| GCT CCC ACC CCG GCC CTG CCT ATG CCT AAG GAG GAT GCG CCT AGT GAC | 582 |
| CCA GCA CTG CCT GCT CCT CCA CCA GCC ACT GCT GTA CAC CTA AAA CTG | 630 |
| GTG CAG CCC TTT GTA CGC AGA AGA AGT GCC CGC AGC CTG CAA CAC CTG | 678 |
| TGC CGC CTT GTC ATC AAC CGT CTG GTG GCC GAC GTG GAC TGC CTG CCA | 726 |
| CTG CCC CGG CGC ATG GCC GAC TAC CTC CGA CAG TAC CCC TTC CAG CTC | 774 |

(2) INFORMATION FOR SEQ ID NO: 34:

(i) SEQUENCE CHARACTERISTICS:
        (A) LENGTH: 2249 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 34:

| | |
|---|---|
| CGCGGCGTAG GACCTCCAAC CC TAC GAG AAC AGG TTT TAG TTG AGC GAA CGG | 52 |
| GTG GAC GCG CGG GCG CGG ACG TTG CTG GAC GTG CGG TGG TTC GAC CGC | 100 |
| GGC CCG TTC CTC TTC CTC GGG GAC CTC AGC GTC ATG GTC CAC CCG GGC | 148 |
| GAT GAC CCG TCG CCG CCG AAG CCG AGC CAG ATG AGT CCG TAG GCG CAG | 196 |
| AGG CTG TTG AAC GGC CAC CGG TAG TTT GTG CAC CTC TTC CTG GCC TAA | 244 |
| AGG CTG ACC CCT CTC GAC GGA TTA CCG TGA GCT CAC GGG TAC CTT CAC | 292 |
| CAG GAC GAC TTC TTC CAC TCG AGC CCA AAG AGG CCG CAG TAA TCC GAG | 340 |
| GGG CTC GGC CAC GTT CTA GAG AAG CTG AAG TAG TGC CTT TCC CCT CGG | 388 |
| GAC GTT CTC CTC GAC CGG GCG TCG AAG AAG ACC GTC CAC GAC CTC CGG | 436 |
| CAC GCC GTG ACG GTG TTG ACG CCC CAC GAG GTG GCG CTG TAG TTC CTG | 484 |
| CTT TTG TAG GAA TAG CTG GAG TTA GCG CCG CTC GAG TTC GAG TAG CTG | 532 |
| AAG CCC AGC CCC CGC GAC GAG TTC CTG TGG CAG ATG TGC CTG AAG CTA | 580 |
| CCC TGG GCT CAC ATA TCG GGA GGT CTC ACC TAG GCG ATG GTA GCG ATG | 628 |
| GTA CCG TCC AGC CGC CGT CAG ACC AGG GAC CCC TAG GAC GAC ATA CTA | 676 |
| TAC CAC ACA CCT CTA TAA GGA AAG CTC GTA CTG CTT CTC TAG TAG TCC | 724 |
| CCG GTC CAA AAG AAG TCC GTC TCC CAG AGA AGT CTT ACA GTC GTA GAG | 772 |
| TAA TCT ACC ACG AAC CGG GAC TCT GGT AGT CTA TCC GGT TGG AAG CTT | 820 |
| CTT TAG GTC TTG GTA GGT ACC TAC GTT CTA CAA GAG GAC GGG GTC CTT | 868 |
| TGA CGA CTC TAG GTG GAG GTG TCG GAC AGC GGC CCC GGG TCG TTT | 913 |
|  ATCGTCGGA AAGACCGTCC AGGAGGGGAG AGAACAGTCT ACGGGTCCTC CCTTCGAAGA | 972 |
| CAGAGGTCGA AAGGGCTCAT GGTCACTGTG CAGAGCGGTT CGTCCTGTCA CGAACTATGT | 1032 |
| CCTTGTTGTA AATGTTGAGT AAGGTCTAGG GTCCGGGAC CTCCGACGGA GGGTTGTCAC | 1092 |
| CCCTTCTCAC TGAGAGGTCC CCAGGATCCG GAGTTGAGGA GGGTATCTAT GAGAGAAGAA | 1152 |
| GAGTATCCAC AGGTCGTAAC GACCTGAGAC TTTATAGGGC CCCCACCCCC CACCCCCACC | 1212 |
| CAGTCTTGGG ACGGTACCTT GACAAAGGAA GTAGTACTCA AGACGACTTA CGGCGCTACC | 1272 |
| CAGTCCATCC CCCCTTTGTC CAACCCTACC CTATCCTGAT CGTGGTAAAA TTCAGGGACA | 1332 |
| GTGGAGAAGG CTGAGAAAGA CTCACGGAAG ACACCCCTGA GGCCGACACG ACCCTCTTTA | 1392 |

```
TGAACTTGAA CGGAGAAAAT GGACGACGAA GAGGTTTTTA GACGGACCCA AAACAAGGGA    1452

TAAAAAGAGA GGACAGGAGG GAGTGGGGGA GGAAGTATAC TTTCCACGGT ACCTTCTCCG    1512

ATGTCCCGGT TTGCGACTCG GTGGACGGGA AAAAGAGGA GGAAATCATT TTGAGGCTCA     1572

CTTGACCAGA AGGAAAAACC AAAAATGAAT TGACAAAGTT TCGGTTCTGG AGTGTGTGTG    1632

TTTTTTACGT GTTTGTTACG TTAGTTGTCT TTTCGACATT TACACACATG TCAACCGTAC    1692

CATCATATGT TTTTCTAACA TCACCTAGAT TAAAAATTCT TTAAAACGGA AATTCAATAA    1752

AATGGACAAA AACAAGAAC AAAACTTTCT ACGCGTAAGA TTGGACCTCC AGTTACAATA     1812

CATAAATAAA TAAATAAATA AACCAAGGGA AGGATAAGGT TCGAAGCGAC GACGGGATCA    1872

AAAGAAAGGA GGAAAGGAGG AGACTGAACC CCTGGAAAAC CCCCTCCCGA CGCTGCGAAC    1932

GAGACAAACA CCCCACTGCC CTGAGTCCGC CCTGTCACGA CGTCGAGGGA CCGAAGACAC    1992

CCCGGGGAGT GGATGAATGG GTCCACCCAG GGCCGAGACA CCCACTACCC CTCCCCGTAA    2052

CGACTGACAC ATATATCCTA TTAATACTTT TCGTCAAGAC CTACCACACG GAAGGTCTAG    2112

GAGAGACCCC GACACAAAAC TCGTCGTCCA TCGGACGACC AAAATAGACT CACTTTATGA    2172

CATGTCCCCT TATTTTCTCT AGAATAAAAA AAAAAATATG AACCGCAAAA AACTTATTTT    2232

TGGAAAACAG AATTTTG                                                  2249

(2) INFORMATION FOR SEQ ID NO: 35:

(i) SEQUENCE CHARACTERISTICS:
        (A) LENGTH: 939 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 35:

ATGCTCTT GTCCAAAATC AACTCGCTTG                                       28

CCCACCTGCG CGCCCGCGCC TGCAACGACC TGCACGCCAC CAAGCTGGCG               78

CCGGGCAAGG AGAAGGAGCC CCTGGAGTCG CAGTACCAGG TGGGCCCGCT               128

ACTGGGCAGC GGCGGCTTCG GCTCGGTCTA CTCAGGCATC CGCGTCTCCG               178

ACAACTTGCC GGTGGCCATC AAACACGTGG AGAAGGACCG GATTTCCGAC               228

TGGGAGAGC TGCCTAATGG CACTCGAGTG CCCATGGAAG TGGTCCTGCT                278

GAAGAAGGTG AGCTCGGGTT TCTCCGGCGT CATTAGGCTC CTGGACTGGT               328

TCGAGAGGCC CGACAGTTTC GTCCTGATCC TGGAGAGGCC CGAGCCGGTG               378

CAAGATCTCT TCGACTTCAT CACGGAAAGG GGAGCCCTGC AAGAGGAGCT               428

GGCCCGCAGC TTCTTCTGGC AGGTGCTGGA GGCCGTGCGG CACTGCCACA               478

ACTGCGGGGT GCTCCACCGC GACATCAAGG ACGAAAACAT CCTTATCGAC               528

CTCAATCGCG GCGAGCTCAA GCTCATCGAC TTCGGGTCGG GGGCGCTGCT               578

CAAGGACACC GTCTACACGG ACTTCGATGG GACCCGAGTG TATAGCCCTC               628

CAGAGTGGAT CCGCTACCAT CGCTACCATG GCAGGTCGGC GGCAGTCTGG               678

TCCCTGGGGA TCCTGCTGTA TGATATGGTG TGTGGAGATA TTCCTTTCGA               728

GCATGACGAA GAGATCATCA GGGGCCAGGT TTTCTTCAGG CAGAGGGTCT               778

CTTCAGAATG TCAGCATCTC ATTAGATGGT GCTTGGCCCT GAGACCATCA               828

GATAGGCCAA CCTTCGAAGA AATCCAGAAC CATCCATGGA TGCAAGATGT               878
```

-continued

| | |
|---|---|
| TCTCCTGCCC CAGGAAACTG CTGAGATCCA CCTCCACAGC CTGTCGCCGG | 928 |
| GGCCCAGCAA A | 939 |

We claim:

TABLE II

Full Sequenced DNA and Deduced Protein Sequence for CR1

| | |
|---|---|
| AACCCAACCG CAGTTGACTA GCACCTGCTA CCGCGCCTTT GCTTCCTGGC GCACGCGGAG | 60 |
| CCTCCTGGAG CCTGCCACCA TCCTGCCTAC TACGTGCTGC CCTGCGCCCG CAGCC ATG<br>                                                                          Met<br>                                                                          1 | 118 |
| TGC CGC ACC CTG GCC GCC TTC CCC ACC ACC TGC CTG GAG AGA GCC AAA<br>Cys Arg Thr Leu Ala Ala Phe Pro Thr Thr Cys Leu Glu Arg Ala Lys<br>         5             10            15 | 166 |
| GAG TTC AAG ACA CGT CTG GGG ATC TTT CTT CAC AAA TCA GAG CTG GGC<br>Glu Phe Lys Thr Arg Leu Gly Ile Phe Leu His Lys Ser Glu Leu Gly<br>    20            25            30 | 214 |
| TGC GAT ACT GGG AGT ACT GGC AAG TTC GAG TGG GGC AGT AAA CAC AGC<br>Cys Asp Thr Gly Ser Thr Gly Lys Phe Glu Trp Gly Ser Lys His Ser<br>  35            40            45 | 262 |
| AAA GAG AAT AGA AAC TTC TCA GAA GAT GTG CTG GGG TGG AGA GAG TCG<br>Lys Glu Asn Arg Asn Phe Ser Glu Asp Val Leu Gly Trp Arg Glu Ser<br>50            55            60            65 | 310 |
| TTC GAC CTG CTG CTG AGC AGT AAA AAT GGA GTG GCT GCC TTC CAC GCT<br>Phe Asp Leu Leu Leu Ser Ser Lys Asn Gly Val Ala Ala Phe His Ala<br>         70            75            80 | 358 |
| TTC CTG AAG ACA GAG TTC AGT GAG GAG AAC CTG GAG TTC TGG CTG GCC<br>Phe Leu Lys Thr Glu Phe Ser Glu Glu Asn Leu Glu Phe Trp Leu Ala<br>    85            90            95 | 406 |
| TGT GAG GAG TTC AAG AAG ATC CGA TCA GCT ACC AAG CTG GCC TCC AGG<br>Cys Glu Glu Phe Lys Lys Ile Arg Ser Ala Thr Lys Leu Ala Ser Arg<br>  100           105           110 | 454 |
| GCA CAC CAG ATC TTT GAG GAG TTC ATT TGC AGT GAG GCC CCT AAA GAG<br>Ala His Gln Ile Phe Glu Glu Phe Ile Cys Ser Glu Ala Pro Lys Glu<br>115           120            125 | 502 |
| GTC AAC ATT GAC CAT GAG ACC CGC GAG CTG ACG AGG ATG AAC CTG CAG<br>Val Asn Ile Asp His Glu Thr Arg Glu Leu Thr Arg Met Asn Leu Gln<br>130           135          140          145 | 550 |
| ACT GCC ACA GCC ACA TGC TTT GAT GCG GCT CAG GGG AAG ACA CGT ACC<br>Thr Ala Thr Ala Thr Cys Phe Asp Ala Ala Gln Gly Lys Thr Arg Thr<br>         150          155          160 | 598 |
| CTG ATG GAG AAG GAC TCC TAC CCA CGC TTC CTG AAG TCG CCT GCT TAC<br>Leu Met Glu Lys Asp Ser Tyr Pro Arg Phe Leu Lys Ser Pro Ala Tyr<br>    165           170          175 | 646 |
| CGG GAC CTG GCT GCC CAA GCC TCA GCC GCC TCT GCC ACT CTG TCC AGC<br>Arg Asp Leu Ala Ala Gln Ala Ser Ala Ala Ser Ala Thr Leu Ser Ser<br>      180           185          190 | 694 |
| TGC AGC CTG GAC CAG CCC TCA CAC ACC (SEQ. ID No: 27)<br>Cys Ser Leu Asp Gln Pro Ser His Thr (SEQ. ID No: 2)<br>  195          200 | 721 |
| T GAGTCTCCAC GGCAGTGAGG | 742 |
| AAGCCAGCCG GGAAGAGAGG TTGAGTCACC CATCCCCGAG GTGGCTGCCC CTGTGTGGGA | 802 |
| GGCAGGTTCT GCAAAGCAAG TGCAAGAGGA CAAAAAAAAA AAAAAAAAAA AAAAATGCGC | 862 |
| TCCAGCAGCC TGTTTGGGAA GCAGCAGTCT CTCCTTCAGA TACTGTGGGA CTCATGCTGG | 922 |
| AGAGGAGCCG CCCACTTCCA GGACCTGTGA ATAAGGGCTA ATGATGAGGG TTGGTGGGGC | 982 |

TABLE II-continued

Full Sequenced DNA and Deduced Protein Sequence for CR1

```
TCTCTGTGGG GCAAAAAGGT GGTATGGGGG TTAGCACTGG CTCTCGTTCT CACCGGAGAA    1042

GGAAGTGTTC TAGTGTGGTT TAGGAAACAT GTGGATAAAG GGAACCATGA AAATGAGAGG    1102

AGGAAAGACA TCCAGATCAG CTGTTTTGCC TGTTGCTCAG TTGACTCTGA TTGCATCCTG    1162

TTTTCCTAAT TCCCAGACTG TTCTGGGCAC GGAAGGGACC CTGGATGTGG AGTCTTCCCC    1222

TTTGGCCCTC CTCACTGGCC TCTGGGCTAG CCCAGAGTCC CTTAGCTTGT ACCTCGTAAC    1282

ACTCCTGTGT GTCTGTCCAG CCTTGCAGTC ATGTCAAGGC CAGCAAGCTG ATGTGACTCT    1342

TGCCCCATGC GAGATATTTA TACCTCAAAC ACTGGCCTGT GAGCCCTTTC CAAGTCAGTG    1402

GAGAGCCCTG AAAGGAGCCT CACTTGAATC CAGCTCAGTG CTCTGGGTGG CCCCCTGCAG    1462

GTGCCCCCTG ACCCTGCGTT GCAGCAGGGT CCACCTGTGA GCAGGCCCGC CCTGGGCCCT    1522

CTTCCTGGAT GTGCCCTCTC TGAGTTCTGT GCTGTCTCTT GGAGGCAGGG CCCAGGAGAA    1582

CAAAGTGTGG AGGCCTCGGG GAGTGACTTT TCCAGCTCTC ATGCCCCGCA GTGTGGAACA    1642

AGGCAGAAAA GGATCCTAGG AAATAAGTCT CTTGGCGGTC CCTGAGAGTC CTGCTGAAAT    1702

CCAGCCAGTG TTTTTTGTGG TATGAGAACA GCCAAAAAGA GATGCCCCGA GATAGAAGGG    1762

GAGCCTTGTG TTTCTTTCCT GCAGACGTGA GATGAACACT GGAGTGGGCA GAGGTGGCCC    1822

AGGACCATGA CACCCTTAGA GTGCAGAAGC TGGGGGAGA GGCTGCTTCG AAGGGCAGGA     1882

CTGGGGATAA TCAGAACCTG CCTGTCACCT CAGGGCATCA CTGAACAAAC ATTTCCTGAT    1942

GGGAACTCCT GCGGCAGAGC CCAGGCTGGG GAAGTGAACT ACCCAGGGCA GCCCCTTTGT    2002

GGCCCAGGAT AATCAACACT GTTCTCTCTG TACCATGAGC TCCTCCAGGA GATTATTTAA    2062

GTGTATTGTA TCATTGGTTT TCTGTGATTG TCATAACATT GTTTTTGTTA CTGTTGGTGC    2122

TGTTGTTATT TATTATTGTA ATTTCAGTTT GCCTCTACTG GAGAATCTCA GCAGGGGTTT    2182

CAGCCTGACT GTCTCCCTTT CTCTACCAGA CTCTACCTCT GAATGTGCTG GGAACCTCTT    2242

GGAGCCTGTC AGGAACTCCT CACTGTTTAA ATATTTAGGT ATTGTGACAA ATGGAGCTGG    2302

TTTCCTAGAA ATGAATGATG TTTGCAATCC CCATTTTCCT GTTTCAGCAT GTTATATTCT    2362
                                                    |
TATGAAATAA AAGCCCAAGT CCAATATGAA AAAAAAAAAA AAAA (SEQ. ID No: 1)     2406
```

TABLE III

Full DNA Sequence and Deduced Protein Sequence for CR2

```
ATTTAGAGCA ACTCAGGAAA TAGGTGCACA CAAGCAAACC ATGTGGTTAA AGCCTTTGGA      60

ACTGGTTTGA GCAAAGCTGT AGGTGATTTG ACAAAATCAT CTGCAAAACC AGATTTCTAA    120

CACCTCCCTG CTGTGTATCT CATTTCTGCT GATGTGTGGT GCTTCATAAG ATG GGG        176
                                                         Met Gly
                                                          1

ACG TTA AGC ATG CAG CAA CTA CAG TCA TTT GTT CTC AGA GGT CTG GAC        224
Thr Leu Ser Met Gln Gln Leu Gln Ser Phe Val Leu Arg Gly Leu Asp
       5                   10                  15

CAA AGA GAA ACA AGA AAA GCT GGA GTC ACA CTA CCA AAG GCC GAA GCT        272
Gln Arg Glu Thr Arg Lys Ala Gly Val Thr Leu Pro Lys Ala Glu Ala
   20                  25                  30

GAG CAA CAG AGC TCT GGA GTC AGC TGC CTG GGT TCA GCA TGC AGC GCT        320
Glu Gln Gln Ser Ser Gly Val Ser Cys Leu Gly Ser Ala Cys Ser Ala
   35                  40                  45                  50

GCC GTG GAC GAT CTG TCT CTC TTG CAT ATA (SEQ. ID No: 28)               350
```

TABLE III-continued

Full DNA Sequence and Deduced Protein Sequence for CR2

Ala Val Asp Asp Leu Ser Leu Leu His Ile (SEQ. ID No: 4)
            55                      60

| | |
|---|---:|
| T GACTTACCAG TTTTACTTTC | 371 |
| AGTCTCTCCA TTTCTAATTA AATGAGATGC AGAAATGCTG GTGCCTTGCT ATGATGTTTG | 431 |
| CAGTTATTAT TTCTAGGAAA AAAAATATTA TTGTTACTCA GTATCTGGTC TAGCTACTTG | 491 |
| GACAACTGGA CTATCCCCCT CCTTTCAAGG GAGGGCAAAG CATTTCAGAA AAGAACTAAG | 551 |
| TGCTATTTCT CTGCTTCAGG AATGTCTCCC GTATGTAAAA GAATGTGGCT TCAGGGAGTA | 611 |
| GCATGTGTTG TAAAGGTGGA TGGGTCTAAC TTCATGGACA GCTCTGACAT CCACTAGCTA | 671 |
| TGCCACCTGA TGCAAACCAC TTGGGCTGTC TGCAGTTTCG TTTATCTTTC TGGAATTGGT | 731 |
| AATAACAACC ACCTGGCAAG ATCACTGTTA TGAATACGGA GGATCAAAGT TGTGAAGTTA | 791 |
| TTTTGTAAAG TGAAATGTTC TGAAAAATGG ATTTTAACAG TGTCAGCGAA AAGTAGATTT | 851 |
| TTGACATTTA TCAAGAGTTC AGCTAATGAA AACAAGTATG GATAATAGTT ACATAGAACT | 911 |
| GTCTACTTTA CTCAGTACTT TAGCATATGC TATTATATTT AATCTTCTTA AAAAGTAGGA | 971 |
| AATTATACAA GCCATGTATT GATATTATTG TGGTGGTTGT CGTTCTCAAT TACACACTGA | 1031 |
| ATATTAAGAC CTCTCAGGTA GCAGCTGGAA GGACATTGTA TCCAGTTTCC TGATTGTTTT | 1091 |
| CAATGGAATA ATCATGTATA CATGCACTAC TAATGAGACA ATGGTGATTC TAAAAGCTTA | 1151 |
| ATCAGGGGGA CTTTTGTGTA TTCCAAATCT ACTAAAAATA AAGAAACACA GAAATGAGAA | 1211 |
| AAAAAAAAAA AA (SEQ. ID No: 3) | 1223 |

TABLE IV

Full DNA and Protein Sequences for CR3

| | |
|---|---:|
| CGCGGGAGCC TCGAGCGCCG CTCGGATGCA GAAGCCGAGC CGCCACTCGG CGCGCGGTGG | 60 |
| GAGACCCAGG GCAAGCCGCC GTCGGCGCGC TGGGTGCGGG AAGGGGGCTC TGGATTTCGG | 120 |
| TCCCTCCCCT TTTTCCTCTG AGTCTCGGAA CGCTCCAGAT CTCAGACCCT CTTCCTCCCA | 180 |
| GGTAAAGGCC GGGAGAGGAG GGCGCATCTC TTTTCCAGGC ACCCCACC <u>ATG GGA AAT</u> | 237 |

<u></u>                                                Met Gly Asn
                                                         1

<u>GCC TCC AAT GAC TCC CAG TCT GAG GAC TGC GAG ACG CGA CAG TGG TTT</u>    285
Ala Ser Asn Asp Ser Gln Ser Glu Asp Cys Glu Thr Arg Gln Trp Phe
      5                  10                  15

<u>CCC CCA GGC GAA AGC CCA GCC ATC AGT TCC GTC ATG TTC TCG GCC GGG</u>    333
Pro Pro Gly Glu Ser Pro Ala Ile Ser Ser Val Met Phe Ser Ala Gly
 20                  25                  30                  35

<u>GTG CTG GGG AAC CTC ATA GAA CTG GCG CTG CTG GCG CGC CGC TGG CAG</u>    381
Val Leu Gly Asn Leu Ile Glu Leu Ala Leu Leu Ala Arg Arg Trp Gln
              40                  45                  50

<u>GGG GAC GTG GGG TGC AGC GCC GGC CGT AGG AGC TCC CTC TCC TTG TTC</u>    429
Gly Asp Val Gly Cys Ser Ala Gly Arg Arg Ser Ser Leu Ser Leu Phe
              55                  60                  65

<u>CAC GTG CTG GTG ACC GAG CTG GTG TTC ACC GAC CTG CTC GGG ACC TGC</u>    477
His Val Leu Val Thr Glu Leu Val Phe Thr Asp Leu Leu Gly Thr Cys
         70                  75                  80

<u>CTC ATC AGC CCA GTG GTA CTG GCT TCG TAC GCG CGG AAC CAG ACC CTG</u>    525
Leu Ile Ser Pro Val Val Leu Ala Ser Tyr Ala Arg Asn Gln Thr Leu
     85                  90                  95

<u>GTG GCA CTG GCG CCC GAG AGC CGC GCG TCC ACC TAC TTC GCT TTC GCC</u>    573

TABLE IV-continued

Full DNA and Protein Sequences for CR3

```
Val Ala Leu Ala Pro Glu Ser Arg Ala Ser Thr Tyr Phe Ala Phe Ala
100             105                 110                 115

ATG ACC TTC TTC AGC CTG GCC ACG ATG CTC ATG CTC TTC ACC ATG GCC      621
Met Thr Phe Phe Ser Leu Ala Thr Met Leu Met Leu Phe Thr Met Ala
                120                 125                 130

CTG GAG CGC TAC CTC TCG ATC GGG CAC CCC TAC TTC TAC CAG CGC CGC      669
Leu Glu Arg Tyr Leu Ser Ile Gly His Pro Tyr Phe Tyr Gln Arg Arg
            135                 140                 145

GTC TCG CGC TCC GGG GGC CTG GCC GTG CTG CCT GTC ATC TAT GCA GTC      717
Val Ser Arg Ser Gly Gly Leu Ala Val Leu Pro Val Ile Tyr Ala Val
        150                 155                 160

TCC CTG CTC TTC TGC TCA CTG CCG CTG CTG GAC TAT GGG CAG TAC GTC      765
Ser Leu Leu Phe Cys Ser Leu Pro Leu Leu Asp Tyr Gly Gln Tyr Val
    165                 170                 175

CAG TAC TGC CCC GGG ACC TGG TGC TTC ATC CGG CAC GGG CGG ACC GCT      813
Gln Tyr Cys Pro Gly Thr Trp Cys Phe Ile Arg His Gly Arg Thr Ala
180                 185                 190                 195

TAC CTG CAG CTG TAC GCC ACC CTG CTG CTG CTT CTC ATT GTC TCG GTG      861
Tyr Leu Gln Leu Tyr Ala Thr Leu Leu Leu Leu Leu Ile Val Ser Val
                200                 205                 210

CTC GCC TGC AAC TTC AGT GTC ATT CTC AAC CTC ATC CGC ATG CAC CGC      909
Leu Ala Cys Asn Phe Ser Val Ile Leu Asn Leu Ile Arg Met His Arg
                215                 220                 225

CGA AGC CGG AGA AGC CGC TGC GGA CCT TCC CTG GGC AGT GGC CGG GGC      957
Arg Ser Arg Arg Ser Arg Cys Gly Pro Ser Leu Gly Ser Gly Arg Gly
            230                 235                 240

GGC CCC GGG GCC CGC AGG AGA GGG GAA AGG GTG TCC ATG GCG GAG GAG     1005
Gly Pro Gly Ala Arg Arg Arg Gly Glu Arg Val Ser Met Ala Glu Glu
        245                 250                 255

ACG GAC CAC CTC ATT CTC CTG GCT ATC ATG ACC ATC ACC TTC GCC GTC     1053
Thr Asp His Leu Ile Leu Leu Ala Ile Met Thr Ile Thr Phe Ala Val
260                 265                 270                 275

TGC TCC TTG CCT TTC ACG ATT TTT GCA TAT ATG AAT GAA ACC TCT TCC     1101
Cys Ser Leu Pro Phe Thr Ile Phe Ala Tyr Met Asn Glu Thr Ser Ser
                280                 285                 290

CGA AAG GAA AAA TGG GAC CTC CAA GCT CTT AGG TTT TTA TCA ATT AAT     1149
Arg Lys Glu Lys Trp Asp Leu Gln Ala Leu Arg Phe Leu Ser Ile Asn
            295                 300                 305

TCA ATA ATT GAC CCT TGG GTC TTT GCC ATC CTT AGG CCT CCT GTT CTG     1197
Ser Ile Ile Asp Pro Trp Val Phe Ala Ile Leu Arg Pro Pro Val Leu
        310                 315                 320

AGA CTA ATG CGT TCA GTC CTC TGT TGT CGG ATT TCA TTA AGA ACA CAA     1245
Arg Leu Met Arg Ser Val Leu Cys Cys Arg Ile Ser Leu Arg Thr Gln
325                 330                 335

GAT GCA ACA CAA ACT TCC TGT TCT ACA CAG TCA GAT GCC AGT AAA CAG     1293
Asp Ala Thr Gln Thr Ser Cys Ser Thr Gln Ser Asp Ala Ser Lys Gln
340                 345                 350                 355

GCT GAC CTT  (SEQ. ID No: 29)                                        1302
Ala Asp Leu  (SEQ. ID No: 6)
      357

T GAGGTCAGTA GTTTAAAAGT TCTTAGTTAT ATAGCATCTG                        1343

GAAGATCATT TTGAAATTGT TCCTTGGAGA AATGAAAACA GTGTGTAAAC AAAATGAAGC    1403

TGCCCTAATA AAAAGGAGTA TACAAACATT TAAGCTGTGG TCAAGGCTAC AGATGTGCTG    1463

ACAAGGCACT TCATGTAAAG TGTCAGAAGG AGCTACAAAA CCTACCCTCA GTGAGCATGG    1523

TACTTGGCCT TTGGAGGAAC AATCGGCTGC ATTGAAGATC CAGCTGCCTA TTGATTTAAG    1583
```

TABLE IV-continued
Full DNA and Protein Sequences for CR3

| | | | | | |
|---|---|---|---|---|---|
| CTTTCCTGTT | GAATGACAAA | GTATGTGGTT | TTGTAATTTG | TTTGAAACCC | CAAACAGTGA | 1643 |
| CTGTACTTTC | TATTTTAATC | TTGCTACTAC | CGTTATACAC | ATATAGTGTA | CAGCCAGACC | 1703 |
| AGATTAAACT | TCATATGTAA | TCTCTAGGAA | GTCAATATGT | GGAAGCAACC | AAGCCTGCTG | 1763 |
| TCTTGTGATC | ACTTAGCGAA | CCCTTTATTT | GAACAATGAA | GTTGAAAATC | ATAGGCACCT | 1823 |
| TTTACTGTGA | TGTTTGTGTA | TGTGGGAGTA | CTCTCATCAC | TACAGTATTA | CTCTTACAAG | 1883 |
| AGTGGACTCA | GTGGGTTAAC | ATCAGTTTTG | TTTACTCATC | CTCCAGGAAC | TGCAGGTCAA | 1943 |
| GTTGTCAGGT | TATTTATTTT | ATAATGTCCA | TATGCTAATA | GTGATCAAGA | AGACTTTAGG | 2003 |
| AATGGTTCTC | TCAACAAGAA | ATAATAGAAA | TGTCTCAAGG | CAGTTAATTC | TCATTAATAC | 2063 |
| TCTTTATCCT | ATTTCTGGGG | GAGGATGTAC | GTGGCCATGT | ATGAAGCCAA | ATATTAGGCT | 2123 |
| TAAAAACTGA | AAAATCTGGT | TCATTCTTCA | GATATACTGG | AACCCTTTTA | AAGTTGATAT | 2183 |
| TGGGGCCATG | AGTAAAATAG | ATTTTATAAG | ATGACTGTGT | TGTACTAAAA | TTCATCTGTC | 2243 |
| TATATTTTAT | TTAGGGGACA | TGGTTTGACT | CATCTTATAT | GGGAAACCAT | GTAGCAGTGA | 2303 |
| GTCATATCTT | AATATATTTC | TAAATGTTTG | GCATGTAAAC | GTAAACTCAG | CATCACAATA | 2363 |
| TTTCAGTGAA | TTTGCACTGT | TTAATCATAG | TTACTGTGTA | AACTCATCTG | AAATGTTACC | 2423 |
| AAAAATAAAC | TATAAAACAA | AATTTGA | (SEQ ID No: 5) | | | 2450 |

TABLE V
Full DNA and Deduced Protein Sequence for CR4

| | | | | | |
|---|---|---|---|---|---|
| GGGGGGAAAG | GAAAATAATA | CAATTTCAGG | GGAAGTCGCC | TTCAGGTCTG | CTGCTTTTTT | 60 |
| ATTTTTTTTT | TTTTAATTAA | AAAAAAAAAG | GACATAGAAA | ACATCAGTCT | TGAACTTCTC | 120 |
| TTCAAGAACC | CGGGCTGCAA | AGGAAATCTC | CTTTGTTTTT | GTTATTTATG | TGCTGTCAAG | 180 |
| TTTTGAAGTG | GTGATCTTTA | GACAGTGACT | GAGT <u>ATG GAT CAT TTG AAC GAG</u> | | | 232 |
| | | | Met Asp His Leu Asn Glu | | |
| | | | 1 5 | | |

<u>GCA ACT CAG GGG AAA GAA CAT TCA GAA ATG TCT AAC AAT GTG AGT GAT</u>  280
Ala Thr Gln Gly Lys Glu His Ser Glu Met Ser Asn Asn Val Ser Asp
          10                    15                   20

<u>CCG AAG GGT CCA CCA GCC AAG ATT GCC CGC CTG GAG CAG AAC GGG AGC</u>  328
Pro Lys Gly Pro Pro Ala Lys Ile Ala Arg Leu Glu Gln Asn Gly Ser
          25                    30                   35

<u>CCG CTA GGA AGA GGA AGG CTT GGG AGT ACA GGT GCA AAA ATG CAG GGA</u>  376
Pro Leu Gly Arg Gly Arg Leu Gly Ser Thr Gly Ala Lys Met Gln Gly
          40                    45                   50

<u>GTG CCT TTA AAA CAC TCG GGC CAT CTG ATG AAA ACC AAC CTT AGG AAA</u>  424
Val Pro Leu Lys His Ser Gly His Leu Met Lys Thr Asn Leu Arg Lys
55                  60                    65                   70

<u>GGA ACC ATG CTG CCA GTT TTC TGT GTG GTG GAA CAT TAT GAA AAC GCC</u>  472
Gly Thr Met Leu Pro Val Phe Cys Val Val Glu His Tyr Glu Asn Ala
                  75                    80                   85

<u>ATT GAA TAT GAT TGC AAG GAG GAG CAT GCA GAA TTT GTG CTG GTG AGA</u>  520
Ile Glu Tyr Asp Cys Lys Glu Glu His Ala Glu Phe Val Leu Val Arg
          90                    95                   100

<u>AAG GAT ATG CTT TTC AAC CAG CTG ATC GAA ATG GCA TTG CTG TCT CTA</u>  568
Lys Asp Met Leu Phe Asn Gln Leu Ile Glu Met Ala Leu Leu Ser Leu
          105                   110                 115

<u>GGT TAT TCA CAT AGC TCT GCT GCC CAG GCC AAA GGG CTA ATC CAG GTT</u>  616
Gly Tyr Ser His Ser Ser Ala Ala Gln Ala Lys Gly Leu Ile Gln Val

TABLE V-continued

Full DNA and Deduced Protein Sequence for CR4

```
                120                     125                     130
GGA AAG TGG AAT CCA GTT CCA CTG TCT TAC GTG ACA GAT GCC CCT GAT     664
Gly Lys Trp Asn Pro Val Pro Leu Ser Tyr Val Thr Asp Ala Pro Asp
135             140                     145                     150

GCT ACA GTA GCA GAT ATG CTT CAA GAT GTG TAT CAT GTG GTC ACA TTG     712
Ala Thr Val Ala Asp Met Leu Gln Asp Val Tyr His Val Val Thr Leu
                    155                     160                     165

AAA ATT CAG TTA CAC AGT TGC CCC AAA CTA GAA GAC TTG CCT CCC GAA     760
Lys Ile Gln Leu His Ser Cys Pro Lys Leu Glu Asp Leu Pro Pro Glu
                170                     175                     180

CAA TGG TCG CAC ACC ACA GTG AGG AAT GCT CTG AAG GAC TTA CTG AAA     808
Gln Trp Ser His Thr Thr Val Arg Asn Ala Leu Lys Asp Leu Leu Lys
        185                     190                     195

GAT ATG AAT CAG AGT TCA TTG GCC AAG GAG TGC CCC CTT TCA CAG AGT     856
Asp Met Asn Gln Ser Ser Leu Ala Lys Glu Cys Pro Leu Ser Gln Ser
    200                     205                     210

ATG ATT TCT TCC ATT GTG AAC AGT ACT TAC TAT GCA AAT GTC TCA GCA     904
Met Ile Ser Ser Ile Val Asn Ser Thr Tyr Tyr Ala Asn Val Ser Ala
215                     220                     225                     230

GCA AAA TGT CAA GAA TTT GGA AGG TGG TAC AAA CAT TTC AAG AAG ACA     952
Ala Lys Cys Gln Glu Phe Gly Arg Trp Tyr Lys His Phe Lys Lys Thr
                    235                     240                     245

AAA GAT ATG ATG GTT GAA ATG GAT AGT CTT TCT GAG CTA TCC CAG CAA    1000
Lys Asp Met Met Val Glu Met Asp Ser Leu Ser Glu Leu Ser Gln Gln
                250                     255                     260

GGC GCC AAT CAT GTC AAT TTT GGC CAG CAA CCA GTT CCA GGG AAC ACA    1048
Gly Ala Asn His Val Asn Phe Gly Gln Gln Pro Val Pro Gly Asn Thr
            265                     270                     275

GCC GAG CAG CCT CCA TCC CCT GCG CAG CTC TCC CAT GGC AGC CAG CCC    1096
Ala Glu Gln Pro Pro Ser Pro Ala Gln Leu Ser His Gly Ser Gln Pro
280                     285                     290

TCT GTC CGG ACA CCT CTT CCA AAC CTG CAC CCT GGG CTC GTA TCA ACA    1144
Ser Val Arg Thr Pro Leu Pro Asn Leu His Pro Gly Leu Val Ser Thr
295                     300                     305                     310

CCT ATC AGT CCT CAA TTG GTC AAC CAG CAG CTG GTG ATG GCT CAG CTG    1192
Pro Ile Ser Pro Gln Leu Val Asn Gln Gln Leu Val Met Ala Gln Leu
                315                     320                     325

CTG AAC CAG CAG TAT GCA GTG AAT AGA CTT TTA GCC CAG CAG TCC TTA    1240
Leu Asn Gln Gln Tyr Ala Val Asn Arg Leu Leu Ala Gln Gln Ser Leu
                330                     335                     340

AAC CAA CAA TAC TTG AAC CAC CCT CCC CCT GTC AGT AGA TCT ATG AAT    1288
Asn Gln Gln Tyr Leu Asn His Pro Pro Pro Val Ser Arg Ser Met Asn
            345                     350                     355

AAG CCT TTG GAG CAA CAG GTT TCG ACC AAC ACA GAG GTG TCT TCC GAA    1336
Lys Pro Leu Glu Gln Gln Val Ser Thr Asn Thr Glu Val Ser Ser Glu
        360                     365                     370

ATC TAC CAG TGG GTA CGC GAT GAA CTG AAA CGA GCA GGA ATC TCC CAG    1384
Ile Tyr Gln Trp Val Arg Asp Glu Leu Lys Arg Ala Gly Ile Ser Gln
375                     380                     385                     390

GCG GTA TTT GCA CGT GTG GCT TTT AAC AGA ACT CAG GGC TTG CTT TCA    1432
Ala Val Phe Ala Arg Val Ala Phe Asn Arg Thr Gln Gly Leu Leu Ser
                    395                     400                     405

GAA ATC CTC CGA AAG GAA GAG GAC CCC AAG ACT GCA TCC CAG TCT TTG    1480
Glu Ile Leu Arg Lys Glu Glu Asp Pro Lys Thr Ala Ser Gln Ser Leu
                410                     415                     420

CTG GTA AAC CTT CGG GCT ATG CAG AAT TTC TTG CAG TTA CCG GAA GCT    1528
Leu Val Asn Leu Arg Ala Met Gln Asn Phe Leu Gln Leu Pro Glu Ala
            425                     430                     435
```

TABLE V-continued

Full DNA and Deduced Protein Sequence for CR4

| | |
|---|---|
| GAA AGA GAC CGA ATA TAC CAG GAC GAA AGG GAA AGG AGC TTG AAT GCT<br>Glu Arg Asp Arg Ile Tyr Gln Asp Glu Arg Glu Arg Ser Leu Asn Ala<br>440                        445                        450 | 1576 |
| GCC TCG GCC ATG GGT CCT GCC CCC CTC ATC AGC ACA CCA CCC AGC CGT<br>Ala Ser Ala Met Gly Pro Ala Pro Leu Ile Ser Thr Pro Pro Ser Arg<br>455                      460                      465                      470 | 1624 |
| CCT CCC CAG GTG AAA ACA GCT ACT ATT GCC ACT GAA AGG AAT GGG AAA<br>Pro Pro Gln Val Lys Thr Ala Thr Ile Ala Thr Glu Arg Asn Gly Lys<br>                      475                      480                      485 | 1672 |
| CCA GAG AAC AAT ACC ATG AAC ATT AAT GCT TCC ATT TAT GAT GAG ATT<br>Pro Glu Asn Asn Thr Met Asn Ile Asn Ala Ser Ile Tyr Asp Glu Ile<br>                  490                      495                      500 | 1720 |
| CAG CAG GAA ATG AAG CGT GCT AAA GTG TCT CAA GCA CTG TTT GCA AAG<br>Gln Gln Glu Met Lys Arg Ala Lys Val Ser Gln Ala Leu Phe Ala Lys<br>                  505                      510                      515 | 1768 |
| GTT GCA GCA ACC AAA AGC CAG GGA TGG TTG TGC GAG CTG TTA CGC TGG<br>Val Ala Ala Thr Lys Ser Gln Gly Trp Leu Cys Glu Leu Leu Arg Trp<br>520                        525                      530 | 1816 |
| AAA GAA GAT CCT TCT CCA GAA AAC AGA ACC CTG TGG GAG AAC CTC TCC<br>Lys Glu Asp Pro Ser Pro Glu Asn Arg Thr Leu Trp Glu Asn Leu Ser<br>535                        540                      545                      550 | 1864 |
| ATG ATC CGA AGG TTC CTC AGT CTT CCT CAG CCA GAA CGT GAT GCC ATT<br>Met Ile Arg Arg Phe Leu Ser Leu Pro Gln Pro Glu Arg Asp Ala Ile<br>                  555                      560                      565 | 1912 |
| TAT GAA CAG GAG AGC AAC GCG GTG CAT CAC CAT GGC GAC AGG CCG CCC<br>Tyr Glu Gln Glu Ser Asn Ala Val His His His Gly Asp Arg Pro Pro<br>                  570                      575                      580 | 1960 |
| CAC ATT ATC CAT GTT CCA GCA GAG CAG ATT CAG CAA CAG CAG CAG CAA<br>His Ile Ile His Val Pro Ala Glu Gln Ile Gln Gln Gln Gln Gln Gln<br>                  585                      590                      595 | 2008 |
| CAG CAA CAG CAG CAG CAG CAG CAG GCA CCG CCG CCT CCA CAG CCA<br>Gln Gln Gln Gln Gln Gln Gln Gln Ala Pro Pro Pro Pro Gln Pro<br>600                        605                      610 | 2056 |
| CAG CAG CAG CCA CAG ACA GGC CCT CGG CTC CCC CCA CGG CAA CCC ACG<br>Gln Gln Gln Pro Gln Thr Gly Pro Arg Leu Pro Pro Arg Gln Pro Thr<br>615                        620                      625                      630 | 2104 |
| GTG GCC TCT CCA GCA GAG TCA GAT GAG GAA AAC CGA CAG AAG ACC CGG<br>Val Ala Ser Pro Ala Glu Ser Asp Glu Glu Asn Arg Gln Lys Thr Arg<br>                  635                      640                      645 | 2152 |
| CCA CGA ACA AAA ATT TCA GTG GAA GCC TTG GGA ATC CTC CAG AGT TTC<br>Pro Arg Thr Lys Ile Ser Val Glu Ala Leu Gly Ile Leu Gln Ser Phe<br>                  650                      655                      660 | 2200 |
| ATA CAA GAC GTG GGC CTG TAC CCT GAC GAA GAG GCC ATC CAG ACT CTG<br>Ile Gln Asp Val Gly Leu Tyr Pro Asp Glu Glu Ala Ile Gln Thr Leu<br>                  665                      670                      675 | 2248 |
| TCT GCC CAG CTC GAC CTT CCC AAG TAC ACC ATC ATC AAG TTC TTT CAG<br>Ser Ala Gln Leu Asp Leu Pro Lys Tyr Thr Ile Ile Lys Phe Phe Gln<br>680                        685                      690 | 2296 |
| AAC CAG CGG TAC TAT CTC AAG CAC CAC GGC AAA CTG AAG GAC AAT TCC<br>Asn Gln Arg Tyr Tyr Leu Lys His His Gly Lys Leu Lys Asp Asn Ser<br>695                        700                      705                      710 | 2344 |
| GGT TTA GAG GTC GAT GTG GCA GAA TAT AAA GAA GAG GAG CTG CTG AAG<br>Gly Leu Glu Val Asp Val Ala Glu Tyr Lys Glu Glu Glu Leu Leu Lys<br>                  715                      720                      725 | 2392 |
| GAT TTG GAA GAG AGT GTC CAA GAT AAA AAT ACT AAC ACC CTT TTT TCA<br>Asp Leu Glu Glu Ser Val Gln Asp Lys Asn Thr Asn Thr Leu Phe Ser<br>                  730                      735                      740 | 2440 |

TABLE V-continued

Full DNA and Deduced Protein Sequence for CR4

| | |
|---|---:|
| GTG AAA CTA GAA GAA GAG CTG TCA GTG GAA GGA AAC ACA GAC ATT AAT<br>Val Lys Leu Glu Glu Glu Leu Ser Val Glu Gly Asn Thr Asp Ile Asn<br>745                    750                    755 | 2488 |
| ACT GAT TTG AAA GAC (SEQ. ID No: 30)<br>Thr Asp Leu Lys Asp (SEQ. ID No: 8)<br>   760            763 | 2503 |
| TGAGATAAAA GTATTTGTTT CGTTCAACAG TGCCACTGGT | 2543 |
| ATTTACTAAC AAAATGAAAA GTCCACCTTG TCTTCTCTCA GAAAACCTTT GTTGTTCATT | 2603 |
| GTTTGGCCAA TGAACTTTCA AAAACTTGCA CAAACAGAAA AGTTGGAAAA GGATAATACA | 2663 |
| GACTGCACTA AATGTTTTCC TCTGTTTTAC AAACTGCTTG GCAGCCCCAG GTGAAGCATC | 2723 |
| AAGGATTGTT TGGTATTAAA ATTTGTGTTC ACGGGATGCA CCAAAGTGTG TACCCCGTAA | 2783 |
| GCATGAAACC AGTGTTTTTT GTTTTTTTTT TAGTTCTTAT TCCGGAGCCT CAAACAAGCA | 2843 |
| TTATACCTTC TGTGATTATG ATTTCCTCTC CTATAATTAT TTCTGTAGCA CTCCACACTG | 2903 |
| ATCTTTGGAA ACTTGCCCCT TATTTAAAAA AAAAAAAAA AAA (SEQ. ID No: 7) | 2946 |

TABLE VI

Full DNA and Deduced Protein Sequence for CR5

| | |
|---|---:|
| CGCCCGCGCG CCCCGGGAGC CTACCCAGCA CGCGCTCCGC GCCCACTGGT TCCCTCCAGC | 60 |
| CGCCGCCGTC CAGCCGAGTC CCCACTCCGG AGTCGCCGCT GCCGCGGGA C ATG GTC<br>                                                                                   Met Val<br>                                                                                   1 | 117 |
| CTC TGC GTT CAG GGA CCT CGT CCT TTG CTG GCT GTG GAG CGG ACT GGG<br>Leu Cys Val Gln Gly Pro Arg Pro Leu Leu Ala Val Glu Arg Thr Gly<br>            5                    10                    15 | 165 |
| CAG CGG CCC CTG TGG GCC CCG TCC CTG GAA CTG CCC AAG CCA GTC ATG<br>Gln Arg Pro Leu Trp Ala Pro Ser Leu Glu Leu Pro Lys Pro Val Met<br>      20                    25                    30 | 213 |
| CAG CCC TTG CCT GCT GGG GCC TTC CTC GAG GAG GTG GCA GAG GGT ACC<br>Gln Pro Leu Pro Ala Gly Ala Phe Leu Glu Glu Val Ala Glu Gly Thr<br>35                    40                    45                    50 | 261 |
| CCA GCC CAG ACA GAG AGT GAG CCA AAG GTG CTG GAC CCA GAG GAG GAT<br>Pro Ala Gln Thr Glu Ser Glu Pro Lys Val Leu Asp Pro Glu Glu Asp<br>                  55                    60                    65 | 309 |
| CTG CTG TGC ATA GCC AAG ACC TTC TCC TAC CTT CGG GAA TCT GGC TGG<br>Leu Leu Cys Ile Ala Lys Thr Phe Ser Tyr Leu Arg Glu Ser Gly Trp<br>              70                    75                    80 | 357 |
| TAT TGG GGT TCC ATT ACG GCC AGC GAG GCC CGA CAA CAC CTG CAG AAG<br>Tyr Trp Gly Ser Ile Thr Ala Ser Glu Ala Arg Gln His Leu Gln Lys<br>85                    90                                95 | 405 |
| ATG CCA GAA GGC ACG TTC TTA GTA CGT GAC AGC ACG CAC CCC AGC TAC<br>Met Pro Glu Gly Thr Phe Leu Val Arg Asp Ser Thr His Pro Ser Tyr<br>100                  105                 110 | 453 |
| CTG TTC ACG CTG TCA GTG AAA ACC ACT CGT GGC CCC ACC AAT GTA CGC<br>Leu Phe Thr Leu Ser Val Lys Thr Thr Arg Gly Pro Thr Asn Val Arg<br>115                 120               125               130 | 501 |
| ATT GAG TAT GCC GAC TCC AGC TTC CGT CTG GAC TCC AAC TGC TTG TCC<br>Ile Glu Tyr Ala Asp Ser Ser Phe Arg Leu Asp Ser Asn Cys Leu Ser<br>                 135               140               145 | 549 |
| AGG CCA CGC ATC CTG GCC TTT CCG GAT GTG GTC AGC CTT GTG CAG CAC<br>Arg Pro Arg Ile Leu Ala Phe Pro Asp Val Val Ser Leu Val Gln His<br>                150                 155               160 | 597 |

TABLE VI-continued

Full DNA and Deduced Protein Sequence for CR5

```
TAT GTG GCC TCC TGC ACT GCT GAT ACC CGA AGC GAC AGC CCC GAT CCT        645
Tyr Val Ala Ser Cys Thr Ala Asp Thr Arg Ser Asp Ser Pro Asp Pro
        165                 170                 175

GCT CCC ACC CCG GCC CTG CCT ATG CCT AAG GAG GAT GCG CCT AGT GAC        693
Ala Pro Thr Pro Ala Leu Pro Met Pro Lys Glu Asp Ala Pro Ser Asp
        180                 185                 190

CCA GCA CTG CCT GCT CCT CCA CCA GCC ACT GCT GTA CAC CTA AAA CTG        741
Pro Ala Leu Pro Ala Pro Pro Pro Ala Thr Ala Val His Leu Lys Leu
195                 200                 205                 210

GTG CAG CCC TTT GTA CGC AGA AGA AGT GCC CGC AGC CTG CAA CAC CTG        789
Val Gln Pro Phe Val Arg Arg Arg Ser Ala Arg Ser Leu Gln His Leu
                215                 220                 225

TGC CGC CTT GTC ATC AAC CGT CTG GTG GCC GAC GTG GAC TGC CTG CCA        837
Cys Arg Leu Val Ile Asn Arg Leu Val Ala Asp Val Asp Cys Leu Pro
        230                 235                 240

CTG CCC CGG CGC ATG GCC GAC TAC CTC CGA CAG TAC CCC TTC CAG CTC        885
                                             (SEQ: ID No: 33)
Leu Pro Arg Arg Met Ala Asp Tyr Leu Arg Gln Tyr Pro Phe Gln Leu
        245                 250                 255 (SEQ. ID No: 10)

GACTGTACGG GGCAATCTGC CCACCCTCAC CCAGTCGCAC CCTGGAGGGG ACATCAGCCC       946

CAGCTGGACT TGGGCCCCCA CTGTCCCTCC TCCAGGCATC CTGGTGCCTG CATACCTCTG      1006

GCAGCTGGCC CAGGAAGAGC CAGCAAGAGC AAGGCATGGG AGAGGGGAGG TGTCACACAA      1066

CTTGGAGGTA AATGCCCCCA GGCCGCATGT GGCTTCATTA TACTGAGCCA TGTGTCAGAG      1126

GATGGGAGA CAGGCAGGAC CTTGTCTCAC CTGTGGGCTG GGCCCAGACC TCCACTCGCT       1186

TGCCTGCCCT GGCCACCTGA ACTGTATGGG CACTCTCAGC CCTGGTTTTT CAATCCCCAG      1246

GGTCGGGTAG GACCCCTACT GGCAGCCAGC CTCTGTTTCT GGGAGGATGA CATGCAGAGG      1306

AACTGAGATC GACAGTGACT AGTGACCCCT TGTTGAGGGG TAAGCCAGGC TAGGGGACTG      1366

CACAATTATA CACTCCTGAG CCCTGGTAGT CCAGAGACCC AACTCTGCC CTGGCTTCTC      1426

TGGTTCTTCC CTGTGGAAAG CCCATCCTGA GACATCTTGC TGGAACCAAG GCAATCCTGG      1486

ATGTCCTGGT ACTGACCCAC CCGTCTGTGA ATGTGTCCAC TCTCTTCTGC CCCCAGCCAT      1546

ATTTGGGGAG GATGGACAAC TACAATAGGT AAGAAAATGC AGCCGGAGCC TCAGTCCCCA      1606

GCAGAGCCTG TGTCTCACCC CCTCACAGGA CAGAGCTGTA TCTGCATAGA GCTGGTCTCA      1666

CTGTGGCGCA GGCCCCGGGG GGAGTGCCTG TGCTGTCAGG AAGAGGGGGT GCTGGTTTGA      1726

GGGCCACCAC TGCAGTTCTG CTAGGTCTGC TTCCTGCCCA GGAAGGTGCC TGCACATGAG      1786

AGGAGAGAAA TACACGTCTG ATAAGACTTC ATGAAATAAT AATTATAGCA AGAACAGTT      1846

TGGTGGTCTT TTCTCTTCCA CTGATTTTTC TGTAATGACA TTATACCTTT ATTACCTCTT     1906

TATTTTATTA CCTCTATAAT AAAATGATAC CTTTCATGTA AAAAAAAAAA AAAA           1960

(SEQ. ID No: 9)
```

TABLE VII

Full DNA and Deduced Protein Sequence for CR6

```
GTGGGTGCGC CGTGCTGAGC TCTGGCTGTC AGTGTGTTCG CCCGCGTCCC CTCCGCGCTC        60

TCCGCTTGTG GATAACTAGC TGCTGGTTGA TCGCACT ATG ACT CTG GAA GAA GTC       115
                                        Met Thr Leu Glu Glu Val
                                         1                   5

CGC GGC CAG GAC ACA GTT CCG GAA AGC ACA GCC AGG ATG CAG GGT GCC        163
```

TABLE VII-continued

Full DNA and Deduced Protein Sequence for CR6

| | | | | | | | | | | | | |
|---|---|---|---|---|---|---|---|---|---|---|---|---|
| Arg | Gly | Gln | Asp | Thr | Val | Pro | Glu | Ser | Thr | Ala | Arg | Met | Gln | Gly | Ala |
| | | | 10 | | | | 15 | | | | 20 | |

```
GGG AAA GCG CTG CAT GAG TTG CTG CTG TCG GCG CAG CGT CAG GGC TGC    211
Gly Lys Ala Leu His Glu Leu Leu Leu Ser Ala Gln Arg Gln Gly Cys
        25                  30                  35

CTC ACT GCC GGC GTC TAC GAG TCA GCC AAA GTC TTG AAC GTG GAC CCC    259
Leu Thr Ala Gly Val Tyr Glu Ser Ala Lys Val Leu Asn Val Asp Pro
    40                  45                  50

GAC AAT GTG ACC TTC TGT GTG CTG GCT GCG GGT GAG GAG GAC GAG GGC    307
Asp Asn Val Thr Phe Cys Val Leu Ala Ala Gly Glu Glu Asp Glu Gly
55                  60                  65                  70

GAC ATC GCG CTG CAG ATC CAT TTT ACG CTG ATC CAG GCT TTC TGC TGC    355
Asp Ile Ala Leu Gln Ile His Phe Thr Leu Ile Gln Ala Phe Cys Cys
        75                  80                  85

GAG AAC GAC ATC GAC ATA GTG CGC GTG GGC GAT GTG CAG CGG CTG GCG    403
Glu Asn Asp Ile Asp Ile Val Arg Val Gly Asp Val Gln Arg Leu Ala
            90                  95                  100

GCT ATC GTG GGC GCC GGC GAG GAG GCG GGT GCG CCG GGC GAC CTG CAC    451
Ala Ile Val Gly Ala Gly Glu Glu Ala Gly Ala Pro Gly Asp Leu His
                105                 110                 115

TGC ATC CTC ATT TCG AAC CCC AAC GAG GAC GCC TGG AAG GAT CCC CCC    499
Cys Ile Leu Ile Ser Asn Pro Asn Glu Asp Ala Trp Lys Asp Pro Ala
120                 125                 130

TTG GAG AAG CTC AGC CTG TTT TGC GAG GAG AGC CGC AGC GTT AAC GAC    547
Leu Glu Lys Leu Ser Leu Phe Cys Glu Glu Ser Arg Ser Val Asn Asp
135                 140                 145                 150

TGG GTG CCC AGC ATC ACC CTC CCC GAG   (SEQ. ID No: 31)              574
Trp Val Pro Ser Ile Thr Leu Pro Glu   (SEQ. ID No: 12)
                155
T GACAGCCCGG CGGGGACCTT                                             595

GGTCTGATCG ACGTGGTGAC GCCCCGGGGC GCCTAGAGCG CGGCTGGCTC TGTGGAGGGG    655

CCCTCCGAGG GTGCCCGAGT GCGGCGTGGA GACTGGCAGG CGGGGGGGGC GCCTGGAGAG    715

CGAGGAGGCG CGGCCTCCCG AGGAGGGGCC CGGTGGCGGC AGGGCCAGGC TGGTCCGAGC    775

TGAGGACTCT GCAAGTGTCT GGAGCGGCTG CTCGCCCAGG AAGGCCTAGG CTAGGACGTT    835

GGCCTCAGGG CCAGGAAGGA CAGACTGGCC GGGCAGGCGT GACTCAGCAG CCTGCGCTCG    895

GCAGGAAGGA GCGGCGCCCT GGACTTGGTA CAGTTTCAGG AGCGTGAAGG ACTTAACCGA    955

CTGCCGCTGC TTTTTCAAAA CGGATCCGGG CAATGCTTCG TTTTCTAAAG GATGCTGCTG    1015

TTGAGCTTTG AATTTTACAA TAAACTTTTT GAAACAAAAA AAAAAAAAA               1065
```

(SEQ. ID No: 11)

TABLE VIII

Full DNA Sequence and Protein Sequence for CR7

```
GCGCCGCATC CTGGAGGTTG GG ATG CTC TTG TCC AAA ATC AAC TCG CTT GCC    52
CGCGGCGTAG GACCTCCAAC CC TAC GAG AAC AGG TTT TAG TTG AGC GAA CGG
                       Met Leu Leu Ser Lys Ile Asn Ser Leu Ala
                        1               5                   10

CAC CTG CGC GCC CGC GCC TGC AAC GAC CTG CAC GCC ACC AAG CTG GCG    100
GTG GAC GCG CGG GCG CGG ACG TTG CTG GAC GTG CGG TGG TTC GAC CGC
His Leu Arg Ala Arg Ala Cys Asn Asp Leu His Ala Thr Lys Leu Ala
            15                  20                  25

CCG GGC AAG GAG AAG GAG CCC CTG GAG TCG CAG TAC CAG GTG GGC CCG    148
GGC CCG TTC CTC TTC CTC GGG GAC CTC AGC GTC ATG GTC CAC CCG GGC
```

TABLE VIII-continued

Full DNA Sequence and Protein Sequence for CR7

```
Pro Gly Lys Glu Lys Glu Pro Leu Glu Ser Gln Tyr Gln Val Gly Pro
             30                  35              40

CTA CTG GGC AGC GGC GGC TTC GGC TCG GTC TAC TCA GGC ATC CGC GTC     196
GAT GAC CCG TCG CCG CCG AAG CCG AGC CAG ATG AGT CCG TAG GCG CAG
Leu Leu Gly Ser Gly Gly Phe Gly Ser Val Tyr Ser Gly Ile Arg Val
             45                  50              55

TCC GAC AAC TTG CCG GTG GCC ATC AAA CAC GTG GAG AAG GAC CGG ATT     244
AGG CTG TTG AAC GGC CAC CGG TAG TTT GTG CAC CTC TTC CTG GCC TAA
Ser Asp Asn Leu Pro Val Ala Ile Lys His Val Glu Lys Asp Arg Ile
             60                  65              70

TCC GAC TGG GGA GAG CTG CCT AAT GGC ACT CGA GTG CCC ATG GAA GTG     292
AGG CTG ACC CCT CTC GAC GGA TTA CCG TGA GCT CAC GGG TAC CTT CAC
Ser Asp Trp Gly Glu Lue Pro Asn Gly Thr Arg Val Pro Met Glu Val
 75              80                  85                  90

GTC CTG CTG AAG AAG GTG AGC TCG GGT TTC TCC GGC GTC ATT AGG CTC     340
CAG GAC GAC TTC TTC CAC TCG AGC CCA AAG AGG CCG CAG TAA TCC GAG
Val Leu Leu Lys Lys Val Ser Ser Gly Phe Ser Gly Val Ile Arg Leu
             95                  100             105

CTG GAC TGG TTC GAG AGG CCC GAC AGT TTC GTC CTG ATC CTG GAG AGG     388
GAC CTG ACC AAG CTC TCC GGG CTG TCA AAG CAG GAC TAG GAC CTC TCC
Leu Asp Trp Phe Glu Arg Pro Asp Ser Phe Val Leu Ile Leu Glu Arg
             110                 115             120

CCC GAG CCG GTG CAA GAT CTC TTC GAC TTC ATC ACG GAA AGG GGA GCC     436
GGG CTC GGC CAC GTT CTA GAG AAG CTG AAG TAG TGC CTT TCC CCT CGG
Pro Glu Pro Val Gln Asp Leu Phe Asp Phe Ile Thr Glu Arg Gly Ala
             125                 130             135

CTG CAA GAG GAG CTG GCC CGC AGC TTC TTC TGG CAG GTG CTG GAG GCC     484
GAC GTT CTC CTC GAC CGG GCG TCG AAG AAG ACC GTC CAC GAC CTC CGG
Leu Gln Glu Glu Leu Ala Arg Ser Phe Phe Trp Gln Val Leu Glu Ala
             140                 145             150

GTG CGG CAC TGC CAC AAC TGC GGG GTG CTC CAC CGC GAC ATC AAG GAC     532
CAC GCC GTG ACG GTG TTG ACG CCC CAC GAG GTG GCG CTG TAG TTC CTG
Val Arg His Cys His Asn Cys Gly Val Leu His Arg Asp Ile Lys Asp
155              160                 165                 170

GAA AAC ATC CTT ATC GAC CTC AAT CGC GGC GAG CTC AAG CTC ATC GAC     580
CTT TTG TAG GAA TAG CTG GAG TTA GCG CCG CTC GAG TTC GAG TAG CTG
Glu Asn Ile Leu Ile Asp Leu Asn Arg Gly Glu Leu Lys Leu Ile Asp
             175                 180             185

TTC GGG TCG GGG GCG CTG CTC AAG GAC ACC GTC TAC ACG GAC TTC GAT     628
AAG CCC AGC CCC CGC GAC GAG TTC CTG TGG CAG ATG TGC CTG AAG CTA
Phe Gly Ser Gly Ala Leu Leu Lys Asp Thr Val Tyr Thr Asp Phe Asp
             190                 195             200

GGG ACC CGA GTG TAT AGC CCT CCA GAG TGG ATC CGC TAC CAT CGC TAC     676
CCC TGG GCT CAC ATA TCG GGA GGT CTC ACC TAG GCG ATG GTA GCG ATG
Gly Thr Arg Val Tyr Ser Pro Pro Glu Trp Ile Arg Tyr His Arg Tyr
             205                 210             215

CAT GGC AGG TCG GCG GCA GTC TGG TCC CTG GGG ATC CTG CTG TAT GAT     724
GTA CCG TCC AGC CGC CGT CAG ACC AGG GAC CCC TAG GAC GAC ATA CTA
His Gly Arg Ser Ala Ala Val Trp Ser Leu Gly Ile Leu Leu Tyr Asp
             220                 225             230

ATG GTG TGT GGA GAT ATT CCT TTC GAG CAT GAC GAA GAG ATC ATC AGG     772
TAC CAC ACA CCT CTA TAA GGA AAG CTC GTA CTG CTT CTC TAG TAG TCC
Met Val Cys Gly Asp Ile Pro Phe Glu His Asp Glu Glu Ile Ile Arg
235                 240                 245                 250

GGC CAG GTT TTC TTC AGG CAG AGG GTC TCT TCA GAA TGT CAG CAT CTC     820
CCG GTC CAA AAG AAG TCC GTC TCC CAG AGA AGT CTT ACA GTC GTA GAG
Gly Gln Val Phe Phe Arg Gln Arg Val Ser Ser Glu Cys Gln His Leu
                 255                 260             265

ATT AGA TGG TGC TTG GCC CTG AGA CCA TCA GAT AGG CCA ACC TTC GAA     868
TAA TCT ACC ACG AAC CGG GAC TCT GGT AGT CTA TCC GGT TGG AAG CTT
Ile Arg Trp Cys Leu Ala Leu Arg Pro Ser Asp Arg Pro Thr Phe Glu
             270                 275             280
```

TABLE VIII-continued

Full DNA Sequence and Protein Sequence for CR7

<u>GAA ATC CAG AAC CAT CCA TGG ATG CAA GAT GTT CTC CTG CCC CAG GAA</u>  916
CTT TAG GTC TTG GTA GGT ACC TAC GTT CTA CAA GAG GAC GGG GTC CTT
Glu Ile Gln Asn His Pro Trp Met Gln Asp Val Leu Leu Pro Gln Glu
                285                   290                  295

<u>ACT GCT GAG ATC CAC CTC CAC AGC CTG TCG CCG GGG CCC AGC AAA</u>  961
                                                      (SEQ. ID No: 35)

TGA CGA CTC TAG GTG GAG GTG TCG GAC AGC GGC CCC GGG TCG TTT
Thr Ala Glu Ile His Leu His Ser Leu Ser Pro Gly Pro Ser Lys (SEQ. ID No: 26)
        300                   305                   310                   313

TAGCAGCCT TTCTGGCAGG TCCTCCCCTC TCTTGTCAGA TGCCCAGGAG GGAAGCTTCT  1020

ATCGTCGGA AAGACCGTCC AGGAGGGGAG AGAACAGTCT ACGGGTCCTC CCTTCGAAGA

GTCTCCAGCT TTCCCGAGTA CCAGTGACAC GTCTCGCCAA GCAGGACAGT GCTTGATACA  1030

CAGAGGTCGA AAGGGCTCAT GGTCACTGTG CAGAGCGGTT CGTCCTGTCA CGAACTATGT

GGAACAACAT TTACAACTCA TTCCAGATCC CAGGCCCCTG GAGGCTGCCT CCCAACAGTG  1140

CCTTGTTGTA AATGTTGAGT AAGGTCTAGG GTCCGGGAC CTCCGACGGA GGGTTGTCAC

GGGAAGAGTG ACTCTCCAGG GGTCCTAGGC CTCAACTCCT CCCATAGATA CTCTCTTCTT  1200

CCCTTCTCAC TGAGAGGTCC CCAGGATCCG GAGTTGAGGA GGGTATCTAT GAGAGAAGAA

CTCATAGGTG TCCAGCATTG CTGGACTCTG AAATATCCCG GGGGTGGGGG GTGGGGGTGG  1260

GAGTATCCAC AGGTCGTAAC GACCTGAGAC TTTATAGGGC CCCCACCCCC CACCCCCACC

GTCAGAACCC TGCCATGGAA CTGTTTCCTT CATCATGAGT TCTGCTGAAT GCCGCGATGG  1320

CAGTCTTGGG ACGGTACCTT GACAAAGGAA GTAGTACTCA AGACGACTTA CGGCGCTACC

GTCAGGTAGG GGGGAAACAG GTTGGGATGG GATAGGACTA GCACCATTTT AAGTCCCTGT  1380

CAGTCCATCC CCCCTTTGTC CAACCCTACC CTATCCTGAT CGTGGTAAAA TTCAGGGACA

CACCTCTTCC GACTCTTTCT GAGTGCCTTC TGTGGGACT CCGGCTGTGC TGGGAGAAAT  1440

GTGGAGAAGG CTGAGAAAGA CTCACGGAAG ACACCCCTGA GGCCGACACG ACCCTCTTTA

ACTTGAACTT GCCTCTTTTA CCTGCTGCTT CTCCAAAAAT CTGCCTGGGT TTTGTTCCCT  1500

TGAACTTGAA CGGAGAAAAT GGACGACGAA GAGGTTTTTA GACGGACCCA AAACAAGGGA

ATTTTTCTCT CCTGTCCTCC CTCACCCCCT CCTTCATATG AAAGGTGCCA TGGAAGAGGC  1560

TAAAAAGAGA GGACAGGAGG GAGTGGGGGA GGAAGTATAC TTTCCACGGT ACCTTCTCCG

TACAGGGCCA AACGCTGAGC CACCTGCCCT TTTTTCTCCT CCTTTAGTAA AACTCCGAGT  1620

ATGTCCCGGT TTGCGACTCG GTGGACGGGA AAAAGAGGA GGAAATCATT TTGAGGCTCA

GAACTGGTCT TCCTTTTTGG TTTTTACTTA ACTGTTTCAA AGCCAAGACC TCACACACAC  1680

CTTGACCAGA AGGAAAAACC AAAAATGAAT TGACAAAGTT TCGGTTCTGG AGTGTGTGTG

AAAAAATGCA CAAACAATGC AATCAACAGA AAAGCTGTAA ATGTGTGTAC AGTTGGCATG  1740

TTTTTTACGT GTTTGTTACG TTAGTTGTCT TTTCGACATT TACACACATG TCAACCGTAC

GTAGTATACA AAAAGATTGT AGTGGATCTA ATTTTTAAGA AATTTTGCCT TTAAGTTATT  1800

CATCATATGT TTTTCTAACA TCACCTAGAT TAAAAATTCT TTAAAACGGA AATTCAATAA

TTACCTGTTT TTGTTTCTTG TTTTGAAAGA TGCGCATTCT AACCTGGAGG TCAATGTTAT  1860

AATGGACAAA AACAAAGAAC AAAACTTTCT ACGCGTAAGA TTGGACCTCC AGTTACAATA

GTATTTATTT ATTTATTTAT TTGGTTCCCT TCCTATTCCA AGCTTCGCTG CTGCCCTAGT  1920

CATAAATAAA TAAATAAATA AACCAAGGGA AGGATAAGGT TCGAAGCGAC GACGGGATCA

TABLE VIII-continued

Full DNA Sequence and Protein Sequence for CR7

| | | | | | |
|---|---|---|---|---|---|
| TTTCTTTCCT | CCTTTCCTCC | TCTGACTTGG | GGACCTTTTG | GGGGAGGGCT | GCGACGCTTG | 1980 |
| AAAGAAAGGA | GGAAAGGAGG | AGACTGAACC | CCTGGAAAAC | CCCCTCCCGA | CGCTGCGAAC | |
| CTCTGTTTGT | GGGGTGACGG | GACTCAGGCG | GGACAGTGCT | GCAGCTCCCT | GGCTTCTGTG | 2040 |
| GAGACAAACA | CCCCACTGCC | CTGAGTCCGC | CCTGTCACGA | CGTCGAGGGA | CCGAAGACAC | |
| GGGCCCCTCA | CCTACTTACC | CAGGTGGGTC | CCGGCTCTGT | GGGTGATGGG | GAGGGGCATT | 2100 |
| CCCGGGGAGT | GGATGAATGG | GTCCACCCAG | GGCCGAGACA | CCCACTACCC | CTCCCCGTAA | |
| GCTGACTGTG | TATATAGGAT | AATTATGAAA | AGCAGTTCTG | GATGGTGTGC | CTTCCAGATC | 2160 |
| CGACTGACAC | ATATATCCTA | TTAATACTTT | TCGTCAAGAC | CTACCACACG | GAAGGTCTAG | |
| CTCTCTGGGG | CTGTGTTTTG | AGCAGCAGGT | AGCCTGCTGG | TTTTATCTGA | GTGAAATACT | 2220 |
| GAGAGACCCC | GACACAAAAC | TCGTCGTCCA | TCGGACGACC | AAAATAGACT | CACTTTATGA | |
| GTACAGGGGA | ATAAAAGAGA | TCTTATTTTT | TTTTTTATAC | TTGGCGTTTT | TTGAATAAAA | 2280 |
| CATGTCCCCT | TATTTTCTCT | AGAATAAAAA | AAAAAATATG | AACCGCAAAA | AACTTATTTT | |
| ACCTTTTGTC | TTAAAAC | (SEQ. ID No: 25) | | | | 2297 |
| TGGAAAACAG | AATTTTG | (SEQ. ID No: 34) | | | | 2241 |

TABLE IX

Full DNA and Deduced Protein Sequence for CR8

```
CACACCGCCA GTCTGTGCGC TGAGTCGGAG CCAGAGGCCG CGGGGACACC GGGCCATGCA    60

CGCCCCCAAC TGAAGCTGCA TCTCAAAGCC GAAGATTCCA GCAGCCCAGG GGATTTCAAA   120

GAGCTCAGAC TCAGAGGAAC ATCTGCGGAG AGACCCCCGA AGCCCTCTCC AGGGCAGTCC   180

TCATCCAGAC GCTCCGTTAG TGCAGACAGG AGCGCGCAGT GGCCCCGGCT CGCCGCGCC    239

ATG GAG CGG ATC CCC AGC GCG CAA CCA CCC CCC GCC TGC CTG CCC AAA    287
Met Glu Arg Ile Pro Ser Ala Gln Pro Pro Pro Ala Cys Leu Pro Lys
  1               5                  10                  15

GCA CCG GGA CTG GAG CAC CGA GAC CTA CCA GGG ATG TAC CCT GCC CAC    335
Ala Pro Gly Leu Glu His Arg Asp Leu Pro Gly Met Tyr Pro Ala His
             20                  25                  30

ATG TAC CAA GTG TAC AAG TCA AGA CGG GGA ATA AAG CGG AGC GAG GAC    383
Met Tyr Gln Val Tyr Lys Ser Arg Arg Gly Ile Lys Arg Ser Glu Asp
         35                  40                  45

AGC AAG GAG ACC TAC AAA TTG CCG CAC CGG CTC TTC GAG AAA AAG AGA    431
Ser Lys Glu Thr Tyr Lys Leu Pro His Arg Leu Phe Glu Lys Lys Arg
     50                  55                  60

CGT GAC CGG ATT AAC GAG TGC ATC GCC CAG CTG AAG GAT CTC CTA CCC    479
Arg Asp Arg Ile Asn Glu Cys Ile Ala Gln Leu Lys Asp Leu Leu Pro
 65                  70                  75                  80

GAA CAT CTC AAA CTT ACA ACT TTG GGT CAC TTG GAA AAA GCA GTG GTT    527
Glu His Leu Lys Leu Thr Thr Leu Gly His Leu Glu Lys Ala Val Val
                 85                  90                  95

CTT GAA CTT ACC TTG AAG CAT GTG AAA GCA CTA ACA AAC CTA ATT GAT    575
Leu Glu Leu Thr Leu Lys His Val Lys Ala Leu Thr Asn Leu Ile Asp
            100                 105                 110

CAG CAG CAG CAG AAA ATC ATT GCC CTG CAG AGT GGT TTA CAA GCT GGT    623
Gln Gln Gln Gln Lys Ile Ile Ala Leu Gln ser Gly Leu Gln Ala Gly
        115                 120                 125

GAG CTG TCA GGG AGA AAT GTC GAA ACA GGT CAA GAG ATG TTC TGC TCA    671
```

TABLE IX-continued

Full DNA and Deduced Protein Sequence for CR8

```
                Glu Leu Ser Gly Arg Asn Val Glu Thr Gly Gln Glu Met Phe Cys Ser
                    130                 135                 140

GGT TTC CAG ACA TGT GCC CGG GAG GTG CTT CAG TAT CTG GCC AAG CAC                 719
Gly Phe Gln Thr Cys Ala Arg Glu Val Leu Gln Tyr Leu Ala Lys His
145                 150                 155

GAG AAC ACT CGG GAC CTG AAG TCT TCG CAG CTT GTC ACC CAC CTC CAC                 767
Glu Asn Thr Arg Asp Leu Lys Ser Ser Gln Leu Val Thr His Leu His
                165                 170                 175

CGG GTG GTC TCG GAG CTG CTG CAG GGT GGT ACC TCC AGG AAG CCA TCA                 815
Arg Val Val Ser Glu Leu Leu Gln Gly Gly Thr Ser Arg Lys Pro Ser
                    180                 185                 190

GAC CCA GCT CCC AAA GTG ATG GAC TTC AAG GAA AAA CCC AGC TCT CCG                 863
Asp Pro Ala Pro Lys Val Met Asp Phe Lys Glu Lys Pro Ser Ser Pro
                195                 200                 205

GCC AAA GGT TCG GAA GGT CCT GGG AAA AAC TGC GTG CCA GTC ATC CAG                 911
Ala Lys Gly Ser Glu Gly Pro Gly Lys Asn Cys Val Pro Val Ile Gln
210                 215                 220

CGG ACT TTC GCT CAC TCG AGT GGG GAG CAG AGC GGC AGC GAC ACG GAC                 959
Arg Thr Phe Ala His Ser Ser Gly Glu Gln Ser Gly Ser Asp Thr Asp
225                 230                 235                 240

ACA GAC AGT GGC TAT GGA GGA GAT TCG GAG AAG GGC GAC TTG CGC AGT                1007
Thr Asp Ser Gly Tyr Gly Gly Asp Ser Glu Lys Gly Asp Leu Arg Ser
                    245                 250                 255

GAG CAG CCG TGC TTC AAA AGT GAC CAC GGA CGC AGG TTC ACG ATG GGA                1055
Glu Gln Pro Cys Phe Lys Ser Asp His Gly Arg Arg Phe Thr Met Gly
                260                 265                 270

GAA AGG ATC GGC GCA ATT AAG CAA GAG TCC GAA GAA CCC CCC ACA AAA                1103
Glu Arg Ile Gly Ala Ile Lys Gln Glu Ser Glu Glu Pro Pro Thr Lys
                    275                 280                 285

AAG AAC CGG ATG CAG CTT TCG GAT GAT GAA GGC CAT TTC ACT AGC AGT                1151
Lys Asn Arg Met Gln Leu Ser Asp Asp Glu Gly His Phe Thr Ser Ser
                290                 295                 300

GAC CTG ATC AGC TCC CCG TTC CTG GGC CCA CAC CCA CAC CAG CCT CCT                1199
Asp Leu Ile Ser Ser Pro Phe Leu Gly Pro His Pro His Gln Pro Pro
305                 310                 315                 320

TCC TGC CTG CCC TTC TAC CTG ATC CCA CCT TCA GCG ACT GCC TAC CTG                1247
Phe Cys Leu Pro Phe Tyr Leu Ile Pro Pro Ser Ala Thr Ala Tyr Leu
                    325                 330                 335

CCC ATG CTG GAG AAG TGC TGG TAT CCC ACC TCA GTG CCA GTG CTA TAC                1295
Pro Met Leu Glu Lys Cys Trp Tyr Pro Thr Ser Val Pro Val Leu Tyr
                340                 345                 350

CCA GGC CTC AAC GCC TCT GCC GCA GCC CTC TCT AGC TTC ATG AAC CCA                1343
Pro Gly Leu Asn Ala Ser Ala Ala Ala Leu Ser Ser Phe Met Asn Pro
                    355                 360                 365

GAC AAG ATC TCG GCT CCC TTG CTC ATG CCC CAG AGA CTC CCT TCT CCC                1391
Asp Lys Ile Ser Ala Pro Leu Leu Met Pro Gln Arg Leu Pro Ser Pro
370                 375                 380

TTG CCA GCT CAT CCG TCC GTC GAC TCT TCT GTC TTG CTC CAA GCT CTG                1439
Leu Pro Ala His Pro Ser Val Asp Ser Ser Val Leu Leu Gln Ala Leu
385                 390                 395                 400

AAG CCA ATC CCC CCT TTA AAC TTA GAA ACC AAA GAC  (SEQ. ID No: 32)              1475
Lys Pro Ile Pro Pro Leu Asn Leu Glu Thr Lys Asp  (SEQ. ID No: 14)
                    405                 410

T AAACTCTCTA                                                                    1486

GGGGATCCTG CTGCTTTNGCT TTCCTNCCTC GCTACTTCCT AAAAAGCAAC CNNAAAGNTT             1546

TNGTGAATGC TGNNAGANTG TTGCATTGTG TATACTGAGA TAATCTGAGG CATGGAGAGC             1606
```

TABLE IX-continued

Full DNA and Deduced Protein Sequence for CR8

| | | | | | | |
|---|---|---|---|---|---|---|
| AGANNCAGGG | TGTGTGTGTG | TGTGTGTGTG | TGTGTGTGTG | TATGTGCGTG | TGCGTGCACA | 1666 |
| TGTGTGCCTG | CGTGTTGGTA | TAGGACTTTA | NNGCTCCTTN | NGGCATAGGG | AAGTCACGAA | 1726 |
| GGATTGCTNG | ACATCAGGAG | ACTNGGGGGG | GATTGTAGCA | GACGTCTGGG | CTTNNCCCCA | 1786 |
| CCCAGAGAAT | AGCCCCCNNC | NANACANATC | AGCTGGATTT | ACAAAAGCTT | CAAAGTCTTG | 1846 |
| GTCTGTGAGT | CACTCTTCAG | TTTGGGAGCT | GGGTCTGTGG | CTTTGATCAG | AAGGTACTTT | 1906 |
| CAAAAGAGGG | CTTTCCAGGG | CTCAGCTCCC | AACCAGCTGT | TAGGACCCCA | CCCTTTTGCC | 1966 |
| TTTATTGTCG | ACGTGACTCA | CCAGACGTCG | GGGAGAGAGA | GCAGTCAGAC | CGAGCTTTTC | 2026 |
| TGCTAACATG | GGGAGGGTAG | CAGACACTGG | CATAGCACGG | TAGTGGTTTG | GGGGAGGGTT | 2086 |
| TCCGCAGGTC | TGCTCCCCAC | CCCTGCCTCG | GAAGAATAAA | GAGAATGTAG | TTCCCTACTC | 2146 |
| AGGCTTTCGT | AGTGATTAGC | TTACTAAGGA | ACTGAAAATG | GGCCCCTTGT | ACAAGCTGAG | 2206 |
| CTGCCCCGGA | GGGAGGGAGG | AGTTCCCTGG | GCTTCTGGCA | CCTGTTTCTA | GGCCTAACCA | 2266 |
| TTAGTACTTA | CTGTGCAGGG | AACCAAACCA | AGGTCTGAGA | AATGCGGACA | NCCCGAGCGA | 2326 |
| GCACCCCAAA | GTGCACAAAG | CTGAGTAAAA | AGCTGCCCCC | TTCAAACAGA | ACTAGACTCA | 2386 |
| GTTTTCAATT | CCATCCTAAA | ACTCCTTTTA | ACCAAGCTTA | GCTTCTCAAA | GGGCTAACCA | 2446 |
| AGCCTTGGAA | CCGCCAGATC | CTTTCTGTAG | GCTAATTCCT | CTTGGCCAAC | GGCATATGGA | 2506 |
| GTGTCCTTAT | TGCTAAAAAG | GATTCCGNCT | CCTTCAAAGA | AGTTTTATTT | TTGGTCCAGA | 2566 |
| GTACTTGTTT | TCCCGATGTG | TCCAGCCAGC | TCCGCAGCAG | CTTTTCAAAA | TGCACTATGC | 2626 |
| CTGATTGCTG | ATCGTGTTTT | AACTTTTTCT | TTTCCTGTTT | TTATTTTGGT | ATTAAGTCGC | 2686 |
| TGGCTTTATT | TGTAAAGCTG | TTATAAATAT | ATATTATATN | AANTATATTA | AAAAGGAAAN | 2746 |
| TGTTNCAGAT | GTTTATTTGT | ATAATTACTT | GATTCACANA | GNGAGAAAAA | NTGANTGTAT | 2806 |
| TCCTGTNTTN | GAAGAGAAGA | NNAATTTTTT | TTTTCTCTAG | GGAGAGGTAC | AGNGTTNNTN | 2866 |
| TTTTGGGGCC | TNCCNGAAGG | GGTAAANNNG | AAAATNTTTC | TATNTATGAG | TAAATGTTAA | 2926 |
| GTAGTTGTNT | NAAAATACTN | AATAAAATAA | TTCTCTCCCT | GTGGNNGAGA | NAAC | 2980 |

(SEQ. ID No: 13).

1. A substantially pure polynucleotide, comprising a nucleic acid selected from the group consisting of
   (A) a sense nucleotide segment encoding amino acids 1–159 of SEQ. ID No:12, alleles thereof, antibody binding fragments thereof at least 20 amino acids long and fusion proteins thereof;
   (B) nucleotide segments which are anti-sense to segments in (A); and
   (C) primers/probes at least 60 consecutive nucleotides long complementary to the segments of (A) and (B).

2. The polynucleotide of claim 1, wherein the primers/probes comprise at least 60 consecutive nucleotides of the sense or anti-sense nucleotide segments.

3. The polynucleotide of claim 1, wherein the sense nucleotide segment encodes a fusion protein comprising (A) and an additional polynucleotide.

4. The polynucleotide of claim 1, comprising a nucleic acid selected from the group consisting of a sense nucleotide segment and alleles thereof encoding a polypeptide selected from the group consisting of amino acid residues 1–159 of SEQ. ID NO:12, its antibody binding fragments thereof at least 20 amino acids long and fusion proteins thereof.

5. The polynucleotide of claim 1, wherein the nucleic acid comprises an anti-sense nucleotide segment.

6. The polynucleotide of claim 1, wherein the nucleic acid comprises an allele or encodes an antibody binding fragment.

7. The polynucleotide of claim 1, wherein the nucleotide segment encodes an antibody binding fragment at least 20 amino acids long.

8. The polynucleotide of claim 1, comprising
   (A) primers/probes of at least 60 consecutive nucleotides of the nucleotide segment encoding a polypeptide selected from the group consisting of amino acid residues 1–159 of SEQ. ID NO:12, and antibody fragments thereof;
   (B) alleles encoding amino acids 1–159 of SEQ. ID No:12 or antibody binding fragments thereof at least 20 amino acids long; or
   (C) antisense poly nucleotides thereof.

9. The polynucleotide of claim 1, wherein the nucleotide segment comprises at least 60 consecutive nucleotides of SEQ. ID No:11.

10. The polynucleotide of claim 1, wherein the nucleic acid is selected from the group consisting of
    (A) nucleotide segments selected from the group consisting of SEQ.ID No:11, SEQ.ID No:31 and alleles thereof;

(B) nucleic acids encoding fusion proteins comprising sense nucleotide segments encoding amino acid residues 1–159 of SEQ ID NO:12 and alleles thereof;

(C) primers/probes at least 60 nucleotides long complementary to the segments in (A) and (B); and (D) nucleotide segments which are anti-sense to the nucleotide segments in (A), (B) and (C).

11. The polynucleotide of claim 9, wherein the nucleic acid comprises SEQ.ID No:11 or SEQ.ID No:31.

12. The polynucleotide of claim 1, wherein the nucleic acid encodes amino acid residues 1–159 of SEQ ID NO:12.

13. The polynucleotide of claim 3, wherein the nucleic acid comprises an additional polynucleotide encoding a polypeptide substantially unrelated to amino acids residues 1–159 of SEQ ID NO:12.

14. The polynucleotide of claim 3, wherein the additional polynucleotide comprises a nucleic acid selected from the group consisting of (A) sense nucleotide segments encoding amino acids 1–202 of SEQ.ID No:2, 1–60 of SEQ.ID No:4, 1–358 of SEQ.ID No:6, 1–763 of SEQ.ID No:8, 1–258 of SEQ.ID No:10, 1–412 of SEQ.ID No:14, polymerase activating peptide, c-raf, c-fos, c-myc, c-myb, and pim-1, and antibody binding fragments thereof at least 5 amino acids long and (B) probes/primers at least 15 consecutive nucleotides long complementary to nucleotide segments in (A).

15. The polynucleotide of claim 14, wherein the additional polynucleotide comprises a nucleic acid selected from the group consisting of sense and anti-sense segments of SEQ.ID No:3, SEQ.ID No:5, SEQ.ID No:7, SEQ.ID No:9, SEQ.ID No: 13, nucleotide segments encoding polymerase activating peptide, c-raf, c-myc, c-fos, c-myb, and pim-1probes/primers at least 20 consecutive nucleotides long complementary to sense and anti-sense nucleotide segments and alleles thereof and fragments thereof at least 20 nucleotides long.

16. The polynucleotide of claim 1, being a DNA.

17. The polynucleotide of claim 1, being an RNA.

18. The polynucleotide of claim 1, wherein the nucleic acid comprises a probe/primer comprising a nucleotide segment at least 60 consecutive nucleotides long complementary to the sense or anti-sense sequence nucleotide segments.

19. A composition, comprising the polynucleotide of claim 1, and a diluent or carrier.

20. The composition of claim 19, where the diluent or carrier comprises a pharmaceutically acceptable diluent or carrier.

21. A vector having the polynucleotide of claim 1 linked thereto.

22. A vector having the polynucleotide of claim 4 linked in reading frame thereto.

23. The vector of claim 22, comprising an expression vector.

24. A host cell transfected with the vector of claim 21.

25. A host cell transfected with the vector of claim 23.

26. A method for producing a polypeptide, comprising culturing a host cell transfected with the vector of claim 23, in an expression medium, under conditions effective to allow the expression of the polypeptide; and separating the polypeptide from the cells.

27. The method of claim 26, further comprising separating the polypeptide from the medium.

28. The method of claim 26, wherein the vector comprises a nucleic acid selected from the group consisting of (A) a sense nucleotide segment encoded a amino acid residues 1–159 of SEQ ID NO:12, alleles thereof, antibody binding fragments thereof at least 20 amino acids long and fusion proteins thereof;

(B) nucleotide segments which are anti-sense to segments in (A); and (C) primers/probes at least 60 consecutive nucleotides long complementary to the segments of (A) and (B).

29. A method for producing a polypeptide, comprising culturing the transfected host cell of claim 25, in an expression medium, under conditions effective to allow the expression of the polypeptide; and separating the polypeptide from the cells.

30. The method of claim 29, further comprising separating the polypeptide from the medium.

31. The method of claim 30, wherein the vector comprises a nucleic acid selected from the group consisting of (A) a sense nucleotide segment encoding amino acid residues 1–159 of SEQ ID NO: 12, alleles thereof antibody binding fragments thereof at least 20 amino acids long and fusion proteins thereof;

(B) nucleotide segments which are anti-sense to segments in (A); and (C) primers/probes at least 60 consecutive nucleotides long complementary to the segments of (A) and (B).

32. A DNA, having a nucleotide sequence complementary to the polynucleotide of claim 1.

33. An RNA, having a polynucleotide sequence corresponding to the DNA of claim 32.

34. A composition, comprising the DNA of claim 32, and a carrier or diluent.

35. A composition, comprising the RNA of claim 33, and a carrier or diluent.

36. A vector, comprising the DNA of claim 32 linked thereto.

37. A host cell, transfected with the vector of claim 36.

38. A cell culture, comprising a host cell comprising a vector comprising the probe/primer of claim 18.

39. A composition, comprising the probe/primer of claim 18, and a carrier or diluent.

40. A vector, comprising the probe/primer of claim 18 linked thereto.

41. A host cell, transfected with the vector of claim 40.

42. A hybridization kit, comprising the polynucleotide of claim 4, and instructions for its use.

* * * * *

UNITED STATES PATENT AND TRADEMARK OFFICE
CERTIFICATE OF CORRECTION

PATENT NO. : 6,027,914
DATED : Feb 22, 2000
INVENTOR(S) : Smith et al.

It is certified that error appears in the above-identified patent and that said Letters Patent is hereby corrected as shown below:

Column 131, lines 34 and 35 delete" pim-1probes/primers" and insert therefor --pim-1, probes/primers--;
Column 132, line 10, delete "encoded a" and insert therefor--encoding--.

Signed and Sealed this

Fifth Day of December, 2000

Attest:

Attesting Officer

Q. TODD DICKINSON
Director of Patents and Trademarks